(12) United States Patent
Kawaoka et al.

(10) Patent No.: US 11,389,523 B2
(45) Date of Patent: Jul. 19, 2022

(54) VECTORS FOR ELICITING IMMUNE RESPONSES TO NON-DOMINANT EPITOPES IN THE HEMAGGLUTININ (HA) PROTEIN

(71) Applicant: Wisconsin Alumni Research Foundation (WARF), Madison, WI (US)

(72) Inventors: Yoshihiro Kawaoka, Middleton, WI (US); Gabriele Neumann, Madison, WI (US); Huihui Kong, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 29 days.

(21) Appl. No.: 16/545,761

(22) Filed: Aug. 20, 2019

(65) Prior Publication Data
US 2020/0188506 A1 Jun. 18, 2020

Related U.S. Application Data

(60) Provisional application No. 62/719,952, filed on Aug. 20, 2018.

(51) Int. Cl.
| | |
|---|---|
| *A61K 39/145* | (2006.01) |
| *C12N 15/86* | (2006.01) |
| *C07K 16/34* | (2006.01) |
| *C07K 16/10* | (2006.01) |
| *A61K 39/00* | (2006.01) |

(52) U.S. Cl.
CPC ........ *A61K 39/145* (2013.01); *C07K 16/1018* (2013.01); *C07K 16/34* (2013.01); *C12N 15/86* (2013.01); *A61K 2039/521* (2013.01); *A61K 2039/5258* (2013.01)

(58) Field of Classification Search
None
See application file for complete search history.

(56) References Cited

U.S. PATENT DOCUMENTS

| | | | |
|---|---|---|---|
| 2011/0020374 A1* | 1/2011 | Frazer | A61K 48/0066 424/184.1 |
| 2012/0058124 A1 | 3/2012 | Kurosawa et al. | |
| 2020/0188506 A1* | 6/2020 | Kawaoka | C07K 16/1018 |

FOREIGN PATENT DOCUMENTS

| | | |
|---|---|---|
| WO | WO-2017/136575 A1 | 8/2017 |
| WO | WO-2020/041311 A1 | 2/2020 |

OTHER PUBLICATIONS

Li et al. (Nature Microbiology. 2016; 1 (6): 1-10).*
Nara et al. (PLoS Biology. 2010; 8 (12): e1000571).*
(Continued)

*Primary Examiner* — Shanon A. Foley
(74) *Attorney, Agent, or Firm* — Schwegman Lundberg & Woessner, P.A.

(57) ABSTRACT

Methods of preparing influenza viruses having altered immunodominant epitopes in HA, e.g., having one or more residues in one or more of antigenic sites A-E in HA altered, and viral vectors, e.g., influenza virus VLPs or non-influenza viruses or VLPs thereof expressing or having influenza HAs with altered immunogenicity as a result of altered immunodominant epitopes therein are provided.

19 Claims, 45 Drawing Sheets
Specification includes a Sequence Listing.

(56) References Cited

OTHER PUBLICATIONS

Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.

Broecker, Felix, et al., "Immunodominance of Antigenic Site B in the Hemagglutinin of the Current H3N2 Infuenza Virus in Humans and Mice", Journal of Virology, 92(20): e01100-18, (Oct. 2018), 1-13.

Sun, Weina, et al., "Development of Influenza B Universal Vaccine Candidates Using the "Mosaic" Hemagglutinin Approach", American Society For Microbiology, Journal of Virology, Vaccines and Antiviral Agents, vol. 93, Issue 12, (Jun. 2019), 1-17.

"International Application Serial No. PCT/US2019/047263, International Search Report dated Dec. 20, 2019", 5 pgs.

"International Application Serial No. PCT/US2019/047263, Written Opinion dated Dec. 20, 2019", 6 pgs.

Cho, Alice, et al., "Implications of Broadly Neutralizing Antibodies in the Development of a Universal Influenza Vaccine", Current Opinion in Virology, vol. 17, (Apr. 1, 2016), 110-115.

Giles, Brendan Michael, "Development of Broadly Reactive Vaccine for Highly Pathogenic H5N1 Influenza", Retrieved from the Internet: <URL<http//search.proquest.com/docview/928138363>, (Jan. 1, 2011), 283 pgs.

Popova, Lyubov, et al., "Immunodominance of Antigenic Site B over Site of Hemagglutinin of Recent H3N2 Influenza Viruses", PLoS ONE, vol. 7 No. 7, (Jul. 25, 2012), e41895, 1-11.

* cited by examiner

Library Generation and Screening (C.1.2, C.1.3): Selection of 100 ID-EpiMut HAs

↓

Reactivity with H3 HA-and Stem-specific mAbs (C.1.4): Selection of 50 ID-EpiMut HAs

↓ ↓

Generation of 50 ID-EpiMut HA/VP40 VLPs Decorated with One EpiMut HA each (C.2.1.1)

Generation of 8 ID-EpiMut HA/VP40 VLPs (5VLPS Decorated with 10 Epimut HAs each; 2 VLPs Decorated with 25 EpiMut HAs Each; 1 VLP Decorated with 50 EpiMut HAs; C.2.1.2)

↓ ↓

Characterization of Mouse Sera (C.2.1.3): Selection of 30 ID-EpiMut HA/VP40 VLPs (Decorated with one EpiMut HA each)

Characterization of Mouse Sera (C.2.1.3): Elimination of VLPs That do not Elicit Sera with High Amounts of Abs to Immune-subdomomant Epitopes

↓ ↓

Mouse Immunization Studies (C>2.2); Vaccination Strategies 1-3 (Table 4)

Mouse Immunization Studies (C.2.2); Vaccination Strategies 4-6 (Table 4)

↓ ↓

Selection of top 10 Vaccination Regimen

↓

Challenge Studies in Mice (C.2.3): Selection of top 3 Vaccination Regimen

↓

Immunogenicity and Protective Efficacy in Ferrets (C.2.3, C.2.4) for the top 3 Vaccination Regimen

FIG. 5

```
DEFINITION  hemagglutinin, partial [Influenza A virus
            (A/California/7/2004(H3N2))].
ACCESSION   ABH01021
      1 qklpgndnst atlclghhav pngtivktit ndqievtnat elvqssstgg icdsphqild
     61 genctlidal lgdpqcdgfq nkkwdlfver skaysncypy dvpdyaslrs lvassgtlef
    121 nnesfnwtgv tqngtsssck rrsnnsffsr lnwlthlkfk ypalnvtmpn nekfdklyiw
    181 gvhhpgtnnd qislytqasg ritvstkrsq qtvipnigsr prvrdipsri siywtivkpg
    241 dillinstgn liaprgyfki rsgkssimrs dapigkcnse citpngsipn dkpfqnvnri
```
301 tygacpryvk qntlklatgm rnvpekqtr

```
DEFINITION hemagglutinin, partial [Influenza A virus(A/California/7/2004
            (cell-passaged)(H3))].
ACCESSION   ABO37489
      1 qklpgndnst atlclghhav pngtivktit ndqievtnat elvqssstgg icdsphqild
     61 genctlidal lgdpqcdgfq nkkwdlfver skaysncypy dvpdyaslrs lvassgtlef
    121 nnesfnwtgv tqngtssack rrsnnsffsr lnwlthlkfk ypalnvtmpn nekfdklyiw
    181 gvhhpgtnnd qislyaqasg ritvstkrsq qtvipnigsr prvrdipsri siywtivkpg
    241 dillinstgn liaprgyfki rsgkssimrs dapigkcnse citpngsipn dkpfqnvnri
    301 tygacpryvk qntlklatgm rnvpekqtrg ifgaiagfie ngwegmvdgw ygfrhqnseg
    361 iggaadlkst qaainqingk lnrligktne kfhqiekefs evegriqdle kyvedtkidl
    421 wsynaellva lenqhtidlt dsemnklfer tkkqlrenae dmgngcfkiy hkcdnacigs
```
481 irngtydhdv yrdealnnrf qikgvelksg yk

```
DEFINITION hemagglutinin, partial [Influenza A virus(A/California/7/2004
           (egg-passaged)(H3))].
ACCESSION ABO37490
      1 qklpgndnst atlclghhav pngtivktit ndqievtnat elvqssstgg icdsphqild
     61 genctlidal lgdpqcdgfq nkkwdlfver skaysncypy dvpdyaslrs lvassgtlef
    121 nnesfnwtgv tqngtsssck rrsnnsffsr lnwlthlkfk ypalnvtmpn nekfdklyiw
    181 gvhhpgtnnd qislytqasg ritvstkrsq qtvipnigsr prvrdipsri siywtivkpg
    241 dillinstgn liaprgyfki rsgkssimrs dapigkcnse citpngsipn dkpfqnvnri
    301 tygacpryvk qntlklatgm rnvpekqtrg ifgaiagfie ngwegmvdgw ygfrhqnseg
    361 iggaadlkst qaainqingk lnrligktne kfhqiekefs evegriqdle kyvedtkidl
```

FIG. 6A

```
421 wsynaellva lenqhtidlt dsemnklfer tkkqlrenae dmgngcfkiy

Sequence : gb:KP307984|gi:748112957|UniProtKB:A0A0C4X0C0|Organism: Influenza A virus (A/gyrfalcon/Washington/41088-6/2014(H5N8))|Strain Name:A/gyrfalcon/Washington/41088-6/2014|Protein Name:HA Hemagglutinin |Gene Symbol:HA|Segment:4|Subtype:H5N8|Host:Falcon

```
MEKIVLLLAV ISLVKSDQIC IGYHANNSTK QVDTIMEKNV TVTHAQDILE 050
KTHNGKLCDL NGVKPLILKD CSVAGWLLGN PMCDEFIRVP EWSYIVERAN 100
PANDLCYPGT LNDYEELKHL LSRINHFEKT LIIPRSSWPN HETSLGVSAA 150
CPYQGASSFF RNVVWLIKKN DAYPTIKISY NNTNREDLLI LWGIHHSNNA 200
AEQTNLYKNP DTYVSVGTST LNQRLVPKIA TRSQVNGQSG RMDFFWTILK 250
PNDAIHFESN GNFIAPEYAY KIVKKGDSTI MKSEMEYGHC NTKCQTPIGA 300
INSSMPFHNI HPLTIGECPK YVKSNKLVLA TGLRNSPLRE RRRKRGLFGA 350
IAGFIEGGWQ GMVDGWYGYH HSNEQGSGYA ADKESTQKAI DGVTNKVNSI 400
IDKMNTQFEA VGREFNNLER RIENLNKKME DGFLDVWTYN AELLVLMENE 450
RTLDFHDSNV KNLYDKVRLQ LRDNAKELGN GCFEFYHKCD NECMESVRNG 500
TYDYPKYSEE AILKREEISG VKLESIGTYQ ILSIYSTVAS SLALAIIVAG 550
LSLWMCSNGS LQCRICI                                     567
```

FIG. 7

MKANLLCALAAADADTICIGYHANNSTDTVDTVLEKNVTVTHSVNLLEDSHNGKLCRLKGIAPLQLKG
KCNIAGWLLGNPECDPLLPVRSWSYIVETPNESENGICYPGDFIDYEELREQLSSVSSFERFEIFPKE
SSWPNHNTNGVTAACSHEGKSSFYRNLLWLTEKEGSYPKLNSYVNKKGKEVLVLWGIHHPPNSKEQN
LYQNENAYVSVVTSNYNRRFTPEIAERPKVRDQAGRMNYYWTLLKPGDTIIFEANGNLIAPMYAFALS
RGFGSGIITSNASMHECNTKCQTPLGAINSSLPYQNIHPVTIGECPKYVRSAKLRMVTGLRNIPSIQS
RGLFGAIAGFIEGGWTGMIDGWYGYHHQNEQGSGYAADQKSTQNAINGITNKVNTVIEMNIQFTAVGK
EFNKLEKRMENLNNKKVDDGFLDIWTYNAELLVLLENERTLDFHDSNVKNLYEKVKSQLKNNAKE
IGNGCFEFYHKCDNECMESVRNGTYDYPKYSEESKLNREKVDGVKLESMGIYQILAIYSTVSSLVLLV
SLGAISFWMCSNGSLQCRIC

FIG. 8

1 Maiiylillf tavrgdqici gyhannstek vdtilernvt vthakdilek thngklckln
61 gipplelgdc siagwllgnp ecdrllsvpe wsyimekenp rdglcypgsf ndyeelkhll
121 ssvkhfekvk ilpkdrwtqh tttggsraca vasgnpsffrn mvwltekgsn ypvakgsynr
181 tsgeqmliiw gvhhpndate qrtlyqnvgt yvsvgtstln krstpeiatr pkvngqggrm
241 efswtlldmw dtinfestgn liapeygfki skrgssgimk tegtlenct kcqtplgain
301 ttlpfhnvhp ltigecpkyv kseklvlatg lrnvpqiesr glfgaiagfi eggwqgmvdg
361 wyghhsadq gsgyaadkes tqkafdgitn kvnsviekmn tqfeavgkef snlerrlenl
421 nkkmedgfld vwtynaellv lmenertldf hdsnvknlyd kvrmqlrdnv kelgngcfef
481 yhkcddecmn svkngtydyp kyeeesklnr neikgvklss mgvyqilaiy atvagslsla
541 immagisfwm csngslqcri ci

FIG. 9

```
  1 Maiiylilf tavrgdgici gyhannstek vdtilernvt vthakdilek thngklckln
 61 gipplelgdc siagwllgnp ecdrllsvpe wsyimekenp rdglcypgsf nd

FIG. 11B

| POSITION | WT | 1 | 2 | 4 | 5 | 6 | 9 | 10 | 11 | 12 | 14 | 15 | 16 | 17 | 22 | 23 | 24 | 25 | 26 | 28 | 29 | 30 |
|---|---|---|---|---|---|---|---|---|---|---|---|---|---|---|---|---|---|---|---|---|---|---|
| 1 | N | Y | M | K | Q | V | V | R | T | T | V | A | V | P | S | V | L | V | R | F | S | F |
| 2 | T | T | V | R | R | R | K | V | G | N | 3 | M | C | L | S | Q | N | R | R | D | R | V |
| 3 | T | T | V | G | T | R | V | K | L | N | S | N | I | T | T | V | N | I | Y | S | K | W |
| 4 | A | A | K | A | K | F | T | W | K | K | R | I | L | K | K | K | T | V | K | K | T | S |
| 5 | I | W | F | P | L | M | H | M | C | 3 | K | Z | K | R | T | K | R | N | T | G | N | M |
| 6 | R | R | S | T | D | N | N | E | G | S | Y | G | D | R | Q | E | S | K | N | A | R | H |
| 7 | S | S | G | D | A | T | R | R | V | G | D | A | G | P | F | Q | T | G | T | N | A | Q |
| 8 | S | S | P | R | G | P | W | R | P | R | S | W | V | D | K | G | H | N | E | V | A | P |
| 9 | T | T | V | C | M | V | A | I | Y | R | Q | R | A | I | G | H | S | S | R | A | Q | P |
| 10 | H | H | G | A | T | P | S | G | P | S | R | A | P | N | S | D | R | V | Q | W | T | G |
| 11 | L | L | V | R | G | P | L | P | L | S | S | R | S | A | R | L | G | T | P | L | H | R |
| 12 | N | N | S | P | R | H | V | R | Q | R | R | L | P | R | R | T | K | S | P | N | M | C |
| 13 | N | N | R | K | T | T | R | F | T | K | L | F | A | G | I | L | K | R | F | R | R | K |
| 14 | K | K | E | D | A | I | R | T | F | Q | R | Q | L | T | K | Q | E | H | S | G | K | C |
| 15 | F | F | A | G | G | Q | S | T | F | A | L | E | A | P | Q | N | P | L | R | R | F | T |
| 16 | A | A | Q | N | L | V | R | I | R | Q | R | A | P | S | N | P | L | F | S | L | N | S |
| 17 | D | D | K | K | E | L | P | S | R | P | T | I | C | E | T | T | S | Y | S | T | E | A |

FIG. 12B

| Ab | HK68 | EN72 | VVS | TX77 | BK79 | SI87 | BE89 | BE92 | WH95 | SY97 | FU02 | CA04 | WI05 | PE09 |
|---|---|---|---|---|---|---|---|---|---|---|---|---|---|---|
|  | >50 | >50 | >50 | >50 | >50 | >50 | >50 | >50 | >50 | 6.25 | 3.13 | 0.20 | 0.20 | 0.20 |
|  | >50 | >50 | >50 | >50 | 6.25 | >50 | 6.25 | >50 | >50 | 0.20 | 1.56 | 0.39 | 0.20 | 0.20 |
|  | >50 | >50 | >50 | >50 | >50 | >50 | >50 | >50 | >50 | 12.50 | 3.13 | 0.20 | 0.20 | 0.78 |
|  | >50 | >50 | >50 | >50 | >50 | >50 | >50 | >50 | >50 | 12.50 | 3.13 | 0.20 | 0.20 | 0.20 |
|  | >50 | >50 | >50 | >50 | >50 | >50 | >50 | >50 | >50 | >50 | 3.13 | 0.20 | 0.20 | >50 |
|  | >50 | >50 | >50 | >50 | >50 | >50 | >50 | >50 | >50 | 0.20 | 1.56 | 0.39 | 0.20 | >50 |
|  | >50 | >50 | >50 | >50 | >50 | >50 | >50 | 3.13 | 3.13 | 0.20 | 3.13 | 0.20 | 0.20 | 0.20 |
|  | >50 | >50 | >50 | 6.25 | >50 | 6.25 | 1.56 | 1.56 | >50 | 1.56 | 6.25 | 0.39 | 0.20 | 12.50 |
|  | >50 | >50 | >50 | >50 | 0.78 | 0.39 | >50 | 25.00 | 3.13 | 12.50 | 12.50 | 12.50 | 0.78 | 0.39 |
|  | >50 | 25.00 | >50 | >50 | 25.00 | >50 | 1.56 | 1.56 | >50 | 3.13 | >50 | >50 | 12.50 | 3.13 |
|  | >50 | 0.20 | >50 | 3.13 | 0.20 | 1.56 | >50 | 1.56 | 1.56 | >50 | >50 | 6.25 | 12.50 | 6.25 |
|  | >50 | >50 | 0.20 | 1.56 | 0.20 | 0.20 | 6.25 | 1.56 | 0.78 | 0.20 | 1.56 | >50 | 0.20 | 0.20 |
|  | >50 | >50 | 0.78 | >50 | 0.20 | 0.20 | 0.20 | 1.56 | 3.13 | 0.20 | 3.13 | 0.30 | 0.30 | >50 |
|  | 25.00 | >50 | >50 | >50 | 0.20 | 25.00 | 0.30 | 3.13 | 3.13 | 12.50 | 3.13 | 6.25 | 12.50 | 0.39 |
|  | >50 | >50 | >50 | >50 | >50 | 1.56 | >50 | 6.25 | 12.50 | 3.13 | 3.13 | 0.78 | 0.20 | 0.20 |
|  | >50 | >50 | >50 | >50 | 0.78 | >50 | >50 | >50 | >50 | 0.20 | 1.56 | 0.20 | 0.30 | 0.20 |
|  | 25.00 | >50 | >50 | >50 | >50 | >50 | >50 | >50 | >50 | >50 | >50 | 1.56 | 12.50 | 0.20 |
|  | 1.56 | >50 | >50 | >50 | >50 | >50 | >50 | >50 | >50 | >50 | >50 | >50 | >50 | >50 |

HK68 ← → HK14

| TX12 | HK14 | WT | mul-1 | mul-2 | mul-4 | mul-6 | mul-8 | mul-7 | mul-9 | mul-10 | mul-11 | mul-12 | mul-14 |
|---|---|---|---|---|---|---|---|---|---|---|---|---|---|
| 0.78 | >50 | 1.98 | 0.04 | 0.06 | 0.04 | 0.05 | 0.04 | 0.00 | 0.08 | 0.06 | 0.04 | 0.04 | 0.00 |
| 1.56 | >50 | 1.99 | 0.04 | 0.06 | 0.05 | 0.04 | 0.08 | 0.11 | 0.08 | 0.06 | 0.04 | 0.05 | 0.10 |
| 1.56 | >50 | | | | | | | | | | | | |
| 1.56 | >50 | 1.66 | 1.39 | 0.00 | 0.10 | 0.00 | 0.10 | 0.07 | 0.10 | 0.07 | 0.07 | 0.06 | 0.12 |
| 6.25 | >50 | 2.06 | 0.04 | 0.06 | 0.11 | 0.04 | 0.04 | 0.11 | 0.00 | 0.07 | 0.04 | 0.05 | 0.11 |
| 25.00 | >50 | 1.91 | 0.04 | 0.07 | 0.05 | 0.04 | 0.05 | 0.11 | 0.10 | 0.06 | 0.04 | 0.05 | 0.14 |
| 1.56 | >50 | 1.94 | 0.04 | 0.06 | 0.05 | 0.05 | 0.07 | 0.00 | 0.08 | 0.07 | 0.04 | 0.05 | 0.10 |
| 1.56 | >50 | | | | | | | | | | | | |
| 3.13 | >50 | | | | | | | | | | | | |
| 3.13 | >50 | 1.96 | 0.05 | 0.08 | 0.06 | 0.06 | 0.06 | 0.12 | 0.10 | 0.08 | 0.06 | 0.06 | 0.21 |
| 6.25 | 12.50 | 1.88 | 0.53 | 0.06 | 0.06 | 0.55 | 0.24 | 0.58 | 0.61 | 0.17 | 0.40 | 0.06 | 1.63 |
| 25.00 | >50 | 1.64 | 0.27 | 0.21 | 0.26 | 0.42 | 0.26 | 0.55 | 0.62 | 0.10 | 0.24 | 0.36 | 1.29 |
| 1.56 | 6.25 | 1.85 | 0.04 | 0.05 | 0.05 | 0.04 | 0.05 | 0.00 | 0.00 | 0.06 | 0.20 | 0.05 | 0.27 |
| 1.56 | >50 | 1.83 | 0.04 | 0.05 | 0.05 | 0.04 | 0.04 | 0.00 | 0.00 | 0.06 | 0.14 | 0.06 | 0.11 |
| 6.25 | >50 | 1.88 | 0.04 | 0.04 | 0.04 | 0.04 | 0.04 | 0.08 | 0.00 | 0.06 | 0.04 | 0.05 | 0.08 |
| 1.56 | 1.56 | 1.98 | 0.05 | 0.06 | 0.05 | 0.05 | 0.30 | 0.10 | 0.63 | 0.05 | 0.40 | 0.36 | 0.11 |
| 3.13 | >50 | 1.65 | 0.51 | 0.41 | 0.30 | 0.51 | 0.06 | 0.71 | 0.00 | 0.18 | 0.04 | 0.05 | 1.79 |
| 6.25 | 25.00 | 1.91 | 0.04 | 0.08 | 0.04 | 0.05 | 0.25 | 0.10 | 0.00 | 0.07 | 0.04 | 0.00 | 0.66 |
| 1.56 | >50 | 1.83 | 0.04 | 0.07 | 0.05 | 0.05 | 0.17 | 0.10 | 0.00 | 0.06 | 0.04 | 0.05 | 0.15 |
| 1.56 | >50 | 1.94 | 0.97 | 0.00 | 0.00 | 0.10 | | 0.10 | 0.08 | 0.07 | 0.08 | 0.06 | 0.12 |
| 0.78 | >50 | | | | | | | | | | | | |
| >50 | >50 | | | | | | | | | | | | |
| >50 | >50 | | | | | | | | | | | | |

FIG. 12C

| mul-15 | mul-16 | mul-17 | mul-21 | mul-22 | mul-23 | mul-24 | mul-25 | mul-60 | mul-67 | mul-68 | mul-70 | mul-71 |
|---|---|---|---|---|---|---|---|---|---|---|---|---|
| 0.07 | 0.11 | 0.12 | 0.08 | 0.08 | 0.10 | 0.08 | 0.13 | 0.07 | 0.08 | 0.00 | 0.07 | 0.08 |
| 0.26 | 0.13 | 0.11 | 0.08 | 0.08 | 0.15 | 0.08 | 0.14 | 0.07 | 0.08 | 0.08 | 0.07 | 0.08 |
| | | | | | | | | | | | | |
| 0.08 | 0.12 | 0.11 | 0.07 | 0.08 | 0.10 | 0.08 | 0.17 | 0.07 | 0.07 | 0.00 | 0.06 | 0.00 |
| 0.13 | 0.12 | 0.15 | 0.00 | 0.10 | 0.40 | 0.10 | 0.16 | 0.07 | 0.00 | 0.07 | 0.08 | 0.08 |
| 0.14 | 0.15 | 0.20 | 0.00 | 0.11 | 0.94 | 0.11 | 0.24 | 0.08 | 0.00 | 0.08 | 0.00 | 0.07 |
| 0.59 | 0.13 | 0.15 | 0.08 | 0.00 | 0.11 | 0.10 | 0.18 | 0.07 | 0.00 | 0.00 | 0.07 | 0.06 |
| | | | | | | | | | | | | |
| 0.16 | 0.20 | 0.21 | 0.11 | 0.13 | 0.17 | 0.13 | 0.24 | 0.00 | 0.10 | 0.10 | 0.08 | 0.00 |
| 0.15 | 0.11 | 0.39 | 0.00 | 0.26 | 1.50 | 0.28 | 0.36 | 0.13 | 0.40 | 0.60 | 0.50 | 0.62 |
| 1.47 | 1.55 | 1.87 | 0.62 | 1.42 | 1.45 | 1.39 | 1.84 | 0.58 | 0.56 | 0.62 | 0.58 | 0.64 |
| 0.00 | 0.11 | 0.13 | 0.00 | 0.11 | 1.02 | 0.10 | 0.15 | 0.08 | 0.08 | 0.08 | 0.07 | 0.07 |
| | | | | | | | | | | | | |
| 0.00 | 0.12 | 0.15 | 0.08 | 0.00 | 0.86 | 0.10 | 0.15 | 0.08 | 0.07 | 0.08 | 0.08 | 0.07 |
| 0.08 | 0.00 | 0.10 | 0.00 | 0.07 | 0.38 | 0.07 | 0.11 | 0.07 | 0.08 | 0.07 | 0.07 | 0.07 |
| 0.40 | 0.16 | 0.13 | 0.08 | 0.08 | 1.25 | 0.00 | 0.13 | 0.34 | 0.52 | 0.61 | 0.64 | 0.59 |
| 1.27 | 0.43 | 0.74 | 0.08 | 1.30 | 1.78 | 0.89 | 1.18 | 0.08 | 0.00 | 0.10 | 0.07 | 0.08 |
| 0.58 | 0.23 | 0.17 | 0.08 | 0.11 | 0.17 | 0.10 | 0.20 | 0.08 | 0.08 | 0.10 | 0.08 | 0.07 |
| 1.66 | 0.16 | 0.17 | 0.08 | 0.11 | 0.38 | 0.11 | 0.17 | 0.08 | 0.08 | 0.00 | 0.07 | 0.08 |
| 0.12 | 0.14 | 0.15 | 0.08 | 0.12 | 0.13 | 0.10 | 0.14 | | | | | |

FIG. 12D

| | | | | | | | | | | | | | |
|---|---|---|---|---|---|---|---|---|---|---|---|---|---|
| >50 | >50 | 25.00 | >50 | 25.00 | 12.50 | 12.50 | 25.00 | 25.00 | 25.00 | >50 | >50 | 6.25 | 6.25 |
| >50 | >50 | >50 | >50 | >50 | >50 | >50 | >50 | >50 | >50 | 12.50 | 3.13 | 0.20 | 0.39 |
| >50 | >50 | 25.00 | >50 | 25.00 | >50 | 12.50 | 25.00 | >50 | >50 | >50 | >50 | >50 | >50 |
| >50 | >50 | >50 | >50 | 12.50 | 12.50 | 12.50 | 25.00 | >50 | >50 | >50 | 25.00 | 12.50 | 12.50 |
| >50 | >50 | 6.25 | 3.13 | 3.13 | >50 | >50 | >50 | >50 | >50 | >50 | 1.56 | 25.00 | >50 |
| >50 | >50 | >50 | >50 | >50 | >50 | >50 | >50 | >50 | >50 | >50 | 1.56 | 0.30 | 0.78 |
| >50 | >50 | >50 | >50 | >50 | >50 | >50 | >50 | 1.56 | >50 | >50 | >50 | >50 | 6.25 |
| >50 | >50 | >50 | >50 | >50 | 12.50 | >50 | 25.00 | >50 | 3.13 | >50 | 12.50 | 6.25 | 0.39 |
| >50 | 25.00 | 25.00 | 12.50 | 25.00 | >50 | >50 | 0.78 | 6.25 | 0.20 | 0.78 | 3.13 | 0.20 | 0.39 |
| 25.00 | 6.25 | >50 | 3.13 | >50 | >50 | >50 | >50 | 0.20 | >50 | 0.78 | 6.25 | 0.39 | 6.25 |
| 6.25 | >50 | >50 | >50 | >50 | >50 | >50 | >50 | >50 | >50 | >50 | 3.13 | 0.20 | 12.50 |
| >50 | >50 | >50 | >50 | >50 | >50 | 25.00 | 25.00 | >50 | >50 | >50 | >50 | >50 | >50 |
| >50 | >50 | >50 | >50 | >50 | 25.00 | 12.50 | 12.50 | 12.50 | 12.50 | 25.00 | >50 | 25.00 | >50 |
| >50 | >50 | >50 | 12.50 | >50 | >50 | >50 | >50 | >50 | 12.50 | 12.50 | >50 | 6.25 | >50 |
| >50 | >50 | >50 | >50 | 12.50 | >50 | >50 | 12.50 | >50 | >50 | >50 | 0.20 | 3.13 | >50 |
| >50 | >50 | >50 | >50 | >50 | >50 | >50 | >50 | 25.00 | 6.25 | 25.00 | 0.20 | 0.20 | 0.20 |
| 25.00 | 25.00 | 25.00 | 12.50 | 25.00 | 12.50 | 12.50 | >50 | >50 | 0.20 | 0.20 | 12.50 | >50 | >50 |
| >50 | >50 | >50 | >50 | >50 | >50 | >50 | >50 | >50 | 25.00 | 25.00 | >50 | 25.00 | 25.00 |
| >50 | >50 | >50 | >50 | 25.00 | 12.50 | 12.50 | >50 | 25.00 | >50 | >50 | >50 | 6.25 | 25.00 |
| >50 | 25.00 | >50 | >50 | >50 | >50 | >50 | >50 | >50 | >50 | >50 | 25.00 | >50 | 25.00 |

FIG. 12E

| | | | | | | | | | | | | | |
|---|---|---|---|---|---|---|---|---|---|---|---|---|---|
| 25.00 | 25.00 | 1.70 | 0.41 | 0.40 | 0.27 | 0.54 | 0.37 | 0.62 | 0.68 | 0.30 | 0.50 | 0.42 | 1.64 |
| 0.78 | >50 | 1.82 | 0.04 | 0.07 | 0.04 | 0.05 | 0.04 | 0.10 | 0.00 | 0.06 | 0.04 | 0.05 | 0.13 |
| >50 | >50 | 1.02 | 1.91 | 0.64 | 0.26 | 1.00 | 1.42 | 0.11 | 0.11 | 0.20 | 0.14 | 0.18 | 0.30 |
| >50 | >50 | 0.91 | 0.10 | 0.83 | 0.14 | 0.84 | 0.08 | 0.12 | 0.31 | 0.17 | 0.11 | 0.20 | 0.25 |
| >50 | >50 | | | | | | | | | | | | |
| 0.78 | >50 | 1.44 | 0.11 | 1.79 | 0.95 | 2.08 | 0.11 | 0.61 | 0.65 | 1.08 | 1.21 | 0.97 | 1.40 |
| >50 | >50 | 1.80 | 0.69 | 0.10 | 0.08 | 0.00 | 0.08 | 0.00 | 0.08 | 0.08 | 0.00 | 0.08 | 0.11 |
| 1.56 | 12.50 | 1.77 | 0.04 | 0.04 | 0.05 | 0.04 | 0.04 | 0.60 | 0.08 | 0.05 | 0.04 | 0.05 | 0.00 |
| >50 | >50 | | | | | | | | | | | | |
| 6.25 | >50 | | | | | | | | | | | | |
| >50 | >50 | | | | | | | | | | | | |
| >50 | >50 | | | | | | | | | | | | |
| >50 | >50 | 1.69 | 0.11 | 0.10 | 0.08 | 0.42 | 0.00 | 0.61 | 0.08 | 0.08 | 0.00 | 0.08 | 0.12 |
| 12.50 | 12.50 | 1.98 | 0.04 | 0.06 | 0.04 | 0.04 | 0.04 | 0.10 | 0.08 | 0.06 | 0.04 | 0.05 | 0.16 |
| 0.78 | 3.13 | 1.81 | 1.90 | 0.10 | 0.07 | 0.00 | 1.49 | 0.00 | 0.08 | 0.08 | 0.12 | 0.08 | 0.30 |
| 0.30 | >50 | 2.00 | 1.96 | 0.10 | 0.07 | 0.10 | 1.65 | 0.00 | 0.07 | 0.00 | 0.08 | 0.00 | 0.34 |
| 0.30 | >50 | 1.64 | 1.82 | 1.57 | 0.88 | 2.09 | 1.45 | 0.70 | 0.74 | 0.71 | 1.23 | 1.02 | 1.33 |
| >50 | >50 | 1.63 | 1.99 | 1.76 | 0.91 | 1.94 | 1.53 | 0.64 | 0.71 | 0.82 | 1.31 | 1.24 | 1.72 |
| >50 | >50 | 1.96 | 0.84 | 1.50 | 1.12 | 1.69 | 0.17 | 0.68 | 0.77 | 0.96 | 1.27 | 1.07 | 1.74 |
| >50 | >50 | 1.39 | 0.58 | 1.84 | 1.23 | 2.13 | 0.07 | 0.67 | 0.70 | 0.86 | 1.43 | 1.17 | 1.56 |

FIG. 12F

| 1.51 | 1.64 | 2.04 | 0.66 | 1.52 | 1.56 | 1.64 | 1.92 | 0.63 | 0.64 | 0.66 | 0.64 |  |  |  | 0.07 | 1.22 | 1.86 | 0.61 | 1.11 | 0.99 | 1.32 | 1.86 | 0.51 | 0.43 | 0.63 | 0.58 | 0.55 |
|------|------|------|------|------|------|------|------|------|------|------|------|--|--|--|------|------|------|------|------|------|------|------|------|------|------|------|------|

Re-presenting as rows correspond to image strips (left→right) and columns correspond to top→bottom positions:

| Strip | 1 | 2 | 3 | 4 | 5 | 6 | 7 | 8 | 9 | 10 | 11 | 12 | 13 |
|---|---|---|---|---|---|---|---|---|---|---|---|---|---|
| 1 | 0.64 | 0.64 | 0.66 | 0.64 | 0.63 | 1.92 | 1.64 | 1.56 | 1.52 | 0.66 | 2.04 | 1.64 | 1.51 |
| 2 | 0.07 | 0.06 | 0.00 | 0.08 | 0.07 | 0.15 | 0.10 | 0.33 | 0.13 | 0.08 | 0.16 | 0.15 | 0.13 |
| 3 | 0.08 | 0.08 | 0.12 | 0.00 | 0.07 | 0.36 | 0.22 | 0.22 | 0.37 | 0.13 | 0.36 | 0.30 | 0.24 |
| 4 | 0.16 | 0.12 | 0.30 | 0.08 | 0.11 | 0.26 | 0.21 | 0.20 | 0.35 | 0.44 | 0.51 | 0.50 | 0.17 |
| 5 | 0.55 | 0.58 | 0.63 | 0.43 | 0.51 | 1.86 | 1.32 | 0.99 | 1.11 | 0.61 | 1.86 | 1.42 | 1.22 |
| 6 | 0.24 | 0.15 | 0.07 | 0.07 | 0.07 | 0.13 | 0.11 | 0.10 | 0.10 | 0.08 | 1.11 | 0.10 | 0.00 |
| 7 | 0.07 | 0.08 | 0.61 | 0.07 | 0.07 | 0.13 | 0.83 | 0.12 | 0.08 | 0.08 | 0.10 | 0.10 | 0.08 |
| 8 |  |  |  |  |  |  |  |  |  |  |  |  |  |
| 9 |  |  |  |  |  |  |  |  |  |  |  |  |  |
| 10 |  |  |  |  |  |  |  |  |  |  |  |  |  |
| 11 | 0.07 | 0.07 | 0.59 | 0.08 | 0.07 | 0.16 | 0.63 | 0.12 | 0.11 | 0.08 | 0.14 | 0.12 | 0.11 |
| 12 | 0.07 | 0.07 | 0.00 | 0.08 | 0.08 | 0.18 | 0.10 | 0.12 | 0.12 | 0.08 | 0.18 | 0.16 | 0.11 |
| 13 | 0.07 | 0.07 | 0.00 | 0.08 | 0.07 | 0.17 | 0.00 | 0.13 | 0.15 | 0.08 | 0.18 | 0.17 | 0.11 |
| 14 | 0.06 | 0.06 | 0.08 | 0.08 | 0.08 | 0.16 | 0.00 | 0.15 | 0.10 | 0.07 | 0.10 | 0.10 | 0.13 |
| 15 | 0.57 | 0.64 | 0.74 | 0.71 | 0.68 | 1.91 | 1.43 | 1.37 | 1.60 | 0.69 | 1.88 | 1.54 | 1.47 |
| 16 | 0.65 | 0.65 | 0.68 | 0.67 | 0.63 | 1.97 | 1.58 | 1.35 | 1.50 | 0.67 | 1.95 | 1.44 | 1.43 |
| 17 | 0.65 | 0.70 | 0.70 | 0.70 | 0.68 | 1.95 | 1.41 | 1.61 | 1.71 | 0.68 | 2.06 | 1.65 | 1.44 |
| 18 | 0.57 | 0.60 | 0.62 | 0.47 | 0.57 | 1.87 | 1.41 | 1.26 | 1.30 | 0.66 | 1.26 | 1.34 | 1.38 |

| 12.50 | 25.00 | >50 | 12.50 | 6.25 | >50 | 25.00 | 25.00 | >50 | >50 | 1.56 | >50 | 0.30 | >50 | >50 | 12.50 | >50 | >50 | >50 | >50 | 25.00 | >50 |
|---|---|---|---|---|---|---|---|---|---|---|---|---|---|---|---|---|---|---|---|---|---|
| >50 | >50 | >50 | >50 | >50 | >50 | >50 | >50 | >50 | >50 | >50 | >50 | 12.50 | >50 | >50 | >50 | >50 | >50 | >50 | >50 | >50 | >50 |
| 0.81 | 1.94 |  |  | 1.99 |  |  |  |  |  | 1.53 | 1.43 | 1.30 |  |  |  |  |  | 1.64 | 1.70 |  |  |
| 0.13 | 1.69 |  |  | 0.04 |  |  |  |  |  | 0.21 | 0.04 | 0.04 |  |  |  |  |  | 0.05 | 0.05 |  |  |
| 0.80 | 0.10 |  |  | 0.05 |  |  |  |  |  | 0.18 | 0.07 | 0.10 |  |  |  |  |  | 0.00 | 0.00 |  |  |
| 0.16 | 0.07 |  |  | 0.04 |  |  |  |  |  | 0.19 | 0.04 | 0.04 |  |  |  |  |  | 0.05 | 0.05 |  |  |
| 0.85 | 0.19 |  |  | 0.05 |  |  |  |  |  | 0.37 | 0.05 | 0.05 |  |  |  |  |  | 0.05 | 0.05 |  |  |
| 0.08 | 1.02 |  |  | 0.05 |  |  |  |  |  | 0.18 | 0.04 | 0.05 |  |  |  |  |  | 0.05 | 0.05 |  |  |
| 0.16 | 0.08 |  |  | 0.00 |  |  |  |  |  | 0.56 | 0.22 | 0.25 |  |  |  |  |  | 0.11 | 0.66 |  |  |
| 0.32 | 0.08 |  |  | 0.00 |  |  |  |  |  | 0.60 | 0.08 | 0.09 |  |  |  |  |  | 0.00 | 0.00 |  |  |
| 0.16 | 0.07 |  |  | 0.06 |  |  |  |  |  | 0.14 | 0.07 | 0.07 |  |  |  |  |  | 0.07 | 0.08 |  |  |
| 0.13 | 0.44 |  |  | 0.04 |  |  |  |  |  | 0.20 | 0.05 | 0.04 |  |  |  |  |  | 0.04 | 0.04 |  |  |
| 0.18 | 0.08 |  |  | 0.05 |  |  |  |  |  | 0.26 | 0.04 | 0.04 |  |  |  |  |  | 0.05 | 0.05 |  |  |
| 0.31 | 0.22 |  |  | 0.24 |  |  |  |  |  | 1.54 | 0.12 | 0.17 |  |  |  |  |  | 0.18 | 0.36 |  |  |

| 0.14 | 0.07 |   |   | 0.07 |   |   |   | 0.55 | 0.07 | 0.06 |   |   |   | 0.08 | 0.08 |
|---|---|---|---|---|---|---|---|---|---|---|---|---|---|---|---|
| 0.14 | 0.07 |   |   | 0.07 |   |   |   | 0.55 | 0.07 | 0.06 |   |   |   | 0.06 | 0.06 |
| 0.28 | 0.07 |   |   | 0.08 |   |   |   | 0.58 | 0.58 | 0.62 |   |   |   | 0.10 | 0.71 |
| 0.10 | 0.07 |   |   | 0.07 |   |   |   | 0.56 | 0.08 | 0.08 |   |   |   | 0.08 | 0.08 |
| 0.11 | 0.15 |   |   | 0.08 |   |   |   | 0.55 | 0.07 | 0.08 |   |   |   | 0.08 | 0.07 |
| 0.27 | 0.17 |   |   | 0.22 |   |   |   | 1.83 | 0.13 | 0.21 |   |   |   | 0.10 | 0.18 |
| 0.24 | 0.17 |   |   | 0.15 |   |   |   | 1.99 | 0.00 | 0.10 |   |   |   | 0.10 | 0.17 |
| 0.23 | 0.80 |   |   | 0.16 |   |   |   | 1.24 | 0.00 | 0.14 |   |   |   | 0.43 | 0.14 |
| 0.32 | 0.13 |   |   | 0.15 |   |   |   | 1.30 | 0.12 | 0.16 |   |   |   | 0.14 | 0.17 |
| 0.30 | 0.08 |   |   | 0.08 |   |   |   | 0.57 | 0.08 | 0.08 |   |   |   | 0.07 | 0.07 |
| 0.55 | 0.18 |   |   | 0.23 |   |   |   | 2.00 | 0.18 | 0.21 |   |   |   | 0.21 | 0.40 |
| 0.42 | 0.12 |   |   | 0.17 |   |   |   | 1.61 | 0.19 | 0.18 |   |   |   | 0.16 | 0.19 |
| 0.10 | 0.11 |   |   | 0.15 |   |   |   | 0.99 | 0.15 | 0.16 |   |   |   | 0.22 | 0.16 |

FIG. 12K

| | | | | | | | | | | | | | | | | | | | | | |
|---|---|---|---|---|---|---|---|---|---|---|---|---|---|---|---|---|---|---|---|---|---|
| >50 | 25.00 | >50 | >50 | >50 | >50 | 0.20 | >50 | 0.78 | >50 | 12.50 | >50 | >50 | >50 | 0.20 | >50 | 12.50 | >50 | 0.20 | >50 | 1.56 | >50 |
| 25.00 | >50 | >50 | 3.13 | >50 | >50 | >50 | 12.50 | >50 | >50 | >50 | >50 | 1.56 | 0.39 | >50 | 25.00 | >50 | 3.13 | 0.20 | >50 | >50 | >50 |
| >50 | >50 | >50 | 6.25 | >50 | 12.50 | >50 | 0.20 | 0.39 | >50 | >50 | >50 | 0.20 | 0.20 | >50 | 25.00 | 12.50 | >50 | >50 | >50 | >50 | >50 |
| >50 | 12.50 | >50 | >50 | >50 | 25.00 | >50 | 0.39 | 0.20 | >50 | >50 | 0.78 | >50 | 12.50 | >50 | >50 | >50 | >50 | >50 | >50 | >50 | >50 |
| 6.25 | 6.25 | >50 | >50 | >50 | >50 | 3.13 | 0.20 | 3.13 | 25.00 | >50 | 0.20 | >50 | 0.78 | 25.00 | 0.20 | >50 | >50 | >50 | >50 | >50 | >50 |
| >50 | >50 | >50 | >50 | >50 | 12.50 | 0.39 | >50 | >50 | 0.39 | 1.56 | >50 | 0.39 | >50 | >50 | >50 | >50 | >50 | >50 | >50 |
| >50 | >50 | >50 | >50 | >50 | 6.25 | 0.39 | >50 | >50 | 0.20 | >50 | 0.78 | 25.00 | 0.78 | >50 | >50 | >50 | >50 | >50 |
| 3.13 | 6.25 | >50 | >50 | >50 | >50 | 25.00 | 1.56 | >50 | 25.00 | >50 | >50 | >50 | 0.78 | 25.00 | >50 | >50 | >50 | >50 | >50 |
| >50 | >50 | >50 | 0.39 | >50 | >50 | 25.00 | 0.20 | >50 | >50 | >50 | 0.20 | >50 | >50 | >50 | >50 | >50 | >50 | >50 | >50 |
| >50 | >50 | >50 | 0.20 | >50 | >50 | 6.25 | >50 | >50 | >50 | >50 | 12.50 | >50 | >50 | >50 | >50 | >50 | >50 | >50 | >50 |
| 12.50 | 6.25 | >50 | 12.50 | >50 | 12.50 | 12.50 | >50 | >50 | >50 | 25.00 | >50 | >50 | >50 | >50 | >50 | >50 | >50 | >50 | >50 |
| 25.00 | >50 | >50 | 3.13 | >50 | >50 | >50 | 12.50 | >50 | >50 | >50 | >50 | >50 | >50 | >50 | >50 | >50 | >50 | >50 | >50 |
| 3.13 | 6.25 | >50 | 0.78 | >50 | >50 | 6.25 | >50 | >50 | 25.00 | >50 | >50 | >50 | 12.50 | >50 | >50 | >50 | >50 | >50 | >50 |
| 6.25 | 12.50 | >50 | >50 | >50 | >50 | 12.50 | >50 | >50 | >50 | >50 | >50 | >50 | >50 | >50 | >50 | >50 | >50 | >50 | >50 |

Ab 98 →

| 25.00 | >50 | 1.65 | 0.04 | 0.07 | 0.04 | 0.04 | 0.04 | 0.38 | 0.08 | 0.07 | 0.05 | 0.04 | 0.18 |
| 12.50 | >50 |      |      |      |      |      |      |      |      |      |      |      |      |
| >50   | >50 |      |      |      |      |      |      |      |      |      |      |      |      |
| >50   | >50 |      |      |      |      |      |      |      |      |      |      |      |      |
| >50   | >50 |      |      |      |      |      |      |      |      |      |      |      |      |
| >50   | >50 | 1.40 | 1.74 | 0.00 | 0.07 | 0.00 | 0.85 | 0.08 | 0.00 | 0.06 | 0.07 | 0.07 | 0.20 |
| 0.30  | >50 | 1.87 | 0.10 | 0.00 | 0.06 | 0.10 | 0.07 | 0.00 | 0.08 | 0.07 | 0.24 | 0.08 | 0.18 |
| >50   | 6.25 | 1.61 | 1.81 | 1.51 | 0.58 | 2.08 | 1.65 | 0.34 | 0.43 | 0.45 | 0.56 | 0.77 | 0.96 |
| 0.30  | >50 |      |      |      |      |      |      |      |      |      |      |      |      |
| 12.50 | >50 | 0.80 | 0.08 | 0.00 | 0.07 | 0.08 | 0.07 | 0.08 | 0.08 | 0.08 | 0.00 | 0.07 | 0.12 |
| >50   | >50 |      |      |      |      |      |      |      |      |      |      |      |      |
| >50   | >50 | 1.43 | 0.36 | 0.30 | 0.22 | 0.52 | 0.24 | 0.66 | 0.69 | 0.21 | 0.33 | 0.32 | 1.40 |
| >50   | >50 |      |      |      |      |      |      |      |      |      |      |      |      |
| 6.25  | 25.00 | 1.67 | 0.04 | 0.05 | 0.04 | 0.04 | 0.04 | 0.07 | 0.08 | 0.05 | 0.05 | 0.04 | 0.00 |
| 0.78  | >50 |      |      |      |      |      |      |      |      |      |      |      |      |
| >50   | >50 |      |      |      |      |      |      |      |      |      |      |      |      |
| >50   | >50 |      |      |      |      |      |      |      |      |      |      |      |      |
| >50   | 0.30 | 1.80 | 0.52 | 0.48 | 0.43 | 0.51 | 0.53 | 0.65 | 0.69 | 0.47 | 0.52 | 0.51 | 2.22 |
| 0.20  | >50 |      |      |      |      |      |      |      |      |      |      |      |      |
| >50   | >50 |      |      |      |      |      |      |      |      |      |      |      |      |
| >50   | 6.25 |      |      |      |      |      |      |      |      |      |      |      |      |
| 6.25  | >50 |      |      |      |      |      |      |      |      |      |      |      |      |
| >50   |     |      |      |      |      |      |      |      |      |      |      |      |      |

FIG. 12L

| | | | | | | | | | | | | | |
|---|---|---|---|---|---|---|---|---|---|---|---|---|---|
| 0.07 | | | 0.07 | 0.07 | 0.33 | | 0.07 | | 0.55 | | 0.07 | | 0.63 |
| 0.06 | | | 0.08 | 0.06 | 0.26 | | 0.07 | | 0.56 | | 0.06 | | 0.65 |
| 0.73 | | | 0.08 | 0.07 | 0.58 | | 0.08 | | 0.63 | | 0.07 | | 0.61 |
| 0.08 | | | 0.08 | 0.08 | 0.11 | | 0.07 | | 0.60 | | 0.07 | | 0.63 |
| 0.07 | | | 0.06 | 0.07 | 0.15 | | 0.07 | | 0.65 | | 0.07 | | 0.58 |
| 0.16 | | | 0.16 | 0.17 | 1.20 | | 0.18 | | 1.83 | | 0.12 | | 1.88 |
| 0.11 | | | 0.11 | 0.12 | 0.74 | | 0.12 | | 1.26 | | 0.00 | | 1.72 |
| 0.15 | | | 0.12 | 1.17 | 0.83 | | 1.17 | | 1.27 | | 0.08 | | 1.86 |
| 0.15 | | | 0.13 | 0.16 | 1.13 | | 0.14 | | 1.56 | | 0.08 | | 2.05 |
| 0.07 | | | 0.08 | 0.07 | 0.38 | | 0.08 | | 0.63 | | 0.00 | | 0.62 |
| 0.21 | | | 0.21 | 0.25 | 1.48 | | 0.24 | | 1.00 | | 0.11 | | 2.18 |
| 0.18 | | | 0.15 | 0.17 | 0.00 | | 0.14 | | 1.20 | | 0.10 | | 1.96 |
| 0.14 | | | 0.13 | 0.15 | 0.76 | | 0.15 | | 1.15 | | 0.08 | | 1.83 |

FIG. 12M

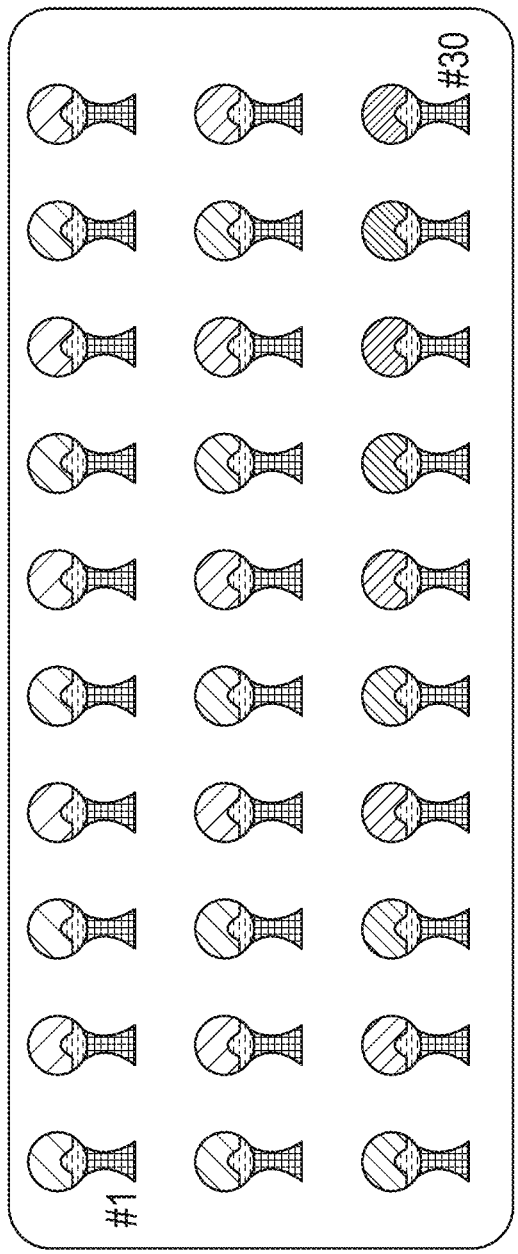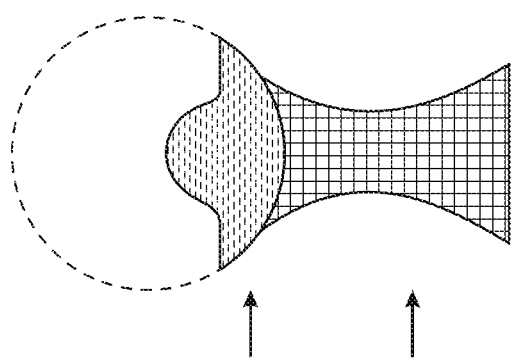
FIG. 13A

FIG. 13C

| | | | | | | | | | | | | | | | | | | | | | | | | | | |
|---|---|---|---|---|---|---|---|---|---|---|---|---|---|---|---|---|---|---|---|---|---|---|---|---|---|---|
| 17 | 1.98 | 0.06 | 0.06 | 0.04 | 0.04 | 0.10 | 0.08 | 0.06 | 0.04 | 0.05 | 0.05 | 0.11 | 0.19 | 0.15 | 0.13 | 0.09 | 0.08 | 1.25 | 0.09 | 0.13 | 0.07 | 0.08 | 0.00 | 0.07 | 0.08 | - |
| 19 | 1.81 | 0.04 | 0.08 | 0.01 | 0.04 | 0.06 | 0.08 | 0.10 | 0.07 | 0.04 | 0.04 | 0.15 | 0.53 | 0.29 | 0.17 | 0.08 | 0.11 | 0.17 | 0.00 | 0.20 | 0.08 | 0.09 | 0.00 | 0.08 | 0.08 | - |
| 20 | 1.80 | 0.04 | 0.07 | 0.05 | 0.05 | 0.25 | 0.10 | 0.09 | 0.06 | 0.04 | 0.05 | 0.15 | 1.65 | 0.15 | 0.17 | 0.08 | 0.11 | 0.18 | 0.11 | 0.17 | 0.08 | 0.08 | 0.10 | 0.08 | 0.08 | |
| 21 | 1.94 | 0.09 | 0.09 | 0.05 | 0.25 | 0.17 | 0.10 | 0.10 | 0.04 | 0.08 | 0.06 | 0.12 | 0.12 | 0.15 | 0.14 | 0.08 | 0.13 | 0.13 | 0.10 | 0.14 | 0.08 | 0.08 | 0.10 | 0.08 | 0.07 | - |
| 26 | 1.02 | 0.54 | 0.97 | 1.00 | 0.25 | 1.42 | 0.20 | 0.14 | 0.18 | 0.06 | 0.06 | 0.30 | 0.21 | 0.39 | 0.15 | 0.13 | 0.37 | 0.22 | 0.22 | 0.36 | 0.08 | 0.09 | 0.09 | 0.07 | 0.08 | H |
| 28 | 1.91 | 0.83 | 1.91 | 0.80 | 0.30 | 1.00 | 0.12 | 0.11 | 0.20 | 0.08 | 0.07 | 0.25 | 0.17 | 0.50 | 0.36 | 0.44 | 0.35 | 0.20 | 0.21 | 0.26 | 0.07 | 0.09 | 0.12 | 0.08 | 0.07 | - |
| 31 | 0.91 | 0.10 | 0.10 | 0.30 | 0.80 | 0.80 | 0.31 | 0.17 | 0.09 | 0.05 | 0.14 | 0.11 | 0.09 | 0.10 | 0.51 | 0.13 | 0.10 | 0.10 | 0.10 | 0.11 | 0.08 | 0.08 | 0.12 | 0.08 | 0.08 | - |
| 33 | 1.80 | 0.69 | 0.83 | 0.08 | 0.08 | 0.80 | 0.08 | 0.08 | 0.08 | 0.08 | 0.09 | 0.09 | 0.08 | 0.10 | 0.11 | 0.08 | 0.08 | 0.12 | 0.21 | 0.13 | 0.08 | 0.08 | 0.30 | 0.07 | 0.08 | H |
| 39 | 1.77 | 0.04 | 0.10 | 0.30 | 0.08 | 0.00 | 0.00 | 0.08 | 0.05 | 0.14 | 0.09 | 0.12 | 0.08 | 0.10 | 0.10 | 0.08 | 0.08 | 0.12 | 0.83 | 0.16 | 0.07 | 0.07 | 0.61 | 0.07 | 0.07 | H |
| 41 | 1.09 | 0.11 | 0.10 | 0.08 | 0.00 | 0.42 | 0.00 | 0.05 | 0.08 | 0.09 | 0.08 | 0.22 | 0.11 | 0.12 | 0.14 | 0.08 | 0.11 | 0.13 | 0.63 | 0.17 | 0.07 | 0.07 | 0.59 | 0.08 | 0.07 | - |
| 42 | 1.81 | 1.90 | 0.10 | 0.10 | 0.07 | 0.09 | 0.08 | 0.08 | 0.09 | 0.18 | 0.09 | 0.12 | 0.13 | 0.17 | 0.19 | 0.07 | 0.15 | 0.15 | 0.09 | 0.17 | 0.08 | 0.08 | 0.09 | 0.07 | 0.07 | - |
| 49 | 2.00 | 1.96 | 0.10 | 0.10 | 0.07 | 0.10 | 0.07 | 0.14 | 0.09 | 0.13 | 0.18 | 0.30 | 0.19 | 0.42 | 0.55 | 0.30 | 0.29 | 0.80 | 0.24 | 0.16 | 0.08 | 0.08 | 0.08 | 0.06 | 0.07 | - |
| 50 | 0.81 | 0.13 | 0.30 | 0.32 | 0.15 | 0.10 | 0.16 | 0.09 | 0.09 | 0.44 | 0.08 | 0.31 | 0.22 | 0.12 | 0.18 | 0.08 | 0.13 | 0.12 | 0.12 | 0.27 | 0.11 | 0.10 | 0.28 | 0.14 | 0.17 | H |
| 64 | 1.94 | 0.10 | 0.15 | 0.07 | 0.07 | 0.85 | 0.08 | 0.32 | 0.07 | 0.07 | 0.04 | 0.22 | 0.11 | 0.19 | 0.18 | 0.08 | 0.12 | 0.09 | 0.09 | 0.17 | 0.07 | 0.08 | 0.09 | 0.07 | 0.07 | - |
| 66 | 1.48 | 0.04 | 0.07 | 0.01 | 0.15 | 1.02 | 0.22 | 0.08 | 0.07 | 0.05 | 0.04 | 0.12 | 0.15 | 0.16 | 0.21 | 0.07 | 0.16 | 0.14 | 0.08 | 0.13 | 0.08 | 0.08 | 0.08 | 0.07 | 0.08 | H |
| 72 | 1.30 | 0.04 | 0.10 | 0.05 | 0.05 | 0.04 | 0.25 | 0.08 | 0.08 | 0.05 | 0.05 | 0.25 | 0.16 | 0.16 | 0.18 | 0.08 | 0.17 | 0.34 | 0.08 | 0.21 | 0.07 | 0.08 | 0.58 | 0.06 | 0.08 | H |
| 73 | 1.70 | 0.05 | 0.09 | 0.05 | 0.05 | 0.05 | 0.65 | 0.07 | 0.07 | 0.04 | 0.05 | 0.65 | 0.16 | 0.19 | 0.17 | 0.08 | 0.15 | 0.34 | 0.17 | 0.18 | 0.07 | 0.08 | 0.62 | 0.06 | 0.08 | H |
| 73 | 1.71 | 0.05 | 0.08 | 0.01 | 0.91 | 0.05 | 0.63 | 0.08 | 0.07 | 0.05 | 0.04 | 0.23 | 0.13 | 0.13 | 0.28 | 0.07 | 0.15 | 0.34 | 0.12 | 0.16 | 0.08 | 0.08 | 0.71 | 0.06 | 0.08 | H |
| 75 | 1.65 | 0.04 | 0.07 | 0.01 | 0.65 | 0.04 | 0.38 | 0.08 | 0.07 | 0.05 | 0.05 | 0.18 | 0.14 | 0.18 | 0.21 | 0.07 | 0.15 | 0.15 | 0.11 | 0.16 | 0.08 | 0.08 | 0.79 | 0.06 | 0.07 | H |

FIG. 13D

Table 1 (top, header cells marked "-" for last three columns):

| 81 | 1.49 | 1.74 | 0.09 | 0.07 | 0.85 | 0.08 | 0.09 | 0.06 | 0.07 | 0.20 | 0.13 | 0.15 | 0.08 | 0.13 | 0.12 | 0.11 | 0.16 | 0.06 | 0.08 | 0.08 | 0.07 |
|---|---|---|---|---|---|---|---|---|---|---|---|---|---|---|---|---|---|---|---|---|---|
| 88 | 1.87 | 0.00 | 0.09 | 0.06 | 0.07 | 0.09 | 0.08 | 0.07 | 0.24 | 0.18 | 0.15 | 0.17 | 0.25 | 0.15 | 0.12 | 0.12 | 0.17 | 0.07 | 0.07 | 0.06 | 0.07 |
| 89 | 0.80 | 0.08 | 0.09 | 0.07 | 0.08 | 0.08 | 0.09 | 0.07 | 0.12 | 0.14 | 0.24 | 0.08 | 0.14 | 1.17 | 0.18 | 0.12 | 0.18 | 0.07 | 0.08 | 0.07 | 0.07 |

Table 2 (Head):

| 11 | 1.88 | 0.53 | 0.06 | 0.06 | 0.55 | 0.24 | 0.58 | 0.61 | 0.17 | 0.40 | 0.06 | 1.63 | 0.15 | 0.11 | 0.39 | 0.09 | 0.26 | 1.50 | 0.28 | 0.96 | 0.13 | 0.40 | 0.60 | 0.59 | 0.63 |
|---|---|---|---|---|---|---|---|---|---|---|---|---|---|---|---|---|---|---|---|---|---|---|---|---|---|
| 18 | 1.65 | 0.51 | 0.41 | 0.50 | 0.50 | 0.30 | 0.71 | 0.63 | 0.18 | 0.40 | 0.09 | 1.79 | 0.27 | 0.43 | 0.74 | 0.08 | 1.30 | 1.78 | 0.89 | 1.18 | 0.34 | 0.52 | 0.61 | 0.54 | 0.59 |
| 30 | 1.44 | 0.11 | 1.79 | 0.96 | 2.08 | 0.11 | 0.61 | 0.65 | 1.08 | 1.21 | 0.97 | 1.40 | 1.22 | 0.42 | 1.86 | 0.51 | 1.11 | 0.96 | 1.32 | 1.86 | 0.51 | 0.43 | 0.63 | 0.58 | 0.55 |
| 43 | 1.61 | 1.82 | 1.57 | 0.88 | 2.49 | 1.45 | 0.70 | 0.74 | 0.71 | 1.29 | 1.02 | 1.33 | 1.47 | 1.51 | 1.88 | 0.59 | 1.60 | 1.37 | 1.43 | 1.91 | 0.68 | 0.71 | 0.74 | 0.54 | 0.59 |
| 46 | 1.96 | 0.84 | 1.50 | 1.12 | 1.69 | 0.17 | 0.68 | 0.77 | 0.96 | 1.27 | 1.07 | 1.74 | 1.44 | 1.65 | 2.06 | 0.58 | 1.71 | 1.61 | 1.41 | 1.95 | 0.68 | 0.70 | 0.70 | 0.26 | 0.33 |
| 86 | 1.60 | 1.81 | 1.51 | 0.58 | 2.08 | 1.65 | 0.34 | 0.43 | 0.45 | 0.56 | 0.77 | 0.96 | 0.76 | 0.90 | 1.48 | 0.38 | 1.13 | 0.60 | 0.74 | 1.29 | 0.15 | 0.11 | 0.58 | 0.26 | 0.63 |
| 98 | 1.80 | 0.52 | 0.18 | 0.48 | 0.50 | 0.53 | 0.65 | 0.69 | 0.47 | 0.52 | 0.51 | 2.22 | 1.83 | 1.96 | 2.13 | 0.52 | 2.05 | 1.86 | 1.72 | 1.88 | 0.58 | 0.63 | 0.61 | 0.55 | 0.55 |

Table 3 (Stem):

| 12 | 1.64 | 0.27 | 0.21 | 0.25 | 0.42 | 0.26 | 0.55 | 0.62 | 0.19 | 0.20 | 0.36 | 1.29 | 1.47 | 1.55 | 1.87 | 0.52 | 1.42 | 1.45 | 1.39 | 1.84 | 0.58 | 0.56 | 0.62 | 0.58 | 0.54 |
|---|---|---|---|---|---|---|---|---|---|---|---|---|---|---|---|---|---|---|---|---|---|---|---|---|---|
| 24 | 1.70 | 0.41 | 0.40 | 0.25 | 0.50 | 0.37 | 0.62 | 0.68 | 0.30 | 0.50 | 0.42 | 1.64 | 1.51 | 1.64 | 2.04 | 0.56 | 1.52 | 1.56 | 1.64 | 1.92 | 0.63 | 0.64 | 0.66 | 0.54 | 0.54 |
| 45 | 1.63 | 1.99 | 1.76 | 0.50 | 1.50 | 1.53 | 0.64 | 0.71 | 1.31 | 1.53 | 1.24 | 1.72 | 1.43 | 1.41 | 1.95 | 0.57 | 1.50 | 1.35 | 1.58 | 1.97 | 0.63 | 0.67 | 0.68 | 0.65 | 0.53 |
| 47 | 1.39 | 0.58 | 1.84 | 1.29 | 2.13 | 0.07 | 0.67 | 0.70 | 1.43 | 0.82 | 1.17 | 1.56 | 1.38 | 1.31 | 1.96 | 0.56 | 1.30 | 1.35 | 1.41 | 1.87 | 0.57 | 0.47 | 0.60 | 0.60 | 0.53 |
| 61 | 1.53 | 0.21 | 0.18 | 0.19 | 0.30 | 0.13 | 0.56 | 0.60 | 0.20 | 0.07 | 0.26 | 1.54 | 0.99 | 1.60 | 2.00 | 0.57 | 1.30 | 1.21 | 1.33 | 1.83 | 0.55 | 0.56 | 0.62 | 0.55 | 0.53 |
| 92 | 1.43 | 0.36 | 0.30 | 0.29 | 0.52 | 0.24 | 0.66 | 0.69 | 0.21 | 0.13 | 0.32 | 1.40 | 1.15 | 1.29 | 1.99 | 0.63 | 1.56 | 1.25 | 1.26 | 1.83 | 0.65 | 0.60 | 0.63 | 0.56 | 0.55 |

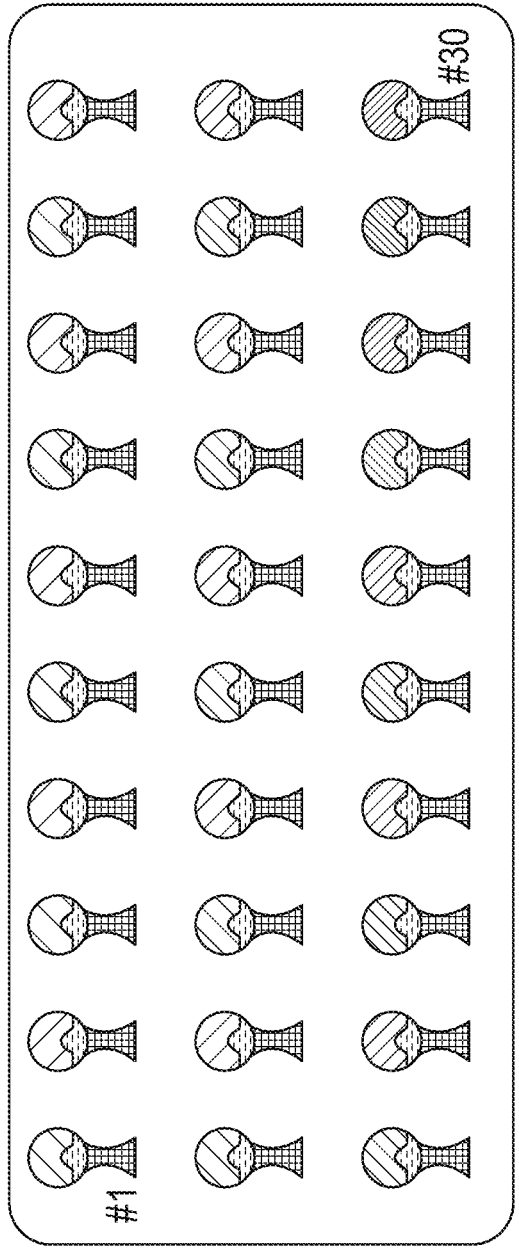

| POSITION | WT | 1 | 2 | 3 | 4 | 5 | 6 | 9 | 10 | 11 | 12 | 14 | 15 | 16 | 17 | 22 | 23 | 24 | 25 | 26 | 28 | 29 | 30 |
|---|---|---|---|---|---|---|---|---|---|---|---|---|---|---|---|---|---|---|---|---|---|---|---|
| | | | | | | | | | | | MUTANTS | | | | | | | | | | | | |
| 1 | N | Y | M | K | Q | V | V | V | R | T | I | V | A | V | V | V | S | V | L | R | V | F | F |
| 2 | T | T | V | R | R | R | R | K | V | G | T | M | K | C | S | V | Q | R | R | R | D | S | V |
| 3 | T | T | V | G | G | T | R | R | V | K | L | N | 3 | S | N | L | T | Z | N | I | Y | K | R |
| 4 | A | A | K | D | A | K | F | T | W | R | K | 4 | R | I | L | T | K | R | T | Y | S | W | K |
| 5 | W | W | F | P | L | M | H | H | M | C | T | T | N | 3 | K | L | R | K | N | T | K | K | W |
| 6 | R | R | S | T | D | N | E | N | E | G | S | Y | G | D | R | K | F | R | K | G | T | T | M |
| 7 | S | S | G | D | A | T | R | V | G | D | A | G | P | G | Q | E | T | N | T | N | N | G | N |
| 8 | S | S | P | R | G | P | W | R | P | R | S | W | V | D | K | G | H | S | G | T | T | A | R |
| 9 | T | T | V | C | M | 9 | V | A | I | Y | R | Q | R | A | D | T | S | S | A | E | G | N | H |
| 10 | H | H | G | A | T | P | A | S | G | P | S | S | S | R | A | S | R | V | N | A | A | A | Q |
| 11 | L | L | V | N | S | D | L | P | L | S | R | L | F | T | P | – | Q | Q | N | P | N | Q | P |
| 12 | N | N | R | G | P | R | H | V | P | Q | L | F | A | P | T | A | P | W | T | P | T | K | P |
| 13 | N | N | D | R | K | T | T | R | F | T | T | Q | T | K | R | P | K | T | K | L | P | P | Q |
| 14 | K | K | N | E | D | A | I | R | T | F | A | L | Q | L | F | K | R | P | L | T | L | T | G |
| 15 | F | F | A | G | G | Q | S | T | R | A | Q | R | A | E | A | N | E | R | R | H | R | H | R |
| 16 | A | A | Q | N | L | V | R | I | R | R | R | Y | R | A | N | P | H | F | S | W | R | M | M |
| 17 | Q | Q | R | L | P | S | P | – | S | P | T | S | Y | P | P | L | S | Y | T | R | L | R | C |
| | | | | | | | | | | | | | | | | | F | S | S | P | K | F | F |
| | | | | | | | | | | | | | | | | | T | T | Q | G | L | T | I |
| | | | | | | | | | | | | | | | | | V | V | 00 | R | C | N | T |
| | | | | | | | | | | | | | | | | | M | M | Q | K | I | E | E |
| | | | | | | | | | | | | | | | | | P | P | M | C | T | P | A |
| | | | | | | | | | | | | | | | | | F | F | P | Y | S | F | A |
| | | | | | | | | | | | | | | | | | A | A | F | Y | T | F | A |

FIG. 14A

| | | | | | | | | | | | | | | | | | | | | |
|---|---|---|---|---|---|---|---|---|---|---|---|---|---|---|---|---|---|---|---|---|
| 17 | 1.98 | 0.06 | 0.04 | 0.04 | 0.10 | 0.08 | 0.06 | 0.04 | 0.05 | 0.05 | 0.11 | 0.19 | 0.15 | 0.13 | 0.09 | 0.08 | 1.25 | 0.09 | 0.13 | 0.07 | 0.08 | 0.00 | 0.07 | 0.08 | - |
| 19 | 1.81 | 0.04 | 0.01 | 0.05 | 0.06 | 0.06 | 0.09 | 0.07 | 0.04 | 0.05 | 0.15 | 0.29 | 0.17 | 0.17 | 0.08 | 0.11 | 0.17 | 0.00 | 0.20 | 0.08 | 0.09 | 0.00 | 0.08 | 0.08 | - |
| 20 | 1.80 | 0.04 | 0.05 | 0.05 | 0.25 | 0.10 | 0.09 | 0.06 | 0.04 | 0.05 | 0.15 | 0.15 | 0.15 | 0.17 | 0.08 | 0.11 | 0.18 | 0.11 | 0.17 | 0.08 | 0.08 | 0.10 | 0.08 | 0.08 | |
| 21 | 1.94 | 0.07 | 0.09 | 0.09 | 0.17 | 0.10 | 0.17 | 0.07 | 0.08 | 0.06 | 0.15 | 1.65 | 0.15 | 0.17 | 0.12 | 0.11 | 0.13 | 0.10 | 0.14 | 0.08 | 0.08 | 0.09 | 0.08 | 0.07 | - |
| 26 | 1.02 | 0.09 | 0.10 | 1.00 | 1.42 | 0.08 | 0.20 | 0.14 | 0.18 | 0.06 | 0.12 | 0.12 | 0.14 | 0.15 | 0.12 | 0.13 | 0.22 | 0.22 | 0.14 | 0.08 | 0.08 | 0.09 | 0.07 | 0.08 | H |
| 28 | 1.91 | 0.54 | 0.25 | 0.80 | 1.00 | 0.07 | 0.17 | 0.11 | 0.11 | 0.06 | 0.30 | 0.39 | 0.36 | 0.51 | 0.37 | 0.22 | 0.13 | 0.36 | 0.07 | 0.08 | 0.07 | 0.12 | 0.08 | 0.08 | - |
| 31 | 0.91 | 0.83 | 0.30 | 0.08 | 0.08 | 0.08 | 0.20 | 0.11 | 0.20 | 0.18 | 0.25 | 0.50 | 0.39 | 0.44 | 0.35 | 0.20 | 0.22 | 0.26 | 0.11 | 0.09 | 0.08 | 0.30 | 0.12 | 0.16 | - |
| 33 | 1.80 | 0.10 | 0.08 | 0.08 | 0.08 | 0.08 | 0.08 | 0.09 | 0.08 | 0.08 | 0.11 | 0.10 | 0.10 | 0.11 | 0.10 | 0.10 | 0.10 | 0.21 | 0.13 | 0.08 | 0.07 | 0.07 | 0.15 | 0.24 | H |
| 39 | 1.77 | 0.04 | 0.00 | 0.05 | 0.00 | 0.07 | 0.17 | 0.05 | 0.14 | 0.05 | 0.09 | 0.09 | 0.10 | 0.10 | 0.08 | 0.08 | 0.12 | 0.11 | 0.13 | 0.07 | 0.07 | 0.61 | 0.08 | 0.07 | H |
| 41 | 1.09 | 0.11 | 0.08 | 0.04 | 0.42 | 0.08 | 0.08 | 0.08 | 0.09 | 0.08 | 0.12 | 0.08 | 0.10 | 0.10 | 0.08 | 0.11 | 0.12 | 0.83 | 0.16 | 0.07 | 0.07 | 0.59 | 0.07 | 0.07 | H |
| 42 | 1.81 | 0.10 | 0.07 | 0.09 | 1.43 | 0.08 | 0.08 | 0.12 | 0.14 | 0.08 | 0.30 | 0.17 | 0.12 | 0.14 | 0.11 | 0.15 | 0.13 | 0.63 | 0.17 | 0.08 | 0.07 | 0.09 | 0.07 | 0.07 | - |
| 49 | 2.00 | 0.10 | 0.07 | 0.10 | 1.65 | 0.07 | 0.09 | 0.08 | 0.09 | 0.09 | 0.34 | 0.19 | 0.17 | 0.18 | 0.15 | 0.15 | 0.15 | 0.09 | 0.16 | 0.07 | 0.07 | 0.08 | 0.06 | 0.07 | - |
| 50 | 1.96 | 0.10 | 0.15 | 0.85 | 0.08 | 0.15 | 0.32 | 0.13 | 0.18 | 0.09 | 0.31 | 0.42 | 0.19 | 0.19 | 0.10 | 0.29 | 0.32 | 0.24 | 0.27 | 0.11 | 0.15 | 0.08 | 0.14 | 0.17 | - |
| 64 | 0.81 | 0.30 | 0.07 | 1.02 | 0.08 | 0.08 | 0.08 | 0.44 | 0.13 | 0.18 | 0.22 | 0.11 | 0.12 | 0.18 | 0.13 | 0.80 | 0.13 | 0.12 | 0.17 | 0.10 | 0.15 | 0.28 | 0.07 | 0.07 | H |
| 66 | 1.94 | 0.10 | 0.01 | 0.15 | 0.04 | 0.08 | 0.22 | 0.05 | 0.08 | 0.04 | 0.12 | 0.15 | 0.19 | 0.21 | 0.12 | 0.09 | 0.09 | 0.09 | 0.17 | 0.07 | 0.08 | 0.07 | 0.07 | 0.07 | H |
| 72 | 1.48 | 0.07 | 0.01 | 0.05 | 0.05 | 0.07 | 0.25 | 0.04 | 0.05 | 0.05 | 0.17 | 0.16 | 0.18 | 0.08 | 0.16 | 0.14 | 0.08 | 0.08 | 0.13 | 0.08 | 0.08 | 0.58 | 0.07 | 0.08 | H |
| 73 | 1.30 | 0.09 | 0.05 | 0.05 | 0.05 | 0.08 | 0.65 | 0.05 | 0.05 | 0.05 | 0.36 | 0.16 | 0.18 | 0.21 | 0.17 | 0.34 | 0.16 | 0.08 | 0.21 | 0.07 | 0.08 | 0.62 | 0.06 | 0.08 | H |
| 72 | 1.70 | 0.08 | 0.01 | 0.91 | 0.05 | 0.08 | 0.63 | 0.04 | 0.04 | 0.04 | 0.23 | 0.19 | 0.28 | 0.08 | 0.15 | 0.34 | 0.12 | 0.17 | 0.18 | 0.08 | 0.08 | 0.71 | 0.06 | 0.08 | H |
| 73 | 1.71 | 0.08 | 0.01 | 0.05 | 0.08 | 0.08 | 0.63 | 0.05 | 0.05 | 0.05 | 0.13 | 0.17 | 0.13 | 0.28 | 0.15 | 0.34 | 0.12 | 0.12 | 0.16 | 0.08 | 0.08 | 0.74 | 0.06 | 0.08 | H |
| 75 | 1.65 | 0.07 | 0.01 | 0.65 | 0.04 | 0.07 | 0.38 | 0.05 | 0.04 | 0.04 | 0.18 | 0.18 | 0.14 | 0.21 | 0.07 | 0.15 | 0.15 | 0.11 | 0.16 | 0.08 | 0.06 | 0.79 | 0.06 | 0.07 | H |

| | | | | | | | | | | | | | | | | | | | | | | | | | | |
|---|---|---|---|---|---|---|---|---|---|---|---|---|---|---|---|---|---|---|---|---|---|---|---|---|---|---|
| | - | - | | - | H | - | - | H | H | - | - | - | - | H | H | H | H | H | | | | | | | | |
| 17 | 1.98 | 0.06 | 0.04 | 0.04 | 0.06 | 0.04 | 0.08 | 0.06 | 0.04 | 0.05 | 0.05 | 0.11 | 0.19 | 0.15 | 0.13 | 0.09 | 0.08 | 1.25 | 0.09 | 0.13 | 0.07 | 0.08 | 0.00 | 0.07 | 0.08 | - |
| 19 | 1.81 | 0.04 | 0.01 | 0.05 | 0.08 | 0.07 | 0.06 | 0.04 | 0.05 | 0.05 | 0.15 | 0.53 | 0.29 | 0.15 | 0.17 | 0.08 | 0.11 | 0.17 | 0.00 | 0.20 | 0.08 | 0.09 | 0.00 | 0.08 | 0.08 | - |
| 20 | 1.80 | 0.04 | 0.05 | 0.05 | 0.10 | 0.06 | 0.09 | 0.07 | 0.04 | 0.06 | 0.15 | 1.65 | 0.15 | 0.17 | 0.17 | 0.11 | 0.11 | 0.18 | 0.11 | 0.17 | 0.08 | 0.09 | 0.10 | 0.08 | 0.08 | |
| 21 | 1.94 | 0.97 | 0.09 | 0.25 | 0.10 | 0.07 | 0.08 | 0.06 | 0.06 | 0.06 | 0.15 | 0.12 | 0.15 | 0.15 | 0.17 | 0.08 | 0.12 | 0.13 | 0.10 | 0.14 | 0.08 | 0.08 | 0.10 | 0.08 | 0.07 | - |
| 26 | 1.02 | 1.91 | 0.54 | 1.00 | 0.17 | 0.20 | 0.07 | 0.08 | 0.18 | 0.06 | 0.12 | 0.21 | 0.14 | 0.36 | 0.15 | 0.13 | 0.37 | 0.22 | 0.14 | 0.36 | 0.08 | 0.08 | 0.09 | 0.07 | 0.08 | H |
| 28 | 0.91 | 0.10 | 0.25 | 0.80 | 1.42 | 0.11 | 0.14 | 0.20 | 0.11 | 0.06 | 0.30 | 0.39 | 0.50 | 0.51 | 0.44 | 0.36 | 0.35 | 0.22 | 0.22 | 0.26 | 0.09 | 0.08 | 0.12 | 0.11 | 0.16 | - |
| 31 | 1.80 | 0.83 | 0.30 | 0.08 | 0.08 | 0.31 | 0.11 | 0.20 | 0.08 | 0.18 | 0.25 | 0.17 | 0.10 | 0.11 | 0.13 | 0.51 | 0.10 | 0.20 | 0.21 | 0.26 | 0.08 | 0.08 | 0.30 | 0.15 | 0.24 | - |
| 33 | 1.77 | 0.04 | 0.08 | 0.08 | 0.08 | 0.17 | 0.09 | 0.08 | 0.11 | 0.05 | 0.11 | 0.09 | 0.10 | 0.10 | 0.08 | 0.22 | 0.10 | 0.10 | 0.11 | 0.13 | 0.08 | 0.07 | 0.07 | 0.07 | 0.07 | H |
| 39 | 1.09 | 0.11 | 0.10 | 0.08 | 0.00 | 0.08 | 0.05 | 0.09 | 0.12 | 0.08 | 0.09 | 0.08 | 0.10 | 0.12 | 0.08 | 0.22 | 0.12 | 0.12 | 0.83 | 0.13 | 0.07 | 0.07 | 0.61 | 0.08 | 0.07 | H |
| 41 | 1.81 | 1.90 | 0.10 | 0.42 | 0.09 | 0.08 | 0.08 | 0.08 | 0.08 | 0.09 | 0.09 | 0.08 | 0.17 | 0.14 | 0.08 | 0.30 | 0.11 | 0.13 | 0.63 | 0.16 | 0.07 | 0.08 | 0.59 | 0.07 | 0.07 | - |
| 42 | 2.00 | 1.96 | 0.10 | 0.09 | 0.07 | 0.09 | 0.12 | 0.09 | 0.09 | 0.07 | 0.31 | 0.19 | 0.19 | 0.55 | 0.07 | 0.34 | 0.15 | 0.15 | 0.09 | 0.17 | 0.07 | 0.08 | 0.09 | 0.07 | 0.07 | - |
| 49 | 0.81 | 0.30 | 0.15 | 0.85 | 0.08 | 0.16 | 0.13 | 0.18 | 0.09 | 0.18 | 0.22 | 0.42 | 0.42 | 0.19 | 0.30 | 0.32 | 0.10 | 0.29 | 0.24 | 0.27 | 0.11 | 0.10 | 0.28 | 0.14 | 0.17 | - |
| 50 | 1.94 | 1.89 | 0.30 | 1.65 | 0.08 | 0.32 | 0.08 | 0.07 | 0.13 | 0.08 | 0.12 | 0.11 | 0.12 | 0.18 | 0.08 | 0.13 | 0.12 | 0.80 | 0.12 | 0.17 | 0.10 | 0.15 | 0.28 | 0.14 | 0.17 | - |
| 64 | 1.48 | 0.04 | 0.10 | 0.07 | 0.08 | 0.08 | 0.09 | 0.07 | 0.44 | 0.04 | 0.22 | 0.15 | 0.19 | 0.21 | 0.08 | 0.12 | 0.13 | 0.09 | 0.09 | 0.17 | 0.07 | 0.07 | 0.09 | 0.07 | 0.07 | H |
| 66 | 1.30 | 0.04 | 0.05 | 0.01 | 0.22 | 0.07 | 0.09 | 0.08 | 0.05 | 0.05 | 0.25 | 0.19 | 0.18 | 0.18 | 0.08 | 0.16 | 0.12 | 0.14 | 0.08 | 0.13 | 0.07 | 0.08 | 0.58 | 0.06 | 0.08 | H |
| 72 | 1.70 | 0.05 | 0.05 | 0.01 | 0.25 | 0.08 | 0.09 | 0.08 | 0.05 | 0.05 | 0.65 | 0.16 | 0.19 | 0.21 | 0.08 | 0.17 | 0.16 | 0.34 | 0.17 | 0.21 | 0.08 | 0.08 | 0.62 | 0.06 | 0.08 | H |
| 73 | 1.71 | 0.05 | 0.01 | 0.91 | 0.65 | 0.08 | 0.08 | 0.08 | 0.04 | 0.05 | 0.63 | 0.16 | 0.19 | 0.28 | 0.08 | 0.15 | 0.15 | 0.34 | 0.12 | 0.18 | 0.08 | 0.08 | 0.71 | 0.06 | 0.08 | H |
| 75 | 1.65 | 0.04 | 0.01 | 0.65 | 0.38 | 0.08 | 0.07 | 0.07 | 0.05 | 0.04 | 0.18 | 0.14 | 0.18 | 0.21 | 0.07 | 0.15 | 0.15 | 0.15 | 0.11 | 0.16 | 0.08 | 0.08 | 0.79 | 0.06 | 0.07 | H |

| | | | | | | | | | | | | | | | | | | | | | | | |
|---|---|---|---|---|---|---|---|---|---|---|---|---|---|---|---|---|---|---|---|---|---|---|---|
| | | | | | | | | | | | | | | | | | | | | | | - | - | - |
| 81 | 1.49 | 1.74 | 0.09 | 0.07 | 0.07 | 0.85 | 0.08 | 0.09 | 0.06 | 0.07 | 0.20 | 0.13 | 0.15 | 0.21 | 0.08 | 0.13 | 0.12 | 0.11 | 0.16 | 0.06 | 0.08 | 0.08 | 0.07 |
| 88 | 1.87 | | 0.00 | 0.09 | 0.09 | 0.07 | 0.06 | 0.10 | 0.08 | 0.08 | 0.18 | 0.15 | 0.17 | 0.25 | 0.07 | 0.15 | 0.12 | 0.12 | 0.17 | 0.07 | 0.07 | 0.06 | 0.07 |
| 89 | 0.80 | | 0.08 | 0.09 | 0.07 | 0.08 | 0.08 | 0.09 | 0.07 | 0.15 | 0.14 | 0.24 | 0.08 | 0.14 | 1.17 | 0.12 | 0.18 | 0.12 | 0.18 | 0.07 | 0.07 | 0.06 | 0.07 |

Head

| | | | | | | | | | | | | | | | | | | | | | | | |
|---|---|---|---|---|---|---|---|---|---|---|---|---|---|---|---|---|---|---|---|---|---|---|---|
| 11 | 1.88 | 0.53 | 0.06 | 0.06 | 0.55 | 0.24 | 0.58 | 0.17 | 0.40 | 0.06 | 1.63 | 0.15 | 0.11 | 0.39 | 0.09 | 0.26 | 1.50 | 0.28 | 0.96 | 0.40 | 0.60 | 0.59 | 0.63 |
| 18 | 1.65 | 0.51 | 0.41 | 0.50 | 0.50 | 0.30 | 0.61 | 0.18 | 0.40 | 0.09 | 1.79 | 1.27 | 0.43 | 0.74 | 0.08 | 1.30 | 1.78 | 0.89 | 0.13 | 0.52 | 0.61 | 0.54 | 0.59 |
| 30 | 1.44 | 0.11 | 1.79 | 0.96 | 2.08 | 0.11 | 0.63 | 1.08 | 1.21 | 0.97 | 1.40 | 1.22 | 0.42 | 1.86 | 0.51 | 1.11 | 0.96 | 1.32 | 1.86 | 0.43 | 0.63 | 0.58 | 0.55 |
| 43 | 1.61 | 1.82 | 1.57 | 0.88 | 2.49 | 1.45 | 0.70 | 0.71 | 1.29 | 1.02 | 1.33 | 1.47 | 1.51 | 1.88 | 0.59 | 1.60 | 1.37 | 1.43 | 1.91 | 0.71 | 0.74 | 0.54 | 0.59 |
| 46 | 1.96 | 0.84 | 1.50 | 1.12 | 1.69 | 0.17 | 0.77 | 0.96 | 1.27 | 1.07 | 1.74 | 1.44 | 1.65 | 2.06 | 0.58 | 1.71 | 1.61 | 1.41 | 1.95 | 0.68 | 0.70 | 0.70 | 0.63 |
| 86 | 1.60 | 1.81 | 1.51 | 0.58 | 2.08 | 1.65 | 0.34 | 0.45 | 0.56 | 0.77 | 0.96 | 0.76 | 0.90 | 1.48 | 0.38 | 1.13 | 0.60 | 0.74 | 1.29 | 0.11 | 0.58 | 0.26 | 0.33 |
| 98 | 1.80 | 0.52 | 0.18 | 0.48 | 0.50 | 0.53 | 0.65 | 0.69 | 0.47 | 0.51 | 2.22 | 1.83 | 1.96 | 2.13 | 0.52 | 2.05 | 1.86 | 1.72 | 1.88 | 0.63 | 0.61 | 0.55 | 0.63 |

Stem

| | | | | | | | | | | | | | | | | | | | | | | | |
|---|---|---|---|---|---|---|---|---|---|---|---|---|---|---|---|---|---|---|---|---|---|---|---|
| 12 | 1.64 | 0.27 | 0.21 | 0.25 | 0.42 | 0.26 | 0.55 | 0.62 | 0.19 | 0.20 | 0.36 | 1.29 | 1.47 | 1.55 | 1.87 | 1.42 | 1.45 | 1.39 | 1.84 | 0.58 | 0.62 | 0.58 | 0.54 |
| 24 | 1.70 | 0.41 | 0.40 | 0.25 | 0.50 | 0.37 | 0.62 | 0.68 | 0.30 | 0.50 | 0.42 | 1.64 | 1.51 | 1.64 | 2.04 | 0.56 | 1.52 | 1.56 | 1.64 | 1.92 | 0.63 | 0.66 | 0.54 | 0.54 |
| 45 | 1.63 | 1.99 | 1.76 | 0.50 | 1.50 | 1.53 | 0.64 | 0.71 | 1.31 | 1.24 | 1.72 | 1.43 | 1.41 | 1.58 | 1.95 | 0.57 | 1.50 | 1.35 | 1.58 | 1.97 | 0.63 | 0.67 | 0.68 | 0.65 | 0.53 |
| 47 | 1.39 | 0.58 | 1.84 | 2.13 | 1.29 | 0.07 | 0.67 | 0.70 | 1.43 | 1.17 | 1.56 | 1.38 | 1.31 | 1.41 | 1.96 | 0.56 | 1.30 | 1.35 | 1.41 | 1.87 | 0.57 | 0.47 | 0.60 | 0.53 |
| 61 | 1.53 | 0.21 | 0.18 | 0.19 | 0.30 | 0.13 | 0.56 | 0.60 | 0.20 | 0.26 | 1.54 | 0.99 | 1.60 | 1.29 | 2.00 | 0.57 | 1.30 | 1.21 | 1.33 | 1.83 | 0.55 | 0.56 | 0.58 | 0.55 |
| 92 | 1.43 | 0.36 | 0.30 | 0.29 | 0.52 | 0.24 | 0.66 | 0.69 | 0.21 | 0.33 | 1.40 | 1.15 | 1.29 | 1.56 | 1.99 | 0.63 | 1.56 | 1.25 | 1.26 | 1.83 | 0.65 | 0.60 | 0.63 | 0.56 | 0.55 |

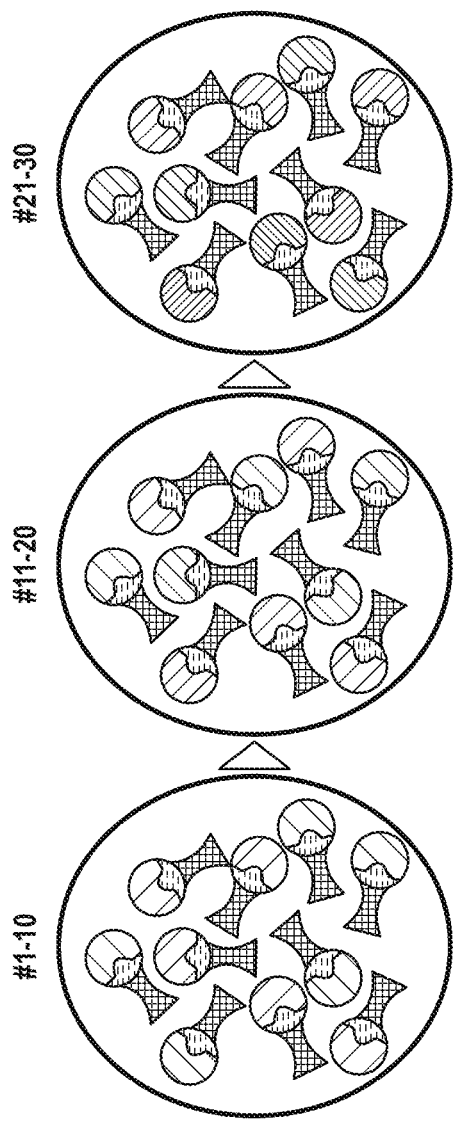
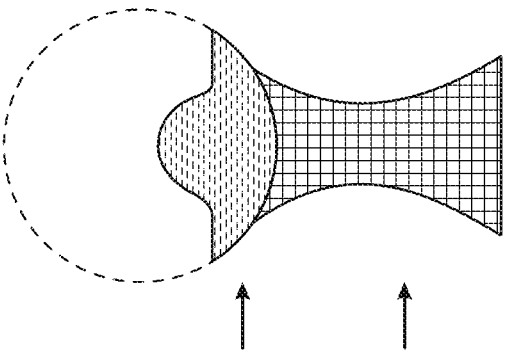
- IMMUNE RESPONSES TO SUBDOMINANT HEAD AND STEM EPITOPES
- AVOID IMPRINTING EFFECTS
- NEED TO IDENTIFY A

| | WT | | | | | | | | | | | 17 AA mutants | | | | | | | | |
|---|---|---|---|---|---|---|---|---|---|---|---|---|---|---|---|---|---|---|---|---|
| 1 | 1.98 | 0.04 | 0.06 | 0.01 | 0.05 | 0.04 | 0.08 | 0.06 | 0.04 | 0.09 | 0.07 | 0.11 | 0.12 | 0.08 | 0.08 | 0.08 | 0.07 | 0.08 | 0.09 | 0.07 | 0.08 | - |
| 2 | 1.96 | 0.04 | 0.06 | 0.05 | 0.04 | 0.08 | 0.08 | 0.06 | 0.04 | 0.10 | 0.26 | 0.13 | 0.11 | 0.08 | 0.08 | 0.08 | 0.13 | 0.08 | 0.08 | 0.07 | 0.08 | H |
| 5 | 2.06 | 0.04 | 0.06 | 0.11 | 0.04 | 0.09 | 0.07 | 0.07 | 0.05 | 0.11 | 0.13 | 0.12 | 0.15 | 0.10 | 0.10 | 0.09 | 0.14 | 0.08 | 0.08 | 0.07 | 0.08 | - |
| 10 | 1.96 | 0.05 | 0.08 | 0.06 | 0.06 | 0.12 | 0.10 | 0.08 | 0.05 | 0.21 | 0.16 | 0.20 | 0.15 | 0.10 | 0.09 | 0.10 | 0.16 | 0.09 | 0.07 | 0.08 | 0.08 | - |
| 16 | 1.88 | 0.04 | 0.04 | 0.05 | 0.04 | 0.08 | 0.09 | 0.06 | 0.06 | 0.08 | 0.08 | 0.09 | 0.21 | 0.13 | 0.13 | 0.17 | 0.24 | 0.09 | 0.10 | 0.08 | 0.09 | - |
| 25 | 1.32 | 0.24 | 0.07 | 0.01 | 0.06 | 0.04 | 0.09 | 0.04 | 0.04 | 0.09 | 0.13 | 0.15 | 0.10 | 0.07 | 0.07 | 0.13 | 0.11 | 0.07 | 0.08 | 0.07 | 0.07 | - |
| 40 | 1.93 | 0.34 | 0.06 | 0.01 | 0.04 | 0.04 | 0.09 | 0.05 | 0.05 | 0.13 | 0.11 | 0.15 | 0.16 | 0.08 | 0.10 | 0.08 | 0.15 | 0.07 | 0.08 | 0.06 | 0.07 | - |
| 54 | 1.95 | 0.24 | 0.05 | 0.25 | 0.04 | 0.10 | 0.08 | 0.05 | 0.05 | 0.16 | 0.15 | 0.18 | 0.18 | 0.12 | 0.12 | 0.08 | 0.18 | 0.08 | 0.08 | 0.07 | 0.08 | - |
| 71 | 1.61 | 0.35 | 0.09 | 0.25 | 0.05 | 0.09 | 0.09 | 0.05 | 0.05 | 0.24 | 0.17 | 0.22 | 0.23 | 0.15 | 0.15 | 0.00 | 0.22 | 0.08 | 0.07 | 0.06 | 0.07 | H |
| 95 | 1.67 | 0.34 | 0.05 | 0.01 | 0.04 | 0.11 | 0.08 | 0.07 | 0.04 | 0.18 | 0.22 | 0.21 | 0.21 | 0.14 | 0.18 | 0.00 | 0.19 | 0.09 | 0.08 | 0.06 | 0.08 | - |
| | | | | | | | | | | | | | | | | | | | | | | |
| | 1.66 | 1.39 | 0.09 | 1.10 | 0.05 | 0.09 | 0.07 | 0.08 | 0.05 | 0.08 | 0.10 | 0.11 | 0.09 | 0.07 | 0.08 | 0.09 | 0.12 | 0.11 | 0.07 | 0.07 | 0.07 | - |
| 4 | 1.66 | 1.39 | 0.09 | 1.10 | 0.05 | 0.09 | 0.07 | 0.08 | 0.05 | 0.08 | 0.10 | 0.11 | 0.09 | 0.07 | 0.08 | 0.09 | 0.12 | 0.11 | 0.07 | 0.07 | 0.07 | - |
| 6 | 1.91 | 0.04 | 0.07 | 0.05 | 0.11 | 0.10 | 0.06 | 0.04 | 0.14 | 0.15 | 0.20 | 0.10 | 0.09 | 0.11 | 0.90 | 0.11 | 0.24 | 0.08 | 0.09 | 0.08 | 0.09 | - |
| 7 | 1.94 | 0.04 | 0.06 | 0.04 | 0.07 | 0.08 | 0.07 | 0.05 | 0.10 | 0.09 | 0.13 | 0.15 | 0.08 | 1.09 | 0.10 | 0.00 | 0.18 | 0.07 | 0.09 | 0.07 | 0.06 | - |
| 13 | 1.85 | 0.04 | 0.05 | 0.00 | 0.06 | 0.09 | 0.06 | 0.06 | 0.27 | 0.09 | 0.11 | 0.13 | 0.09 | 0.11 | 1.02 | 0.00 | 0.15 | 0.08 | 0.08 | 0.07 | 0.07 | H |
| 15 | 1.83 | 0.04 | 0.05 | 0.00 | 0.05 | 0.09 | 0.06 | 0.06 | 0.14 | 0.11 | 0.09 | 0.15 | 0.09 | 0.08 | 1.30 | 0.00 | 0.15 | 0.08 | 0.08 | 0.07 | 0.07 | H |

FIG. 16B

| | | | | | | | | | | | | | | | | | | | | |
|---|---|---|---|---|---|---|---|---|---|---|---|---|---|---|---|---|---|---|---|---|
| | | | | | | | | | | | | H | | | H | H | | | | |
| 17 | 1.98 | 0.06 | 0.06 | 0.04 | 0.04 | 0.10 | 0.08 | 0.04 | 0.05 | 0.05 | 0.11 | 0.19 | 0.15 | 0.13 | 0.09 | 0.08 | 0.09 | 0.13 | 0.07 | 0.08 | 0.00 | 0.07 | 0.08 |
| 19 | 1.81 | 0.04 | 0.08 | 0.01 | 0.05 | 0.06 | 0.06 | 0.07 | 0.04 | 0.05 | 0.15 | 0.53 | 0.29 | 0.17 | 0.08 | 0.11 | 0.00 | 0.20 | 0.08 | 0.09 | 0.00 | 0.08 | 0.08 |
| 20 | 1.80 | 0.04 | 0.07 | 0.05 | 0.05 | 0.25 | 0.10 | 0.04 | 0.05 | 0.06 | 0.15 | 1.65 | 0.15 | 0.17 | 0.08 | 0.11 | 0.11 | 0.17 | 0.08 | 0.08 | 0.10 | 0.08 | 0.07 |
| 21 | 1.94 | 0.09 | 0.09 | 0.09 | 0.10 | 0.17 | 0.10 | 0.07 | 0.08 | 0.06 | 0.12 | 0.12 | 0.14 | 0.15 | 0.12 | 0.13 | 0.10 | 0.17 | 0.08 | 0.08 | 0.10 | 0.08 | 0.07 |
| 26 | 1.02 | 0.54 | 0.25 | 1.00 | 1.42 | 0.17 | 0.20 | 0.14 | 0.18 | 0.30 | 0.21 | 0.39 | 0.36 | 0.13 | 0.37 | 0.22 | 0.22 | 0.36 | 0.07 | 0.08 | 0.09 | 0.08 | 0.08 |
| 28 | 1.91 | 0.83 | 0.30 | 0.80 | 0.08 | 0.11 | 0.20 | 0.11 | 0.17 | 0.25 | 0.17 | 0.50 | 0.51 | 0.44 | 0.35 | 0.20 | 0.21 | 0.26 | 0.11 | 0.09 | 0.12 | 0.08 | 0.08 | H |
| 31 | 0.91 | 0.10 | 0.08 | 0.08 | 0.08 | 0.11 | 0.12 | 0.09 | 0.20 | 0.11 | 0.09 | 0.10 | 0.11 | 0.08 | 0.10 | 0.10 | 0.11 | 0.13 | 0.07 | 0.08 | 0.12 | 0.15 | 0.24 |
| 33 | 1.80 | 0.69 | 0.30 | 0.08 | 0.08 | 0.09 | 0.08 | 0.14 | 0.08 | 0.09 | 0.08 | 0.08 | 0.10 | 0.08 | 0.08 | 0.12 | 0.83 | 0.13 | 0.07 | 0.07 | 0.61 | 0.08 | 0.07 | H |
| 39 | 1.77 | 0.04 | 0.08 | 0.00 | 0.05 | 0.05 | 0.08 | 0.09 | 0.08 | 0.08 | 0.12 | 0.10 | 0.10 | 0.08 | 0.11 | 0.12 | 0.63 | 0.16 | 0.07 | 0.07 | 0.59 | 0.07 | 0.07 | H |
| 41 | 1.09 | 0.11 | 0.10 | 0.08 | 0.42 | 0.61 | 0.08 | 0.12 | 0.09 | 0.08 | 0.30 | 0.17 | 0.14 | 0.11 | 0.15 | 0.13 | 0.09 | 0.17 | 0.07 | 0.08 | 0.09 | 0.07 | 0.07 |
| 42 | 1.81 | 1.90 | 0.07 | 0.07 | 0.09 | 0.09 | 0.08 | 0.09 | 0.04 | 0.09 | 0.34 | 0.19 | 0.18 | 0.19 | 0.10 | 0.15 | 0.09 | 0.16 | 0.07 | 0.08 | 0.08 | 0.06 | 0.07 |
| 49 | 2.00 | 1.96 | 0.07 | 0.07 | 0.10 | 1.43 | 0.09 | 0.12 | 0.08 | 0.04 | 0.31 | 0.42 | 0.55 | 0.30 | 0.32 | 0.29 | 0.24 | 0.27 | 0.11 | 0.15 | 0.28 | 0.14 | 0.17 | H |
| 50 | 0.81 | 0.08 | 0.15 | 0.85 | 1.65 | 0.07 | 0.15 | 0.13 | 0.18 | 0.22 | 0.11 | 0.12 | 0.18 | 0.08 | 0.13 | 0.80 | 0.12 | 0.17 | 0.15 | 0.10 | 0.07 | 0.07 | H |
| 64 | 1.94 | 1.89 | 0.30 | 0.07 | 0.08 | 1.02 | 0.07 | 0.44 | 0.08 | 0.22 | 0.15 | 0.19 | 0.18 | 0.08 | 0.12 | 0.09 | 0.09 | 0.13 | 0.07 | 0.08 | 0.09 | 0.07 | 0.07 | H |
| 66 | 1.48 | 0.04 | 0.10 | 0.15 | 0.04 | 0.04 | 0.07 | 0.05 | 0.04 | 0.25 | 0.17 | 0.16 | 0.21 | 0.08 | 0.16 | 0.14 | 0.08 | 0.21 | 0.07 | 0.08 | 0.08 | 0.06 | 0.08 | H |
| 72 | 1.30 | 0.04 | 0.07 | 0.05 | 0.05 | 0.05 | 0.08 | 0.05 | 0.04 | 0.65 | 0.36 | 0.16 | 0.19 | 0.08 | 0.17 | 0.34 | 0.17 | 0.18 | 0.07 | 0.08 | 0.58 | 0.07 | 0.08 | H |
| 73 | 1.70 | 0.05 | 0.09 | 0.01 | 0.05 | 0.05 | 0.08 | 0.04 | 0.05 | 0.63 | 0.23 | 0.13 | 0.08 | 0.08 | 0.15 | 0.34 | 0.12 | 0.16 | 0.08 | 0.08 | 0.62 | 0.06 | 0.08 | H |
| 73 | 1.71 | 0.08 | 0.08 | 0.91 | 0.05 | 0.05 | 0.08 | 0.04 | 0.05 | 0.91 | 0.23 | 0.13 | 0.28 | 0.08 | 0.15 | 0.34 | 0.12 | 0.18 | 0.08 | 0.08 | 0.71 | 0.06 | 0.08 | H |
| 75 | 1.65 | 0.07 | 0.04 | 0.01 | 0.65 | 0.04 | 0.07 | 0.05 | 0.04 | 0.38 | 0.18 | 0.14 | 0.21 | 0.07 | 0.15 | 0.15 | 0.11 | 0.16 | 0.08 | 0.08 | 0.79 | 0.06 | 0.07 | H |

| | | | | | | |
|---|---|---|---|---|---|---|
| H1PORT1995 | TPGYFADYEELAKQLSSVSSTDRFKIFP | CLSSWPXITVT-PVSASN-NGXSSFYANLLWIT | GXN--GLYPNLSKSTVN | IXXXKVLVLWGVKLPPNIQN | 186 |
| H1N1PDS | TPGYFADYEELAKQLSSVSSTDRFKIFP | CLSSWPXITVE-VSWETVCT-NGXSSFYANLLWIT | GXN--GLYPNLSKSTVN | IXXXKVLVLWGVKLPPNIQN | 187 |
| H2 | TPGYFADYEELAKQLSSVSSTDRFKIFP | CLSSWPXITVE-VSWETVCT-NGXSSFYANLLWIT | GXN--GLYPNLSKSTVN | IXXXKVLVLWGVKLPPNIQN | 183 |
| H3 | TPGYFADYEELAKQLSSVSSTDRFKIFP | C--SSWPXITVE-VSWETVCT-NGXSSFYANLLWIT | GXN--GLYPNLSKSTVN | IXXXKVLVLWGVKLPPNIQN | 186

| | | |
|---|---|---|
| H1PORT1995 | QRLTWIENATVSVVSSNYSRRTTPKAIAKRPKVRDQDGRINIIWTLLKPGDTIIFKANGNLIAPWYAFALS·--------GTGSGIITSNAPMCTCQAK | 277 |
| H1N1PDS | QQLTWIENATVSVVSSNYSRRTTPKAIAKRPKVRDQDGRINIIWTLLKPGDTIIFKANGNLIAPWYAFALS·--------XTGSGIITSNAPMCTCQAK | 278 |
| H2 | QRLTWIENATVSVVSSNYSRRTTPKAIAKRPKVRDQDGRINIIWTLLKPGDTIIFKANGNLIAPWYAFALS·--------XTGSGIITSNAPMCTCQAK | 276 |
| H3 | QRLTWIENATVSVVSSNYSRRTTPKAIAKRPKVRDQDGRINIIWTLLKPGDTIIFKANGNLIAPWYAFALV·--------TGSGIITSNAPMCTQAKX | 277 |
| H5E221 | QRLTWIENATVSVVSSNYSRRTTPKAIAKRPKVRDQDGRINIIWTLLKPGDTIIFKANGNLIAPWYAFALS·--------GTGSGIITSNAPMCTCQAK | 276 |
| H6 | QRLTWIENATVSVVSSNYSRRTTPKAIAKRPKVRDQDGRINIIWTLLKPGDTIIFKANGNLIAPWYAFALVX--------GTGSGIITSNAPMCTQAKX | 280 |
| H8 | QRLTWIENATVSVVSSNYSRRTTPKAIAKRPKVRDQDGRINIIWTLLKPGDTIIFKANGNLIAPWYAFALVX--------GTGSGIITSNAPMCTQAKX | 279 |
| H9 | QRLTWIENATVSVVSSNYSRRTTPKAIAKRPKVRDQDGRINIIWTLLKPGDTIIFKANGNLIAPWYAFALVX--------GTGSGIITSNAPMCTCQAK | 270 |
| H11 | QRLTWIENATVSVVSSNYSRRTTPKAIAKRPKVRDQDGRINIIWTLLKPGDTIIFKANGNLIAPWYAFALVX--------GTGSGIITSNAPMCTQAKX | 217 |
| H12 | QRLTWIENATVSVVSSNYSRRTTPKAIAKRPKVRDQDGRINIIWTLLKPGDTIIFKANGNLIAPWYAFALVX--------GTGSGIITSNAPMCTCQAK | 217 |
| H13 | QRLTWIENATVSVVSSNYSRRTTPKAIAKRPKVRDQDGRINIIWTLLKPGDTIIFKANGNLIAPWYAFALVX--------GTGSGIITSNAPMCTCQAK | 216 |
| H16 | QRLTWIENATVSVVSSNYSRRTTPKAIAKRPKVRDQDGRINIIWTLLKPGDTIIFKANGNLIAPWYAFALVX--------GTGSGIITSNAPMCTQAKX | 215 |
| H17 | QRLTWIENATVSVVSSNYSRRTTPKAIAKRPKVRDQDGRINIIWTLLKPGDTIIFKANGNLIAPWYAFALVX--------GTGSGIITSNAPMCTCQAK | 215 |
| H18 | QRLTWIENATVSVVSSNYSRRTTPKAIAKRPKVRDQDGRINIIWTLLKPGDTIIFKANGNLIAPWYAFALVX--------GTGSGIITSNAPMCTQAKX | 276 |
| H3 | QRLTWIENATVSVVSSNYSRRTTPKAIAKRPKVRDQDGRINIIWTLLKPGDTIIFKANGNLIAPWYAFALS·--------GTGSGIITSNAPMCTCQA | 280 |
| H4 | QRLTWIENATVSVVSSNYSRRTTPKAIAKRPKVRDQDGRINIIWTLLKPGDTIIFKANGNLIAPWYAFALS·--------GTGSGIITSNAPMCTCQAK | 218 |
| H7 | QRLTWIENATVSVVSSNYSRRTTPKAIAKRPKVRDQDGRINIIWTLLKPGDTIIFKANGNLIAPWYAFALS·--------GTGSGIITSNAPMCTCQAK | 211 |
| H10 | QRLTWIENATVSVVSSNYSRRTTPKAIAKRPKVRDQDGRINIIWTLLKPGDTIIFKANGNLIAPWYAFALS·--------GTGSGIITSNAPMCTCQAK | 274 |
| H14 | QRLTWIENATVSVVSSNYSRRTTPKAIAKRPKVRDQDGRINIIWTLLKPGDTIIFKANGNLIAPWYAFALSRGIKCLLAEGTGSGIITSNAPMCTCQAK | 281 |
| H15 | QRLTWIENATVSVVSSNYSRRTTPKAIAKRPKVRDQDGRINIIWTLLKPGDTIIFKANGNLIAPWYAFALSRGIKCLLAEGTGSGIITSNAPMCTCQAK | 281 |

FIG. 17C

| | | |
|---|---|---|
| H1PORT1995 | CQTPQGAINSSLPTQNVKPVTIGKCPKTVRSAKLSXVTGLRNIPSIQG-----R | 326 |
| H1N1PDS | CQTPKGAINTSLPTQNIKPITIGKCFKTVKSTKLKLATGLANIPSIQS-----R | 327 |
| H2 | CQTPLGAINTTLPTKNVKPLTIGKCPKTVKSKKLVLATGLANVPQIKS-----R | 325 |
| H3 | CQTPLGAINTTLPTKNVKPLTIGKCPKTVKSKKLVLATGLANVPQIKS-----R | 336 |
| H5E221 | CQTPIGLAINSSMPTMNIKPLTIGECPKTVKSNRLVLATGLANSTQQKAAAKA | 329 |
| H6 | CQTPLGAINTTLPTKNVKPLTIGKCPKTVKSKKLVLATGLANVPQIKS-----R | 329 |
| H8 | CQTPLGAINTTLPTKNVKPLTIGKCPKTVKSKKLVLATGLANVPQIKS-----R | 338 |
| H9 | CQTPLGAINTTLPTKNVKPLTIGKCPKTVKSKKLVLATGLANVPQIKS-----R | 328 |
| H11 | CQTPLGAINTTLPTKNVKPLTIGKCPKTVKSKKLVLATGLANVPQIKS-----R | 326 |
| H12 | CQTPLGAINTTLPTKNVKPLTIGKCPKTVKSKKLVLATGLANVPQIKS-----R | 326 |
| H13 | CQTPLGAINTTLPTKNVKPLTIGKCPKTVKSKKLVLATGLANVPQIKS-----R | 325 |
| H16 | CQTPLGAINTTLPTKNVKPLTIGKCPKTVKSKKLVLATGLANVPQIKS-----R | 323 |
| H17 | CQTPLGAINTTLPTKNVKPLTIGKCPKTVKSKKLVLATGLANVPQIKGK----R | 334 |
| H18 | CQTPLGAINTTLPTKNVKPLTIGKCPKTVKSKKLVLATGLANVPQIKG-----R | 325 |
| H3 | CQTPLGAINTTLPTKNVKPLTIGKCPKTVKSKKLVLATGLANVPQIKG-----R | 329 |
| H4 | CQTPLGAINTTLPTKNVKPLTIGKCPKTVKSKKLVLATGLANVPQIKG-----R | 323 |
| H7 | CQTPLGAINTTLPTKNVKPLTIGKCPKTVKSKKLVLATGLANVPQIKG-----R | 38X |
| H10 | CQTPLGAINTTLPTKNVKPLTIGKCPKTVKSKKLVLATGLANVPQIKG-----R | 324 |
| H14 | CQTPLGAINTTLPTKNVKPLTIGKCPKTVKSKKLVLATGLANVPQIKG-----R | 338 |
| H15 | CQTPLGAINTTLPTKNVKPLTIGKCPKTVKSKKLVLATGLANVPQIKG-----R | 331 |

EXEMPLARY ANTIGENIC SITES IN H3 HA

| A | | B | | C | | D | | E | |
|---|---|---|---|---|---|---|---|---|---|
| 122 | T | 128 | T | 44 | Q | 96 | N | 57 | R |
| 124 | G | 129 | G | 45 | S | 102 | V | 59 | L |
| 126 | T | 155 | T | 46 | S | 103 | P | 62 | I |
| 130 | V | 156 | K | 47 | S | 117 | T | 63 | D |
| 131 | T | 157 | S | 48 | T | 121 | I | 67 | I |
| 132 | Q | 158 | G | 80 | K | 167 | T | 75 | H |
| 133 | N | 159 | S | 51 | I | 170 | N | 78 | V |
| 135 | R | 160 | T | 53 | N | 171 | N | 80 | Q |
| 137 | N | 163 | V | 54 | N | 172 | D | 81 | N |
| 138 | A | 164 | L | 273 | P | 173 | N | 82 | E |
| 140 | K | 165 | N | 275 | D | 174 | F | 165 | T |
| 142 | G | 186 | S | 276 | T | 175 | D | 86 | L |
| 143 | P | 187 | T | 278 | I | 176 | K | 87 | F |
| 144 | G | 188 | N | 279 | S | 177 | L | 88 | V |
| 145 | S | 189 | Q | 280 | E | 179 | I | 91 | S |
| 146 | G | 190 | E | 294 | F | 182 | I | 92 | K |
| 150 | R | 192 | T | 297 | V | 201 | R | 109 | R |
| 152 | N | 193 | S | 299 | K | 203 | T | 260 | M |
| 168 | M | 194 | L | 300 | I | 207 | R | 261 | R |
|  |  | 196 | V | 304 | A | 208 | R | 262 | T |
|  |  | 197 | Q | 305 | C | 209 | S | 265 | S |
|  |  | 198 | A | 307 | K | 212 | T |  |  |
|  |  |  |  | 308 | Y | 213 | I |  |  |
|  |  |  |  | 309 | V | 214 | I |  |  |
|  |  |  |  | 310 | K | 215 | P |  |  |
|  |  |  |  | 311 | Q | 216 | N |  |  |
|  |  |  |  | 312 | N | 217 | I |  |  |
|  |  |  |  |  |  | 218 | G |  |  |
|  |  |  |  |  |  | 219 | S |  |  |
|  |  |  |  |  |  | 226 | L |  |  |
|  |  |  |  |  |  | 227 | S |  |  |
|  |  |  |  |  |  | 228 | S |  |  |
|  |  |  |  |  |  | 229 | R |  |  |
|  |  |  |  |  |  | 230 | I |  |  |
|  |  |  |  |  |  | 238 | K |  |  |
|  |  |  |  |  |  | 240 | G |  |  |
|  |  |  |  |  |  | 242 | V |  |  |
|  |  |  |  |  |  | 244 | V |  |  |
|  |  |  |  |  |  | 246 | N |  |  |
|  |  |  |  |  |  | 247 | S |  |  |
|  |  |  |  |  |  | 248 | N |  |  |

FIG. 18

VECTORS FOR ELICITING IMMUNE RESPONSES TO NON-DOMINANT EPITOPES IN THE HEMAGGLUTININ (HA) PROTEIN

CROSS-REFERENCE TO RELATED APPLICATIONS

This application claims the benefit of the filing date of U.S. application No. 62/719,952, filed on Aug. 20, 2018, the disclosure of which is incorporated by reference herein.

STATEMENT OF GOVERNMENT RIGHTS

This invention was made with government support under HHSN272201400008C awarded by the National Institutes of Health. The government has certain rights in the invention.

BACKGROUND

Influenza outbreaks in humans are a major public health concern. Annual epidemics (outbreaks of influenza viruses circulating in humans) and sporadic pandemics (outbreaks of novel influenza viruses to which people lack protective immunity) increase morbidity and mortality in human populations and create considerable economic costs. Infections with influenza viruses and vaccination with current vaccines elicit antibodies against highly variable major antigenic epitopes in the head region of the viral surface glycoprotein hemagglutinin (HA). High mutation rates and immune pressure lead to the accumulation of mutations in these epitopes, resulting in viral 'escape' from the antibodies circulating in an individual; hence, the individual becomes infected again. As a consequence of viral 'escape' from immune responses elicited upon infection or vaccination, the vaccine strains must be replaced frequently. Recently, the National Institute of Allergy and Infectious Diseases (MAID) therefore announced a strategic plan for the development of a 'universal' influenza vaccine that protects against multiple, antigenically diverse strains.

Immunodominance describes the phenomenon whereby strong immune responses are directed towards a subset of antigenic epitopes (i.e., immunodominant antigenic epitopes), while much weaker immune responses are directed against the remaining, immune-subdominant epitopes. The immunodominant epitopes of influenza viruses are located in the highly variable regions of the HA head (i.e., most antibodies elicited after infection or vaccination are directed against these major antigenic epitopes). Immune-subdominant epitopes are located in conserved regions of the HA head and in the conserved HA stem. Antibodies elicited to these subdominant, conserved regions are typically reactive against a broad range of influenza viruses; however, since the epitopes are immune-subdominant, the levels of these broadly reactive antibodies are low.

Several studies have shown that the first exposure to an antigenically unique influenza virus generates relatively high levels of antibodies to immune-subdominant epitopes in the HA stem, in addition to high levels of antibodies to the immunodominant major epitopes in the highly variable regions of the HA head. Palese and colleagues demonstrated that repeat immunization with chimeric HAs that possess the same stem region but head regions derived from different HA subtypes increased the levels of stem-reactive antibodies compared to repeat vaccination with HAs possessing the same head (Chen et L., 2016; Krammer et al., 2013; Margine et al., 2013; Nachbagauer et al., 2017 and 2015; Krammer et al., 2012 and 2014; Goff et al., 2013).

Despite the promising data obtained with chimeric HAs, this approach has drawbacks: (i) the number of HA subtypes that can be used to swap the head region is limited (and not all combinations of stems and heads are stable); and (ii) the current approach of exchanging the HA head does not exploit the subtype-specific conserved, immune-subdominant epitopes in the head.

Human influenza virus infections pose a considerable burden on individual health, the public health sector, and the global economy. Influenza viruses circulating in humans (i.e., 'seasonal' influenza viruses) typically cause annual epidemics that have resulted in the US alone in 9.2-35.6 million illnesses, 140,000-710,000 hospitalizations, and 12,000-56,000 deaths per year since 2010. Epidemics are caused by influenza viruses of type A and B. Influenza viruses of type A are further divided into subtypes based on the antigenicity of the viral surface glycoproteins HA and neuraminidase (NA). To date, 18 HA (H1-18) and 11 NA (N1-11) subtypes have been identified; based on their phylogenetic relationships, the HAs are categorized into two super-groups (group 1, H1, H2, H5, H6, H8, H9, H11-H13, H16-18; group 2, H3, H4, H7, H10, H14, H15). However, only viruses of the H1N1, H2N2, and H3N2 subtypes have extensively circulated in humans. Global outbreaks (pandemics) are caused by viruses possessing an HA that is antigenically distinct from that of viruses previously circulating in humans, so they encounter immunologically naïve populations, resulting in rapid spread around the globe. Four pandemics have occurred in the last 100 years. The 1918 pandemic was caused by H1N1 viruses, which were replaced by H2N2 viruses in 1957, causing the 'Asian' pandemic. In 1968, H3N2 viruses replaced the H2N2 viruses, causing the 'Hong Kong' pandemic. H1N1 viruses similar to those circulating in the 1950's re-emerged in 1977 and co-circulated with H3N2 viruses until 2009, when the H1N1 viruses were replaced by H1N1 viruses with an antigenically distinct HA (2009 pandemic).

Wild aquatic birds are the natural reservoir of influenza A viruses and harbor influenza viruses of most subtypes. Sporadic transmission of avian influenza viruses to humans can cause severe respiratory disease with high fatality rates. Highly pathogenic avian influenza of the H5 subtype have infected 840 people and caused 454 deaths; human infections with H7N9 viruses (which emerged in 2013) have resulted in 1,625 reported human cases with a case fatality rate of 38% (as of May 24, 2018). These avian influenza viruses do not efficiently transmit among humans and have not (yet) caused a pandemic, although H7N9 viruses transmit via respiratory droplets among ferrets (1-4) (the commonly used animal model for influenza virus transmission studies) and H5 viruses with a small number of mutations can become transmissible among ferrets via respiratory droplets (5, 6). Any universal vaccine strategy should ideally be applicable/adaptable to these types of viruses.

SUMMARY

Disclosed herein is a method to redirect immune responses in an avian or a mammal from the immunodominant epitopes (which mutate frequently) towards non-dominant (sub-dominant) epitopes, which are more conserved. Immunization with one or more viruses produced by the method produce higher amounts of antibodies targeting the conserved non-dominant epitopes which in turn increases broadly-protective immunity. The method outdilutes immune responses to the immunodominant epitopes, resulting in higher levels of antibodies directed against the conserved, non-dominant epitopes. Influenza vaccines having one or more of the influenza viruses with modified HAs that elicit immune responses to non-dominant epitopes, epitopes that are more conserved than the dominant antigenic epitopes on the hemagglutinin (HA) head of influenza viruses, e.g., human influenza viruses, may provide protection against antigenically drifted viruses. Thus, the need to vaccinate may be extended beyond 1-3 years. The vaccines may include mixtures of different HA proteins, each with mutated. e.g., non-naturally occurring, immunodominant antigenic epitopes, in order to dilute the immune responses to the immunodominant epitopes, thereby boosting the levels of antibodies directed against immune-subdominant epitopes.

As described herein, an influenza virus 'library' (e.g., a mixture of millions of variants) is generated with random mutations at selected positions of the highly variable immunodominant antigenic epitopes in the HA head, e.g., from any of the HA subtypes. For example, in a H3 HA, influenza viruses with up to 17 mutations in the immunodominant antigenic epitopes of HA were prepared and found to be viable. The virus library is incubated with different sera, e.g., ferret and/or human sera, to eliminate variants that are antigenically similar to wild-type virus(es). The individual modified HA sequences (Individual ID-EpiMut HAs) may be cloned, sequenced, and tested for their reactivity with monoclonal antibodies directed against immunodominant or sub-dominant epitopes of HA. ID-EpiMut HAs with high reactivity to antibodies directed against conserved, immune subdominant epitopes and low reactivity to antibodies directed against immunodominant epitopes are then isolated and optionally pooled in a vaccine formulation.

In one embodiment, for immunization studies in mice, the ID-EpiMut HAs are incorporated into virus-like particles (VLPs) composed of the Ebola virus VP40 matrix protein, hence eliminating potential contributions to immunity conferred by other influenza viral proteins. The mouse sera is tested for the levels of antibodies directed against immunodominant or -subdominant epitopes. Vaccination and challenge studies in ferrets are carried out with inactivated influenza vaccines possessing ID-EpiMut HAs. Naïve or pre-exposed animals are vaccinated, the levels of antibodies to immune subdominant epitopes assessed, and animals challenged with homologous and heterologous influenza viruses. ID-EpiMut based vaccines are likely be more cross-protective than vaccines based on wild-type HA.

Thus, the disclosure provides a method to elicit broadly protective antibodies to immune-subdominant epitopes in HA of any subtype. Mixtures of influenza viruses or mixtures of other vectors, e.g., mixtures of isolated nucleic acid including mRNA and DNA encoding the altered HAs, including other viral vectors, e.g., filoviruses, adenoviruses, and the like, or virus-like particles including Ebola VLPs and influenza VLPs, or mixtures of polypeptides having altered influenza hemagglutinins (HAs), altered with a non-naturally occurring immunodominant antigenic head, as a result of substitutions and/or deletions in residues that form the immunodominant epitope, and conserved, immune subdominant epitopes (FIG. 2) provide a vaccine that may elicit high amounts of Abs to the conserved, immune subdominant epitopes in the head and in the stem, resulting in broader protection than that elicited by current vaccines. A composition having an individual recombinant virus, e.g., influenza virus, filovirus, adenovirus, or a VLP thereof, comprising HA having one or more of the altered residues, isolated nucleic acid encoding HA having one or more of the altered residues, or isolated HA having one or more of the altered residues, is envisioned.

In one embodiment, a recombinant influenza virus produced by the method has a HA that has one or more altered residues in one or more immunodominant epitopes of HA (residues in an epitope do not need to be contiguous or in close proximity in the primary amino acid sequence) resulting in altered epitopes that do not, for example, bind antibodies specific for the one or more immunodominant epitopes as efficiently as the (unaltered) immunodominant epitopes in the parental HA, and/or once administered, the HA with the one or more altered residues in the immunodominant epitopes elicit antibodies to conserved, immune subdominant epitopes in the head and/or in the stem of HA. In one embodiment, a recombinant influenza virus produced by the method has 20 or fewer unaltered residues that are part of one or more immunodominant epitopes, e.g., 15, 10, 5, 4, 3, 2, 1 or 0 residues are unaltered in one or more naturally occurring immunodominant epitope, for instance, in a specific parental influenza virus. In one embodiment, a recombinant influenza virus produced by the method has 1 to 10 or 10 to 20 altered immunodominant residues in two or more immunodominant epitopes. In one embodiment, a recombinant influenza virus produced by the method has 10 or fewer, e.g., 5 or 3, unaltered immunodominant residues in one or two immunodominant epitopes. For example, a recombinant influenza H3 virus produced by the method has 5 or fewer immunodominant residues at positions 121, 131, 135, 138, 140, 142, 144, 145, 155, 156, 157, 158, 171, 189, 193, 212, or 225. For example, a recombinant influenza H5 virus produced by the method has 5 or fewer immunodominant residues at positions 119, 123, 125, 126, 127, 129, 138, 140, 141, 151, 152, 153, 154, 155, 156, 185, or 189 in H5.

In one embodiment, a recombinant influenza virus produced by the method has 2 or more residues, e.g., has 2, 3, 4, 5, 6, 7, 8, 9, 10, 11, 12, 13, 14, 15, 16, 17 or more residues, that result in decreased antibody binding with antibodies that recognize immunodominant epitopes. Thus, residues in immunodominant epitopes are replaced (substituted) with residues that, if present in a HA in an influenza virus that infects an animal that has been infected with the HA with the immunodominant epitope, does not result in a memory response (immunological memory) as a result of the substitutions but instead redirects the immune response to sub-dominant epitopes in the HA head or stem, allowing for a broader immune response, e.g., to a specific HA subtype or a specific clade in a HA subtype. In one embodiment, a recombinant influenza virus produced by the method has 2 to 5, 5 to 10, 10 to 15, 15 to 20, or more substitutions in residues in immunodominant epitopes. In one embodiment, a recombinant influenza virus produced by the method has about 10 to 17 substitutions in residues in immunodominant epitopes. For example, a recombinant influenza H3 virus produced by the method has 2 to 5, 5 to 10, 10 to 15, or 10 to 17 non-dominant residues at a combination of positions 121, 131, 135, 138, 140, 142, 144, 145, 155, 156, 157, 158, 171, 189, 193, 212, or 225. For example, a recombinant influenza H5 virus produced by the method has 2 to 5, 5 to 10, 10 to 15, or 10 to 17 substitutions (to non-dominant residues) at a combination of positions 119, 123, 125, 126, 127, 129, 138, 140, 141, 151, 152, 153, 154, 155, 156, 185, or 189 in H5. In one embodiment, a recombinant influenza virus produced by the method has 1 to 2, 2 to 5, or up to 10 residues deleted, including for example positions 121, 131, 135, 138, 140, 142, 144, 145, 155, 156, 157, 158, 171, 189, 193, 212, or 225 in H3, or positions 119, 123, 125, 126, 127, 129, 138, 140, 141, 151, 152, 153, 154, 155, 156, 185, or 189 in H5, which deletion(s) in HA result in decreased antibody binding with antibodies that recognize immunodominant epitopes In one embodiment, a vaccine comprises a plurality of recombinant influenza viruses having substitutions (or deletions) at immunodominant positions (substitutions to "non-immunodominant residues"). In one embodiment, the vaccine comprises 2 to 5, 5 to 10, 10 to 20, 20 to 30, 30 to 40, or 40 to 50 distinct recombinant influenza viruses having substitutions (or deletions) at immunodominant epitope positions. In one embodiment, the vaccine comprises 2, 3, 4, 5, 6, 7, 8, 9, 10, 11, 12, 13, 14, 15, 16, 17, 18, 19 or 20 distinct recombinant influenza viruses having substitutions at immunodominant epitope positions. In one embodiment, the vaccine comprises 21, 22, 23, 24, 25, 26, 27, 28, 29, 30, 31, 32, 33, 34, 35, 36, 37, 38, 39 or 40 distinct recombinant influenza viruses having substitutions at immunodominant epitope positions.

In one embodiment, combinations of vectors with altered HAs in Tables 1 or 6 are employed in a composition that is administered to a mammal or an avian.

BRIEF DESCRIPTION OF FIGURES

FIG. 5. Flowchart.

FIGS. 6A-6B. Exemplary HA sequences of H3N2 viruses and a H5N8 virus (SEQ ID Nos. 1 and 6-9).

FIG. 7. HA sequence of an exemplary H5 (SEQ ID NO:2).

FIG. 8. HA sequences of an exemplary H1 (SEQ ID NO:3).

FIG. 9. HA sequence of an exemplary H2 (SEQ ID NO:4).

FIG. 10. HA sequence of an exemplary H7 (SEQ ID NO:5).

FIGS. 11A-11B. H3 variants with substitutions in immunodominant epitope residues.

Figure 12H:
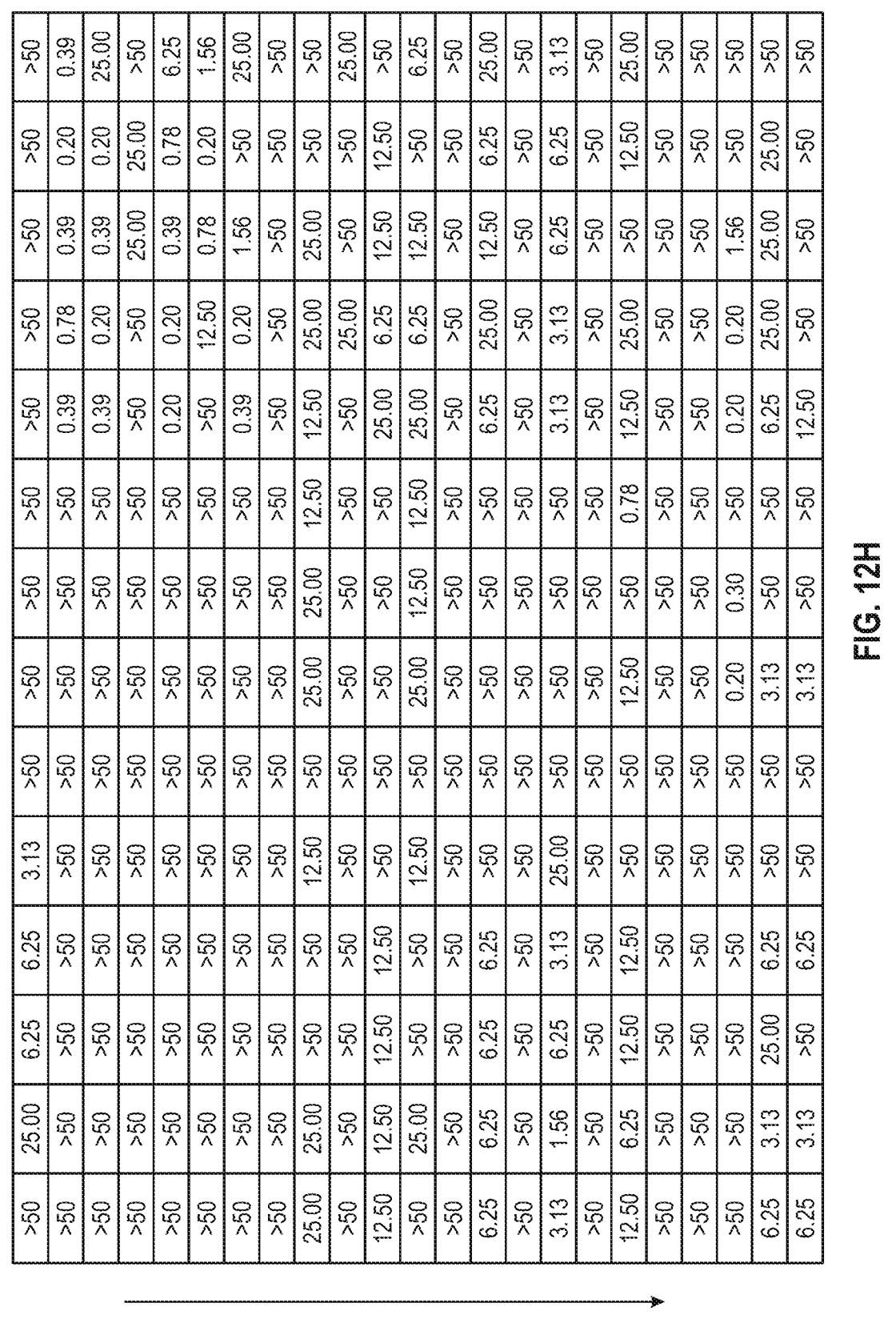

FIGS. 12A-12M. Antibody reactivities for clusters, wild-type and H3 variants with substitutions in immunodominant epitope residues.

FIGS. 13A-13D. Antibody reactivities for wild-type and H3 variants with substitutions in immunodominant epitope residues.w FIGS. 14A-14D. Antibody reactivities for wild-type and selected H3 variants with substitutions in immunodominant epitope residues.

FIGS. 15A-15D. Combining sets of 10 independent (distinct) H3 variants with substitutions in immunodominant epitope residues.

Figure 16D:
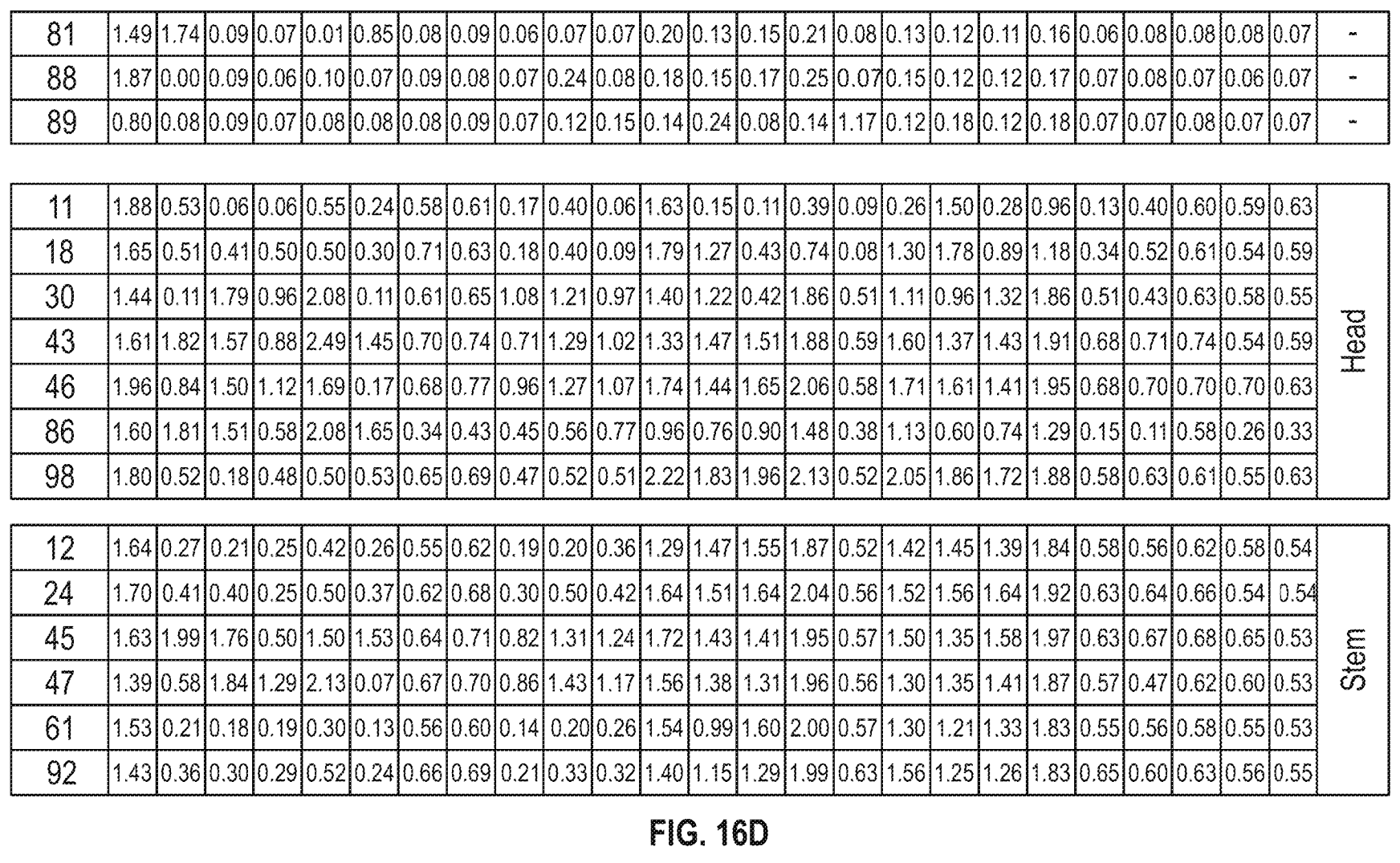

FIGS. 16A-16D. Mixtures of H3 variants with substitutions in immunodominant epitope residues react with antibodies to sub-dominant epitopes.

Figure 17A:
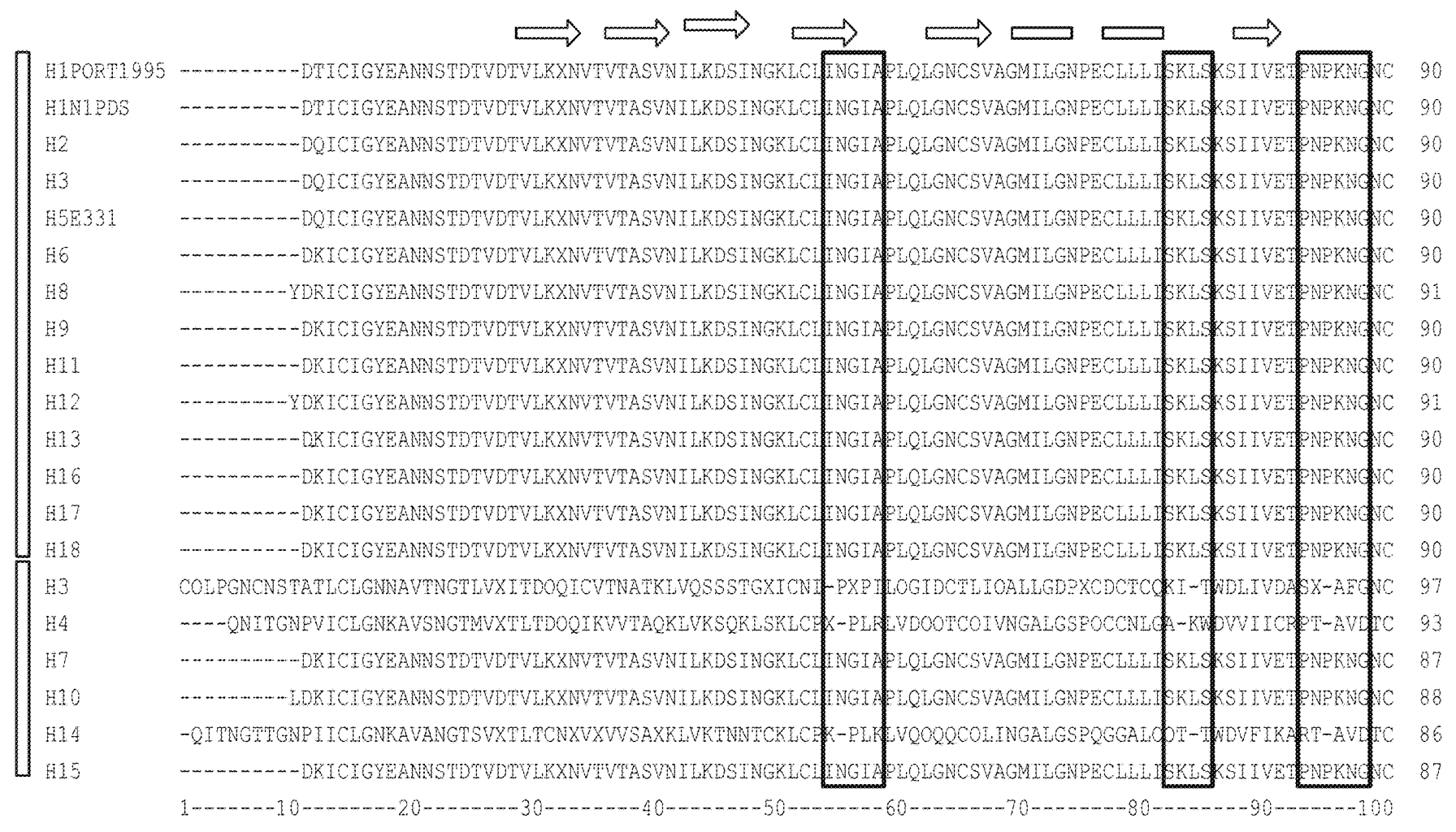

FIGS. 17A-17D. Alignment of HA subtypes (see, e.g., Burke et al., *PLoS One,* 9:e112302 (2014)).

FIG. 18. Exemplary antigenic sites in H3 HA.

DETAILED DESCRIPTION

Definitions

Figure 1:
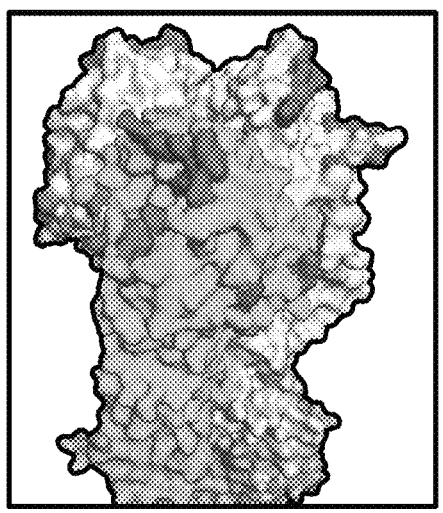
FIG. 1. X-ray structure of a human H3 HA protein. The positions targeted by mutagenesis are show in red.
Figure 2:
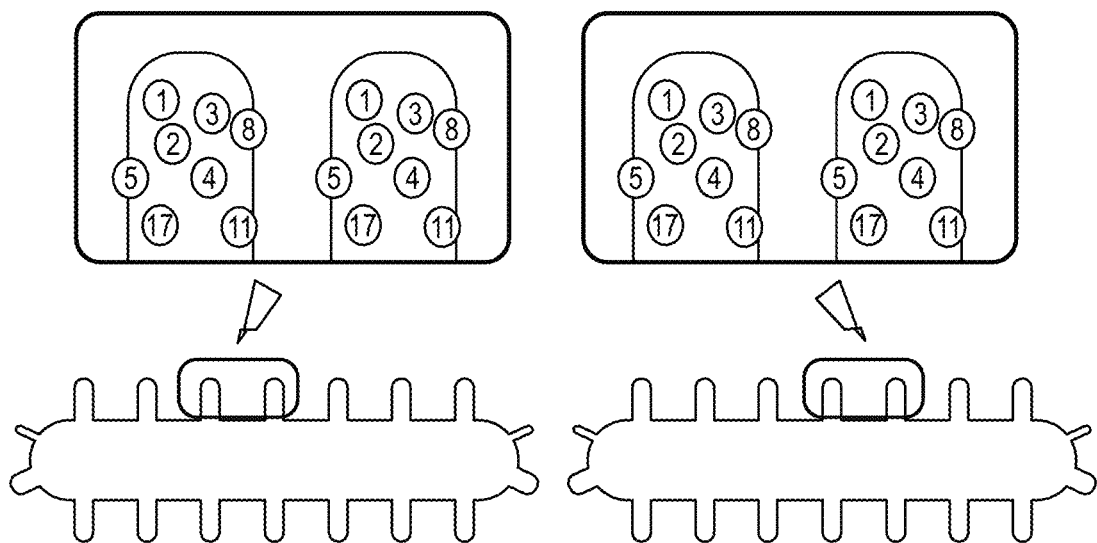
FIG. 2. Ebola VP40-based VLPs possessing wild-type HA (left), or HA with randomized amino acid changes at up to 17 amino acid positions (right).

As used herein, the term "isolated" refers to in vitro preparation and/or isolation of a nucleic acid molecule, e.g., vector or plasmid, peptide or polypeptide (protein), or virus, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or viral segment is from an influenza virus source that is different than a majority of the other influenza viral genes or viral segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information.

The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5. N=−4, and a comparison of both strands. For amino acid sequences, the BLASTP program may use as defaults a wordlength (W) of 3, an expectation (E) of 10, and the BLOSUM62 scoring matrix. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Immunodominant HA Epitopes and Methods to Alter Those Epitopes

Both the processes of infection and vaccination with influenza viruses elicit, primarily, antibodies against the immune-dominant epitopes in the 'head' region of the viral hemagglutinin (HA) protein, the major viral antigen. Mutations in the immune-dominant epitopes may confer 'escape' from the antibodies circulating in an individual, so that a person that gained immunity to the previous influenza virus becomes vulnerable to the mutated 'escape variant' virus. Several strategies are being tested to redirect a recipient's immune response from the immune-dominant epitopes (which mutate frequently) in HA towards non-dominant epitopes in HA, which are more conserved. Targeting the conserved non-dominant epitopes should increase broadly-protective immunity.

Infections or vaccinations with influenza viruses elicit neutralizing antibodies that protect against infection with an antigenically closely related virus. Most neutralizing antibodies are directed against highly variable, immunodominant antigenic epitopes in the head of HA. For H3N2 viruses, early studies with antigenic escape mutants against mouse monoclonal antibodies identified five immunodominant antigenic epitopes (A-E) in the head of HA (Wiley et al., 1981 and 1987) (FIG. 1). The high mutation rate of influenza viruses and immune pressure in previously infected and/or vaccinated people result in the accumulation of mutations in these immunodominant antigenic epitopes, causing the antibodies circulating in an individual to no longer neutralize the virus. This so-called 'antigenic drift' is why humans get re-infected with seasonal influenza viruses. Current seasonal influenza vaccine strains are selected based on the antigenic properties of the highly variable immunodominant antigenic epitopes in the HA head. Therefore, the vaccine strain must be replaced for each new cluster or clade of antigenic drift variants. Moreover, antigenic drift may occur between the time the vaccine is selected (February for the northern hemisphere) and the start of the influenza season (fall in the northern hemisphere), rendering the vaccine largely ineffective ('vaccine mismatch').

Most antibodies (Abs) elicited upon influenza virus infection or vaccination are directed against the highly variable, immunodominant antigenic epitopes on the HA head; therefore, they only react with closely related viruses. In 1993, Okuno et al. reported a monoclonal Ab (mAb) that neutralized influenza viruses of two different subtypes. This finding was not fully appreciated at the time, and it was another decade before numerous studies reported mAbs that reacted with multiple HAs of the same subtype, with HAs of another subtype from the same group, with HAs from both groups 1 and 2, or with both influenza A and B virus HAs. Most of these broadly reactive mAbs bind to the HA stem (which anchors HA in the membrane and mediates the pH-induced membrane fusion event in late endosomes that releases the viral genome into the cytosol) (FIG. 1). However, some broadly reactive mAbs interact with conserved regions in the HA head. These mAbs fall into at least two main categories; broadly reactive mAbs that interact with a conserved, immune-subdominant epitope in the center of the receptor-binding site (conserved among most HA subtypes), and broadly reactive mAbs that interact with conserved, immune-subdominant epitopes on the HA head outside the receptor-binding pocket (these epitopes may not be conserved among all subtypes). The conserved, immune-subdominant epitopes evolve at a much slower rate than the immunodominant epitopes, explaining why antibodies that bind to the conserved epitopes react with more diverse strains (compared with antibodies that interact with the major antigenic epitopes). Antibodies directed at the conserved, immune-subdominant epitopes may therefore provide protection against viruses of different antigenic clusters within the same subtype, or against viruses of different subtypes.

Broadly reactive Abs to conserved regions in HA may pave the way for the development of broadly protective influenza vaccines. However, the conserved epitopes are immune-subdominant and Abs to these epitopes are detected at much lower levels than Abs targeting the immunodominant, highly variable major antigenic epitopes in the HA head. Researchers have therefore tried to refocus immune responses from the immunodominant, highly variable major epitopes in the HA head towards the conserved, immune-subdominant epitopes of HA.

A study in the 1980s demonstrated that vaccination with an HA lacking the head region ('headless HA') elicited stem-reactive Abs that reacted with the HA protein of a different subtype (Graves et al., 1983). Removing the HA head appeared to be an appealing strategy to elicit Abs to the conserved stem, and various membrane-anchored or secreted versions of headless HAs have been tested. Some of these studies led to the generation of broadly protective antibodies upon vaccination, but headless HAs are of low stability and may not fold correctly; moreover, they lack the conserved, immune-subdominant epitopes in the HA head.

In 2011, Wilson and colleagues reported that infection with the pandemic 2009 H1N1 virus (an antigenically novel influenza virus that had not circulated in humans prior to 2009) elicited more broadly cross-reactive antibodies against conserved, immune-subdominant epitopes in the HA stem than typically detected after infection or vaccination with a seasonal influenza virus (Wrammert et al., 2011). Others reported similar results. Moreover, vaccination with experimental vaccines to H5 (Ellebedy et al., 2014; Nachbagauer et al., 2014) or H7 viruses (Henry et al., 2016 and 2015; Liu et al., 2017; Krammer et al., 2014; Halliley et al., 2015), neither of which circulate in humans, elicited higher amounts of broadly reactive antibodies to conserved, immune-subdominant epitopes in the HA stem than typically detected after infection or vaccination with a seasonal influenza virus. This effect was strongest after the first encounter with a novel (not previously encountered) HA. For example, the first vaccination with a pandemic 2009 H1N1 vaccine elicited high levels of broadly reactive Abs to immune-subdominant epitopes in the HA stem (Andrews et al., 2015). However, after the second exposure to the pandemic 2009 H1N1 virus, most Abs were directed against immunodominant epitopes in the HA head, and the level of Abs directed against the immune-subdominant stem epitopes declined considerably compared with the levels measured after the first exposure (Andrews et al., 2015). Collectively, these findings indicate that the first encounter with an unique HA elicits appreciable amounts of broadly reactive Abs to conserved, immune-subdominant epitopes. In contrast, repeated infection or vaccination with seasonal influenza viruses (which differ by as little as one or two amino acids in one major antigenic epitope but share the other major epitopes) primarily stimulates (recall) Abs to the immunodominant antigenic epitopes.

Exemplary Methods

The present disclosure relates to influenza vaccines based on a distinct 'outdilution' approach for improving the antigenic response to the non-dominant epitopes. Customized influenza viruses with strategically antigenically-distinct immunodominant epitopes (the residues in the immunodominant epitope are changed to residues that do not react with antibodies that recognize the immunodominant epitope) in the 'head' region of HA are pooled, so that the response of the body is to make small amounts of antibodies to the various antigenically-distinct immunodominant epitopes (also referred to as non-immunodominant epitope residues), whereas the large amount of conserved non-dominant epitopes shared by the entire pool strengthen the response to those non-dominant epitopes and thereby create an immune response that is more likely to prove protection against a range of circulating natural viruses, which can be predicted to share those conserved non-dominant epitopes, also.

In one embodiment, a plurality of positions in HA, e.g., up to 17 positions in H3 HA, that are known or suspected of being associated with an epitope, are randomly mutated. For H3, 60 viable viruses were recovered. Monoclonal antibodies are used to evaluate the antigenicity of the recovered viruses. Many of the viruses bind to a limited number of the tested mAbs, which apparently correspond to non-dominant epitopes. The same approach can be used for a range of subtypes or just one subtype (e.g., H3N2, H5N1, etc.) that makes up the vaccine cocktail. For human seasonal H3N2 viruses, the method resulted in viruses with 'heavily' mutated immunodominant antigenic epitopes, viruses that were viable, functional, and antigenically distinct from the parent virus.

In one embodiment, a pan-H3 vaccine is prepared from the modified HA containing viruses that confers protection against multiple antigenic clusters of seasonal human 13N2 viruses. Since the mixtures of immunodominant antigenic head epitopes that have not been detected in nature, the immune response is focused towards conserved, immune subdominant epitopes. Because the method can generate millions of HA variants with multiple non-naturally occurring mutations in the immunodominant epitopes, viable viruses that possess multiple amino acid changes in their immunodominant epitopes that alter their antigenic properties can be obtained. Unlike other approaches, vaccine candidates are prepared that (i) present non-naturally occurring immunodominant antigenic head epitopes, (ii) preserve the conserved, immune subdominant epitopes in the HA stem and the HA head; and (iii) maintain the structural and functional integrity of HA; as a result, our vaccine candidates should be more cross-protective than vaccines based on a wild-type virus.

Influenza Vaccines

A vaccine of the invention includes at least one of the isolated recombinant influenza viruses having the desired property, e.g., one or more of non-naturally occurring immunodominant antigenic head epitopes and/or conserved, immune subdominant epitopes in the HA stem and the HA head, as well as maintaining the structural and functional integrity of HA, and optionally one or more other isolated viruses including other isolated influenza viruses having the desired property, one or more immunogenic proteins or glycoproteins of one or more isolated influenza viruses or one or more other pathogens. e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantadine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 µg, e.g., 30 to 100 µg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition having one of more influenza viruses with the desired properties may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{20}$, e.g., $10^3$-$10^{12}$, $10^2$-$10^{10}$, $10^5$-$10^{11}$, $10^6$-$10^{15}$, $10^2$-$10^{10}$, or $10^{15}$-$10^{20}$ plaque forming units (PFU)/kg, or any range or value therein. The dose of one viral isolate vaccine, e.g., in an inactivated vaccine, may range from about 0.1 to 1000, e.g., 0.1 to 10 µg, 1 to 20 µg, 30 to 100 µg, 10 to 50 µg, 50 to 200 µg, or 150 to 300 µg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 µg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 µg or any range or value therein, or the amount recommended by the U.S. Public Heath Service (PHS), which is usually 15 µg, per component for older children >3 years of age, and 7.5 µg per component for children <3 years of age. The quantity of NA can also be standardized, however, this glycoprotein can be labile during the processor purification and storage (Kendal et al., 1980; Kerr et al., 1975). Each 0.5-ml dose of vaccine may contain approximately 0.1 to 0.5 billion viral particles, 0.5 to 2 billion viral particles, 1 to 50 billion virus particles, 1 to 10 billion viral particles, 20 to 40 billion viral particles, 1 to 5 billion viral particles, or 40 to 80 billion viral particles.

EXEMPLARY EMBODIMENTS

In one embodiment, a method to prepare a plurality of influenza virus nucleic acid molecules encoding a hemagglutinin (HA) having a reduced number of immunodominant epitopes is provided. The method includes introducing random mutations at a plurality of codons in an isolated parental influenza virus nucleic acid molecule encoding a hemagglutinin having immunodominant epitopes, thereby providing a library of influenza virus nucleic acid molecules encoding a mutant hemagglutinin, wherein the mutations are at codons that encode a residue in an immunodominant epitope in the parental hemagglutinin; introducing the library into cells so as to provide a library of cells that express the mutant hemagglutinins; and identifying nucleic acid molecules encoding a mutant hemagglutinin with a reduced number of immunodominant epitopes as a result of substitutions and/or deletions at residues that form the immunodominant epitopes. In one embodiment, the cells are mammalian cells. In one embodiment, the hemagglutinin (HA) is H1, H2, H3, H5, H6, 117, or H9. In one embodiment, the mutant HA has non-immunodominant residues at two or more of positions 121, 131, 135, 138, 140, 142, 144, 145, 155, 156, 157, 158, 171, 189, 193, 212, or 225 in H3. In one embodiment, the residue in H3 at position 121 is Q, R, I, L, V, S, F, Y or A, position 131 is R, V, S, Q, C, V, Y, D, E, or L, position 135 is Y, K, N, V, W, S, V, or P, position 138 is W, K, I, R, or L, position 140 is L, M, T, S, R K, M, or P, position 142 is N, G, Y, Q, E, H, N, L, or P, position 144 is T, V, G, D, H, L or Q, position 145 is P, R, W or K, position 155 is C, I, R, A, V, S or N, position 156 is P, G, S, T, A, or C, position 157 is D, P, S, G, 1, R or T, position 158 is R, V, S, A, K, C, Q, position 171 is T, F, L, E, H, C or R, position 189 is A, P, T, L, A, S, Y, or R, position 193 is Q, R, N, T, E, V, or P, position 212 is V, R, G, S, M, D or E, or position 225 is L, P, C, S, Q, G, Y, or F. In one embodiment, the residue in H3 at position 121 is not N, position 131 is not T, position 135 is not T, position 138 is not A, position 140 is not 1, position 142 is not R, position 144 is not S, position 145 is not S, position 155 is not T, position 156 is not H, position 157 is not L, position 158 is not N, position 171 is not N, position 189 is not K, position 193 is not F, position 212 is not A, or position 225 is not D. In one embodiment, the residue in 113 at position 121 is N, position 131 is T, position 135 is T, position 138 is A, position 140 is I, position 142 is R, position 144 is S, position 145 is S, position 155 is T, position 156 is H, position 157 is L, position 158 is N, position 171 is N, position 189 is K, position 193 is F, position 212 is A, or position 225 is D. In one embodiment, the mutant HA has non-immunodominant residues at two or more of positions 119, 123, 125, 126, 127, 129, 138, 140, 141, 151, 152, 153, 154, 155, 156, 185, or 189 in 115. In one embodiment, the residue in H5 at position 119 is not R, 123 is not P, 125 is not H, 126 is not E, 127 is not T, 129 is not L, 138 is not Q, 140 is not A, 141 is not S, 151 is not I, 152 is not K, 153 is not K, 154 is not N, 155 is not D, 156 is not A, 185 is not A, or 189 is not N. In one embodiment, the residue in H5 at position 119 is R, position 123 is P, position 125 is H, position 126 is E, position 127 is T, position 129 is L, position 138 is Q, position 140 is A, position 141 is S, position 151 is I, position 152 is K, position 153 is K, position 154 is N, position 155 is D, position 156 is A, position 185 is A, or position 189 is N. In one embodiment, the residue in H5 at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K, position 154 L, T, D, R, P, S, or H, position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H. In one embodiment, 2, 3, 4, 5, 6, 7, 8, 9, 10, 11, 12, 13, 14 15, 16, 17, 18, 19 or 20 of the codons that encode residues that form the immunodominant epitope are mutated. In one embodiment, the mutant HA has 2, 3, 4, 5, 6, 7, 8, 9, 10, 11, 12, 13, 14 15, 16, 17, 18, 19 or 20 non-immunodominant epitope residues. In one embodiment, the mutant HA has 10, 11, 12, 13, 14 15, 16, or 17 non-immunodominant epitope residues. In one embodiment, the mutant HA has 1, 2, 3, 4, 5, 6, 7, 8, 9, or 10, immunodominant epitope residues of the parent. In one embodiment, the mutant HA has 1, 2, 3, 4, or 5 immunodominant epitopes of the parent. In one embodiment, the nucleic acid molecules are identified using one or more antibodies that recognize conserved sub-dominant epitopes. In one embodiment, the cells encoding the nucleic acid molecules are identified as those that do not bind one or more antibodies that recognize immunodominant epitopes. In one embodiment, the nucleic acid molecule encoding the mutant hemagglutinin is sequenced.

In one embodiment, a method to prepare an influenza virus encoding a mutant hemagglutinin that has one or more altered residues in one or more immunodominant epitopes relative to a parental influenza virus is provided. The method includes introducing a plurality of mutations at residues that form an immunodominant domain of a HA of a parent influenza virus and isolating or preparing one or more influenza viruses with the mutated HA. In one embodiment, a plurality of mutations is introduced to antigenic sites A and/or B in HA, thereby forming a library of influenza viruses having mutant HAs. Viruses in the library having distinct mutations in antigenic sites A and/or B, e.g., those that have lower reactivity with sera that bind immunodominant epitopes in the parent HA, can be pooled to form a 'pan' HA sub-type specific vaccine. In one embodiment, a mutation is introduced in an H3 HA encoding nucleic acid molecule at two or more of residues 121, 131, 135, 138, 140, 142, 144, 145, 155, 156, 157, 158, 171, 189, 193, 212, or 225, to encode a residue that is not a residue that is part of an immunodominant epitope in the parent virus, and one or more influenza viruses with the mutated 113 HA are prepared. In one embodiment, a mutation is introduced in an H5 HA encoding nucleic acid molecule at two or more of residues 119, 123, 125, 126, 127, 129, 138, 140, 141, 151, 152, 153, 154, 155, 156, 185, or 189, wherein the mutations encode a residue that is not an immunodominant epitope; and to encode a residue that is not a residue that forms an immunodominant epitope for the parent virus, and one or more influenza viruses with the mutated H5 HA are prepared. In one embodiment, the residue in the mutated H3 HA at position 121 is Q, R, 1, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F. In one embodiment, the residue in 113 at position 121 is not N, position 131 is not T, position 135 is not T, position 138 is not A, position 140 is not I, position 142 is not R, position 144 is not S, position 145 is not S, position 155 is not T, position 156 is not H, position 157 is not L, position 158 is not N, position 171 is not N, position 189 is not K, position 193 is not F, position 212 is not A, or position 225 is not D. In one embodiment, the residue in H3 at position 121 is N, position 131 is T, position 135 is T, position 138 is A, position 140 is I, position 142 is R, position 144 is S, position 145 is S, position 155 is T, position 156 is H, position 157 is L, position 158 is N, position 171 is N, position 189 is K, position 193 is F, position 212 is A, or position 225 is D. In one embodiment, the residue at position 119 is not R, 123 is not P, 125 is not H, 126 is not E, 127 is not T, 129 is not L, 138 is not Q, 140 is not A, 141 is not S, 151 is not I, 152 is not K, 153 is not K, 154 is not N, 155 is not D, 156 is not A, 185 is not A, or 189 is not N. In one embodiment, the residue at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, 1, F, or D; position 153 is R, Q, T, N, S, F, P, V, or K; position 154 L, T, D, R, P, S, or H, position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H. In one embodiment, wherein the mutant HA has 2, 3, 4, 5, 6, 7, 8, 9, 10, 11, 12, 13, 14, 15, 16, or 17 different residues (non-immunodominant epitope residues) at the immunodominant epitope positions of the parent.

In one embodiment, a composition is provided comprising a plurality of distinct recombinant influenza viruses each encoding a hemagglutinin comprising non-immunodominant epitope residues at immunodominant epitope residue sites, e.g., antigenic sites A and/or B. Thus, the distinct recombinant influenza viruses have distinct mutations in antigenic sites A and/or B, e.g., those that have lower reactivity with sera that bind immunodominant epitopes in the parent HA, can be pooled to form a 'pan' HA sub-type specific vaccine. In another embodiment, the composition has a plurality of distinct recombinant influenza viruses each encoding a hemagglutinin comprising non-immunodominant epitope residues at immunodominant epitope residue sites, e.g., antigenic sites A and/or B, where at least two of the plurality encode different subtypes of hemagglutinin. In one embodiment, one of the plurality of influenza viruses comprises a non-immunodominant epitope at two or more of positions 121, 131, 135, 138, 140, 142, 144, 145, 155, 156, 157, 158, 171, 189, 193, 212, or 225 in H3. In one embodiment, one of the plurality of influenza viruses comprises a non-immunodominant epitope residue at two or more of positions 119, 123, 125, 126, 127, 129, 138, 140, 141, 151, 152, 153, 154, 155, 156, 185, or 189 in H5. In one embodiment, the composition has at least 2, 3, 4, 5, 6, 7, 8, 9, or 10 or more distinct recombinant influenza viruses.

Further provided is a method to immunize an animal, comprising: administering an effective amount of a composition comprising a plurality of the viruses described to an animal, e.g., a human, canine, feline, bovine, caprine, ovine, equine, swine, or avian.

In one embodiment, a method to prepare a plurality of influenza virus nucleic acid molecules encoding a hemagglutinin (HA) having one or more altered residues in one or more immunodominant epitopes is provided, comprising: introducing random mutations at a plurality of codons in one or more immunodominant epitopes in an isolated parental influenza virus nucleic acid molecule encoding an influenza virus hemagglutinin having at least two immunodominant epitopes, thereby providing a library of influenza virus nucleic acid molecules encoding a mutant influenza virus hemagglutinin; introducing the library into cells so as to provide a library of cells that express the mutant hemagglutinins; and identifying a mutant hemagglutinin encoded by the library with a reduced number of the immunodominant epitopes relative to the parental hemagglutinin as a result of one or more substitutions and/or deletions at residues that form the one or more immunodominant epitopes. In one embodiment, the mutations are introduced into immunodominant epitope (antigenic site) A, B, or A and B. In one embodiment, the mutations are introduced into immunodominant epitope C, D or E, or any combination thereof. In one embodiment, at least 5, 10, 15 or 20 codons, or any integer between 5 and 20, are mutated. In one embodiment, the mutant hemagglutinin is identified using antibodies or other hemagglutinin binding molecules. In one embodiment, at least one of the antibodies or other hemagglutinin binding molecules binds an immunodominant epitope in the parent hemagglutinin or a different influenza virus of the same HA sub-type. In one embodiment, the method includes contacting one or more members of the library with at least one antibody or other hemagglutinin binding molecule that binds a conserved region in the hemagglutinin stem. In one embodiment, the immunodominant epitope that is mutated corresponds to residues 121 to 146 in H3 HA (site A), residues 156 to 196 in H3 HA (site B), residues 50 to 57 or 275 to 279 in H3 HA (site C), residue 164, residue 182 or residues 208 to 217 in H3 HA (site D) or residues 62 to 83 in H3 HA (site E). In one embodiment, the cells are mammalian cells. In one embodiment, the hemagglutinin (HA) is H1, H2, H3, H5, H6, H7 or H9. In one embodiment the mutant HA has a substitution at two or more of positions 121, 131, 135, 138, 140, 142, 144, 145, 155, 156, 157, 158, 171, 189, 193, 212, or 225, or a deletion at one or more of positions 121, 131, 135, 138, 140, 142, 144, 145, 155, 156, 157, 158, 171, 189, 193, 212, or 225, in H3, or a combination thereof, relative to a parental HA. In one embodiment, the residue in H3 at position 121 is Q, R, I, L, V, S, F, Y or A, position 131 is R, V, S, Q, C, V, Y, D, E, or L, position 135 is Y, K, N, V, W, S, V, or P, position 138 is W, K, I, R, or L, position 140 is L, M, T, S, R K, M, or P, position 142 is N, G, Y, Q, E, H, N, L, or P, position 144 is T, V, G, D, H, L or Q, position 145 is P, R, W or K, position 155 is C, I, R, A, V, S or N, position 156 is P, G, S, T, A, or C, position 157 is D, P, S, G, 1, R or T, position 158 is R, V, S, A, K, C, Q, position 171 is T, F, L, E, H, C or R, position 189 is A, P, T, L, A, S, Y, or R, position 193 is Q, R, N, T, E, V, or P, position 212 is V, R, G, S, M, D or E, or position 225 is L, P, C, S, Q, G, Y, or F. In one embodiment, the mutant residue at position 121 is not N, position 131 is not T, position 135 is not T, position 138 is not A, position 140 is not I, position 142 is not R, position 144 is not S, position 145 is not S, position 155 is not T, position 156 is not H, position 157 is not L, position 158 is not N, position 171 is not N, position 189 is not K, position 193 is not F, position 212 is not A, or position 225 is not D. In one embodiment, the non-mutant residue at position 121 is N, position 131 is T, position 135 is T, position 138 is A, position 140 is I, position 142 is R, position 144 is S, position 145 is S, position 155 is T, position 156 is H, position 157 is L, position 158 is N, position 171 is N, position 189 is K, position 193 is F, position 212 is A, or position 225 is D. In one embodiment, the mutant HA has a substitution at two or more of positions 119, 123, 125, 126, 127, 129, 138, 140, 141, 151, 152, 153, 154, 155, 156, 185, or 189, or a deletion in one or more of positions 119, 123, 125, 126, 127, 129, 138, 140, 141, 151, 152, 153, 154, 155, 156, 185, or 18, in H5, or any combination thereof. In one embodiment, the mutant residue at position 119 is not R, 123 is not P, 125 is not H, 126 is not E, 127 is not T, 129 is not L, 138 is not Q, 140 is not A, 141 is not S, 151 is not I, 152 is not K, 153 is not K, 154 is not N, 155 is not D, 156 is not A, 185 is not A, or 189 is not N. In one embodiment, the non-mutant residue at position 119 is R, position 123 is P, position 125 is EH, position 126 is E, position 127 is T, position 129 is L, position 138 is Q, position 140 is A, position 141 is S, position 151 is I, position 152 is K, position 153 is K, position 154 is N, position 155 is D, position 156 is A, position 185 is A, or position 189 is N. In one embodiment, the residue at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q, position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S, or position 189 is Y, S, L, R, K, G, E, F, D, V, E, I, or H. In one embodiment, 2, 3, 4, 5, 6, 7, 8, 9, 10, 11, 12, 13, 14, 15, 16, or 17 of the codons that encode residues that form the immunodominant epitope are mutated. In one embodiment, the mutant HA has 2, 3, 4, 5, 6, 7, 8, 9, 10, 11, 12, 13, 14 15, 16, or 17 substitutions. In one embodiment, the mutant HA has 10, 11, 12, 13, 14 15, 16, or 17 substitutions. In one embodiment, the mutant HA has 1, 2, 3, 4, 5, 6, 7, 8, 9, or 10 residues in the one or more immunodominant epitopes that are not substituted or deleted. In one embodiment, the mutant HA has at least 10, 15, 20, 25, 30, 35, 40 or 45 residues in the immunodominant epitope that are not substituted or deleted. In one embodiment, the nucleic acid molecule encoding the mutant hemagglutinin is sequenced.

In one embodiment, a method to prepare an influenza virus encoding a mutant hemagglutinin with altered immunodominant epitopes relative to a parental influenza virus is provided, comprising: introducing a mutation in a parental H3 HA nucleic acid molecule at two or more codons for residue 121, 131, 135, 138, 140, 142, 144, 145, 155, 156, 157, 158, 171, 189, 193, 212, or 225, wherein the mutation encodes a residue that is not an immunodominant epitope residue in the parent H3 HA; and isolating or preparing one or more influenza viruses with the mutated H3 HA. In one embodiment, the mutated H3 is recognized by antibodies that bind sub-dominant epitopes but not antibodies that bind the immunodominant epitope. In one embodiment, the residue in the mutated H3 HA at position 121 is Q, R, 1, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F. In one embodiment, the residue in H3 at position 121 is not N, position 131 is not T, position 135 is not T, position 138 is not A, position 140 is not I, position 142 is not R, position 144 is not S, position 145 is not S, position 155 is not T, position 156 is not H, position 157 is not L, position 158 is not N, position 171 is not N, position 189 is not K, position 193 is not F, position 212 is not A, or position 225 is not D. In one embodiment, the residue in H3 at position 121 is N, position 131 is T, position 135 is T, position 138 is A, position 140 is 1, position 142 is R, position 144 is S, position 145 is S, position 155 is T, position 156 is H, position 157 is L, position 158 is N, position 171 is N, position 189 is K, position 193 is F, position 212 is A, or position 225 is D.

In one embodiment, a method to prepare an influenza virus encoding a mutant hemagglutinin with altered immunodominant epitopes relative to a parental influenza virus is provided, comprising: introducing a mutation in a parental H5 HA nucleic acid molecule at two or more codons for residue 119, 123, 125, 126, 127, 129, 138, 140, 141, 151, 152, 153, 154, 155, 156, 185, or 189, wherein the mutation encodes a residue that is not an immunodominant epitope residue in the parent H5HA; and isolating or preparing influenza viruses with the mutated H5 HA. In one embodiment, the mutated H5 is recognized by antibodies that bind sub-dominant epitopes but not antibodies that bind the immunodominant epitope. In one embodiment, the residue at position 119 is not R, 123 is not P, 125 is not H1, 126 is not E, 127 is not T, 129 is not L, 138 is not Q, 140 is not A, 141 is not S, 151 is not I, 152 is not K, 153 is not K, 154 is not N, 155 is not D, 156 is not A, 185 is not A, or 189 is not N. In one embodiment, the residue at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, 1, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H. In one embodiment, the mutant HA has 2, 3, 4, 5, 6, 7, 8, 9, 10, 11, 12, 13, 14, 15, 16, or 17 substitutions.

In one embodiment, a composition is provided comprising a plurality of distinct recombinant influenza H3 viruses each encoding a hemagglutinin comprising a plurality of antigenically distinct residues relative to residues that form an immunodominant epitope in a parent virus, wherein each of the plurality of influenza viruses comprises substitutions at two or more positions 121, 131, 135, 138, 140, 142, 144, 145, 155, 156, 157, 158, 171, 189, 193, 212, or 225, or one or more deletions of positions 121, 131, 135, 138, 140, 142, 144, 145, 155, 156, 157, 158, 171, 189, 193, 212, or 225, in H3, or any combination thereof. In one embodiment, the composition has at least three, four or five distinct viruses with the substitutions. In one embodiment, the composition has five to ten distinct viruses with the substitutions. In one embodiment, the composition has ten to twenty distinct viruses with the substitutions. In one embodiment, each distinct virus has at least one to five substitutions in antigenic site A or site B. In one embodiment, each distinct virus has at least one to ten substitutions in antigenic sites A and B. In one embodiment, each distinct virus has altered binding to antibodies that bind the corresponding parental hemagglutinin.

In one embodiment, a composition is provided comprising a plurality of distinct recombinant influenza H5 viruses each encoding a hemagglutinin comprising antigenically distinct residues relative to residues that form an immunodominant epitope in a parent virus, wherein each of the plurality of influenza viruses comprises a substitution at two or more of positions 119, 123, 125, 126, 127, 129, 138, 140, 141, 151, 152, 153, 154, 155, 156, 185, or 189, or a deletion in one or more of positions 119, 123, 125, 126, 127, 129, 138, 140, 141, 151, 152, 153, 154, 155, 156, 185, or 189, in H5, or any combination thereof. In one embodiment, the composition has at least three, four or five distinct viruses with the substitutions. In one embodiment, the composition has five to ten distinct viruses with the substitutions. In one embodiment, the composition has ten to twenty distinct viruses with the substitutions. In one embodiment, each distinct virus has at least one to five substitutions in antigenic site A or site B. In one embodiment, each distinct virus has at least one to ten substitutions in antigenic sites A and B. In one embodiment, wherein each distinct virus has altered binding to antibodies that bind the corresponding parental virus. In one embodiment, the composition has at least 2, 3, 4, 5, 6, 7, 8, 9, or 10 or more distinct recombinant influenza viruses.

In one embodiment a method to immunize an animal is provided, comprising: administering an effective amount of a composition described herein to an animal.

In one embodiment, an isolated influenza virus is provided comprising a H5 HA wherein the residue at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or 11, or any combination of those residues at those positions.

In one embodiment, a composition is provided comprising a plurality of distinct influenza viruses comprising a H5 HA wherein the residue at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H, position 155 is N, G, K, H, T, L, S, I, P, or Q; position 156 is T, F, R, S, D, P, H, G, A, or N, position 185 is L, D, N, G, E, F, S, L, Q, P, V, M, R, A, or S; or position 189 is Y, S, L, R, K, G, E, F, D, V, E, I, or H, or any combination of those residues at those positions.

In one embodiment, an isolated influenza virus is provided comprising a H3 HA wherein the residue at position 121 is Q, R, I, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F, or any combination of those residues at those positions.

In one embodiment, a composition is provided comprising a plurality of distinct influenza viruses comprising a H3 HA wherein the residue at position 121 is Q, R, I, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F, or any combination of those residues at those positions.

The invention will be described by the following non-limiting examples.

Example 1

VLPs can be generated by expressing influenza HA together with a single viral matrix protein, hence, the immune responses to the other influenza viral proteins, such as M1 and NA, will not affect the interpretation of the results. VLPs based on the Ebola virus VP40 matrix protein are employed because humans do not possess antibodies to VP40, and Ebola VP40-based VLPs expressing HA are efficiently formed.

17 amino acid positions were identified in human H3 HA proteins that are known or expected to affect antigenicity (e.g., positions 121, 131, 135, 138, 140, 142, 144, 145, 155, 156, 157, 158, 171, 189, 193, 212, and 225; see FIG. 1) and gene 'libraries' were prepared that encode all 20 amino acids at each of the 17 positions (resulting in $20^{17}$ theoretically possible variants) in the genetic background of A/Tokyo/UT-IMS2-1/2014 (a clade 3c.2a virus). Virus libraries possessing the up to '17-amino acid mutant HA' proteins were generated and screened with human sera to identify antigenic escape mutants. It was found that HA proteins with up to 17 amino acid changes in their antigenic epitopes were functional and antigenically distinct from the parental virus.

The '17-amino acid mutant HA' proteins may elicit broadly protective immune responses. Immunization with a mixture of HAs with up to 17 amino acid changes at positions responsible for the immune-dominance of the HA head, are unlikely to induce antibodies to the immune-dominant HA epitopes. Rather, stronger responses may be elicited to non-dominant epitopes, resulting in increased cross-protective immunity compared to current vaccines. The use of such vaccines may overcome immunological imprinting (immune response biased towards the first influenza virus encountered).

Specifically, VLP libraries with randomized sequences at 17 amino acid positions of the HA protein of the A/California/7/2004 (Cal/04) virus, a representative of the 'California/2004' antigenic cluster of human H3 viruses are prepared. As a control, VLPs containing wild-type HA protein are also generated. All VLPs are treated with sialidase to prevent self-aggregation. VLPs containing wild-type or '17-amino acid mutant HA' proteins are tested for their reactivity with monoclonal antibodies to the HA head and stalk (e.g., >20 and >10 monoclonal antibodies that react with the head or stalk, respectively, of Cal/04 virus). Compared with VLPs containing wild-type HA, VLPs containing the '17-amino acid mutant HA' proteins likely show reduced binding to antibodies that interact with the HA head, whereas the level of binding to antibodies that interact with the HA stalk is expected to be similar between the two VLPs.

To test the immunogenicity and protective efficacy of the H3 HA-VLPs against antigenically diverse human H3 viruses, ferrets are immunized twice with Cal/04 H3 HA-VLPs; four weeks after the second immunization, the antibody titers against VLPs containing wild-type HA or '17-amino acid mutant HA' proteins are tested. Ferrets are challenged with homologous Cal/04 virus or with three different human H3 influenza viruses belonging to more recent antigenic clusters (e.g., the 'Perth/2009', 'Victoria/2012', and current 3c.2a1 clades). Virus titers in nasal swabs are tested by using plaque assays. Alternatively, or in addition, ferrets are "pre-immunized" with VLPs containing the HA proteins of the 'Wuhan/1995', 'Sydney/1997', and 'Fujian/2002 cluster (ferrets are immunized sequentially with these VLPs; immunizations will be two weeks apart). After the three sequential 'pre-immunizations', animals are vaccinated with VLPs containing wild-type Cal/04 or '17-amino acid mutant Cal/04 HA' proteins and the animals are challenged as described above in order to establish whether a vaccine that elicits antibodies to non-dominant epitopes can overcome immunogenic imprinting.

Immunization with wild-type virus protects ferrets against infection with homologous virus, but not against infection with antigenic drift variants that belong to different antigenic clades. Ferrets immunized with '17-amino acid mutant' H3 HA-VLPs are better protected than those immunized with the wild-type virus against antigenically drifted human H3N2 influenza viruses which establishes that immunization with '17-amino acid mutant HA' proteins elicits broadly protective antibodies, perhaps because immune responses are 'refocused' towards non-dominant epitopes that are more conserved among human H3 viruses than the major immune-dominant epitopes.

Individual mutants and/or libraries in which fewer amino acid positions are randomized allow for the identification of specific mutant HA proteins that elicit cross-protective immune responses to non-dominant epitopes.

Example 2

Generation and In Vitro Characterization of HAs with Multiple Mutations in Immunodominant Epitopes (ID-EpiMut HAs)

Given that the first exposure to previously unencountered HAs elicits high levels of Abs to conserved, immune-subdominant HA epitopes, mixtures of viruses encoding non-naturally occurring immunodominant head epitopes (i.e., immunodominant epitope-mutated HA, ID-EpiMut HA) are prepared. Each of these variants is an unique HA to the immune system, thereby boosting the levels of cross-protective antibodies to the conserved, immune-subdominant regions in HA.

Experimental Approach. Millions of mutant influenza viruses are generated ('virus libraries'), and variants with the desired properties, such as non-naturally occurring immunodominant head epitopes, are selected.

Generation and screening of virus libraries. Methods to generate influenza virus 'libraries', as well as other viral libraries including Ebola VIP libraries, that is, mixtures of viruses possessing random mutations at arbitrary or predetermined amino acid positions of an influenza viral protein, are available ((Li et al., 2016; Ping et al., 2015 and 2016; Taft et al., 2015). Briefly, mutations at predetermined positions of influenza viral cDNAs are introduced by PCR with degenerate oligonucleotides encoding 'NNN' at the targeted codon, or by commercial gene synthesis. The resulting PCR or gene mixtures are cloned into RNA polymerase I vectors for the transcription of influenza viral RNAs, resulting in so-called 'plasmid libraries'. Following established reverse genetics protocols, eukaryotic cells (e.g., 293T human embryonic fibroblast cells) are transfected with the plasmid library, seven RNA polymerase I plasmids for the transcription of the remaining seven viral RNA segments (the genome of influenza A viruses comprises eight segments of single-stranded RNA), and four protein expression plasmids synthesizing the viral polymerase proteins (PB2, PB1, PA) and nucleoprotein (NP), which are all essential to initiate viral replication and transcription. This approach results in the generation of virus libraries composed of millions of mutants.

While classic experimental approaches test one mutation at a time, the present approach allows the simultaneous testing of millions of mutants. Hence, the approach (i) recapitulates multiple steps of evolution in an experimental setting; (ii) covers a large 'sequence space' (including mutants that have not been isolated in nature; (iii) allows for competition among mutants (a critical aspect in virus evolution); and (iv) eliminates non-viable mutants at the stage of virus library generation. Virus libraries are then screened for different biological features including antigenicity, receptor-binding properties, polymerase activity, and virus titers. The power and versatility of this approach has been shown by modeling the antigenic evolution of seasonal human H1N1 and H3N2 influenza viruses (Li et al., 2016), isolating polymerase mutants that confer efficient replication to avian influenza viruses in mammalian cells (an important feature in the generation of pandemic influenza viruses) (Taft et al., 2016), and by selecting mutations that increase the titers of influenza A and B vaccine viruses (Ping et al., 2015 and 2016).

Generation and screening of H5 HA virus libraries. To better understand the antigenic differences among pandemic H5N1 influenza viruses, random mutations were introduced at 17 amino acid positions that are known or suspected to affect the antigenic properties of these viruses (e.g., amino acid positions 119, 123, 125, 126, 127, 129, 138, 140, 141, 151, 152, 153, 154, 155, 156, 185, and 189; numbers refer to the amino acid position of mature H5 protein after the signal peptide has been removed); these positions cluster in the highly variable, immunodominant major antigenic head epitopes of H5N1 viruses. Chemically synthesized gene libraries were obtained which, theoretically, encode all 20 amino acids at each of the 17 selected positions. Gene libraries were amplified by PCR, the PCR products cloned into an RNA polymerase I vector, and H5N1 virus libraries generated. In general, the size of the virus libraries ranges from $\sim 10^4$-$10^7$ plaque forming units (pfu)/ml of supernatant derived from transfected cells; they do not, therefore, contain all possible combinations of amino acids at the 17 selected positions (i.e., $20^{17}$ different amino acid combinations).

After generating H5 virus libraries with random mutations at 17 amino acid positions in HA, they were incubated with ferret sera raised against different H5 viruses. During this selection step, mutants with antigenic properties similar to recently circulating H5 viruses will be neutralized. The resulting antigenic escape variants were plaque-purified in Madin-Darby canine kidney (MDCK) cells (a cell line commonly used for influenza virus propagation), and individual viruses were amplified and sequenced to identify the amino acid changes that conferred antigenic escape. After antigenic selection, >50 H5 mutants with 13-17 amino acid differences from the parent virus were isolated (see Table 1 for examples of selected sequences), attesting to the sequence plasticity of the highly variable, immunodominant major antigenic head epitopes. Importantly, most of these mutants are antigenically different from the parent virus as demonstrated by hemagglutination inhibition assays. Likewise, studies with seasonal human H3N2 virus (see Example 1 and Table 1B-C) yielded mutants that possessed multiple amino acid changes in the highly variable, immunodominant antigenic head epitopes and are antigenically distinct from the parent virus. Collectively, these studies establish that seasonal H3N2 and pandemic H5 viruses with up to 17 amino acid mutations in immunodominant antigenic epitopes are viable, replicate efficiently, and are antigenically distinct from the parent virus.

TABLE 1

Sequences of H5 HA proteins with randomized amino acids at the indicated positions

|    | 119 | 123 | 125 | 126 | 127 | 129 | 138 | 140 | 141 | 151 | 152 | 153 | 154 | 155 | 156 | 185 | 189 |
|----|-----|-----|-----|-----|-----|-----|-----|-----|-----|-----|-----|-----|-----|-----|-----|-----|-----|
| WT | R   | P   | H   | E   | T   | L   | Q   | A   | S   | I   | K   | K   | N   | D   | A   | A   | N   |
| 1  | R   | L   | L   | S   | V   | D   | G   | T   | S   | T   | A   | R   | L   | N   | T   | L   | Y   |
| 2  | L   | Y   | L   | S   | V   | L   | G   | G   | R   | T   | P   | Q   | T   | D   | F   | D   | S   |
| 3  | L   | I   | D   | R   | V   | S   | D   | S   | P   | S   | A   | Q   | N   | G   | R   | D   | L   |
| 4  | K   | M   | N   | S   | V   | G   | E   | R   | P   | T   | T   | T   | N   | K   | A   | N   | L   |
| 5  | R   | N   | D   | S   | A   | K   | L   | R   | P   | T   | Y   | T   | N   | H   | S   | G   | R   |
| 6  | S   | M   | G   | I   | S   | K   | A   | R   | S   | L   | T   | N   | T   | T   | D   | N   | L   |
| 7  | R   | L   | G   | S   | M   | W   | M   | D   | W   | Y   | H   | T   | T   | L   | P   | E   | R   |
| 8  | S   | L   | L   | S   | V   | R   | L   | K   | K   | E   | S   | D   | N   | H   | F   | L   |     |
| 9  | G   | S   | W   | G   | L   | E   | L   | R   | R   | N   | S   | F   | N   | S   | P   | S   | Y   |
| 10 | G   | V   | W   | N   | L   | V   | L   | Q   | S   | T   | S   | T   | L   | I   | P   | L   | K   |
| 11 | T   | Y   | M   | S   | L   | R   | V   | Q   | E   | I   | P   | S   | R   | D   | R   | Q   | E   |
| 12 | E   | Y   | I   | S   | L   | L   | D   | R   | A   | T   | A   | P   | R   | P   | T   | L   | G   |
| 13 | S   | K   | R   | S   | V   | L   | M   | R   | E   | T   | A   | V   | P   | T   | G   | P   | S   |

TABLE 1-continued

Sequences of H5 HA proteins with randomized amino acids at the indicated positions

| | 119 | 123 | 125 | 126 | 127 | 129 | 138 | 140 | 141 | 151 | 152 | 153 | 154 | 155 | 156 | 185 | 189 |
|---|---|---|---|---|---|---|---|---|---|---|---|---|---|---|---|---|---|
| WT | R | P | H | E | T | L | Q | A | S | I | K | K | N | D | A | A | N |
| 14 | A | G | K | Q | L | Q | F | R | A | Q | S | K | R | P | A | S | F |
| 15 | L | G | F | A | M | A | L | R | M | K | P | K | T | P | N | V | D |
| 16 | V | G | G | S | K | R | R | E | M | T | S | T | S | D | R | L | G |
| 17 | F | S | A | N | A | I | S | E | E | I | F | K | N | Q | T | M | V |
| 18 | R | T | F | G | A | F | A | C | D | T | I | T | H | P | T | R | E |
| 19 | N | R | D | R | F | L | A | V | L | L | P | K | S | D | T | A | I |
| 20 | T | R | S | G | Y | F | M | G | Q | Q | D | Q | S | Q | H | S | H |

TABLE 1B

Sequence of TK/2 17AA (H3) mutants

| Short name TK2 | Position (H3 Numbering) | | | | | | | | | | | | | | | Note | FFU/50 ul |
|---|---|---|---|---|---|---|---|---|---|---|---|---|---|---|---|---|---|
| | 121 | 131 | 135 | 138 | 140 | 142 | 144 | 145 | 155 | 156 | 157 | 158 | 171 | 189 | 193 | 212 | 225 |
| | N | T | T | A | I | R | S | S | T | H | L | N | N | K | F | A | D |
| TK2-17AA-mut-1 | Y | V | V | K | W | S | G | P | V | G | V | R | D | N | A | Q | K | | 8.05E+04 |
| TK2-17AA-mut-2 | M | V | G | D | F | T | D | R | C | A | N | G | R | E | G | N | K | | 1.08E+05 |
| TK2-17AA-mut-4 | K | R | G | . | P | D | A | G | M | T | S | P | K | D | G | L | E | | 7.91E+04 |
| TK2-17AA-mut-5 | Q | R | Y | K | L | N | T | P | C | P | D | R | T | A | Q | V | L | | 2.92E+06 |
| TK2-17AA-mut-6 | V | R | R | F | M | N | T | W | V | A | . | H | T | I | S | R | P | | 4.46E+04 |
| TK2-17AA-mut-7 | F | G | V | . | K | A | M | L | I | L | S | G | . | — | — | S | . | Plus deletion of additional amino acids | 1.85E+05 |
| TK2-17AA-mut-9 | V | K | V | T | H | E | R | R | A | S | P | V | R | R | T | I | S | | 1.12E+05 |
| TK2-17AA-mut-10 | R | V | K | W | M | G | V | P | I | G | P | V | F | T | R | R | P | | 6.16E+05 |
| TK2-17AA-mut-11 | T | G | L | R | C | S | G | R | Y | P | . | Q | T | F | A | R | T | | 4.37E+04 |
| TK2-17AA-mut-12 | I | . | N | K | T | Y | D | . | R | S | S | S | F | A | Q | G | C | | 2.37E+05 |
| TK2-17AA-mut-14 | V | M | L | K | T | G | A | W | Q | S | R | L | Q | L | R | R | E | | 3.03E+04 |
| TK2-17AA-mut-15 | A | K | S | R | N | D | G | V | R | S | R | F | T | E | A | Y | G | | 1.17E+05 |
| TK2-17AA-mut-16 | V | C | N | I | K | . | P | D | A | A | G | A | L | A | P | S | S | | 2.34E+05 |
| TK2-17AA-mut-17 | V | C | L | L | R | F | K | T | I | P | S | P | Q | N | S | T | S | | 1.91E+04 |
| TK2-17AA-mut-21 | V | R | V | V | V | D | P | R | G | S | C | I | I | — | — | — | — | Plus deletion of additional amino acids | 5.51E+04 |
| TK2-17AA-mut-22 | S | S | . | K | S | Q | G | . | R | P | I | K | E | P | N | V | Q | | 3.59E+05 |
| TK2-17AA-mut-23 | V | Q | V | R | R | E | H | . | V | T | . | R | H | L | T | M | G | | 1.16E+06 |

TABLE 1B-continued

Sequence of TK/2 17AA (H3) mutants

| Short name TK2 | 121 N | 131 T | 135 T | 138 A | 140 I | 142 R | 144 S | 145 S | 155 S | 156 H | 157 T | 158 L | 171 N | 189 N | 193 K | 212 F | 225 A | 225 D | Note | FFU/50 ul |
|---|---|---|---|---|---|---|---|---|---|---|---|---|---|---|---|---|---|---|---|---|
| TK2-17AA-mut-24 | L | R | N | T | K | T | N | . | Q | K | R | F | S | . | T | V | S | | | 1.65E+05 |
| TK2-17AA-mut-25 | R | R | I | V | N | G | T | R | W | P | S | P | R | S | S | V | R | | | 1.11E+05 |
| TK2-17AA-mut-26 | V | R | Y | K | T | A | E | Q | . | L | W | G | R | Y | Q | M | N | | | 1.13E+05 |
| TK2-17AA-mut-28 | F | D | S | K | G | N | V | K | P | T | R | R | L | S | — | P | S | | | 3.79E+04 |
| TK2-17AA-mut-29 | S | R | K | T | N | . | A | P | Q | . | M | K | F | T | N | F | C | | | 8.16E+04 |
| TK2-17AA-mut-30 | F | V | W | S | M | H | Q | P | Q | G | R | C | T | S | E | . | Y | | | 3.35E+05 |
| TK2-17AA-mut-31 | R | V | V | . | T | A | E | G | S | I | P | M | C | S | G | L | C | | | 1.02E+05 |
| TK2-17AA-mut-32 | F | D | G | F | . | N | . | W | R | A | S | Q | V | Y | R | V | L | | | 6.94E+05 |
| TK2-17AA-mut-34 | I | Y | S | R | Y | . | L | . | S | C | S | . | L | R | V | S | S | | | 3.13E+05 |
| TK2-17AA-mut-35 | I | M | Q | W | A | V | E | K | E | K | E | C | G | T | S | P | S | | | 1.29E+05 |
| TK2-17AA-mut-36 | H | G | S | R | K | M | G | E | K | R | K | Q | K | A | K | C | S | | | 5.46E+03 |
| TK2-17AA-mut-37 | R | A | V | R | N | N | K | Q | V | R | I | S | S | G | S | T | A | | | 4.05E+04 |
| TK2-17AA-mut-38 | I | E | R | G | D | P | P | N | V | G | E | H | R | R | . | S | C | | | 1.01E+05 |
| TK2-17AA-mut-39 | V | E | A | E | L | A | I | N | S | E | E | C | L | N | S | C | H | | | 1.47E+05 |
| TK2-17AA-mut-40 | T | I | A | R | C | S | K | P | R | N | R | T | R | V | K | T | V | | | 5.09E+04 |
| TK2-17AA-mut-41 | V | D | C | S | L | G | Q | F | P | L | R | R | L | N | S | W | C | | | 4.81E+04 |
| TK2-17AA-mut-43 | V | K | A | Q | M | . | . | K | S | S | A | I | R | A | M | S | . | | | 1.57E+05 |
| TK2-17AA-mut-44 | I | G | G | R | . | D | . | P | I | P | P | G | L | E | V | L | . | | | 8.63E+04 |
| TK2-17AA-mut-45 | M | N | S | T | R | H | K | . | C | D | T | Q | V | S | P | I | P | | | 2.33E+05 |
| TK2-17AA-mut-46 | Y | L | Q | T | F | . | G | A | A | C | A | H | T | N | L | F | C | | | 4.31E+04 |
| TK2-17AA-mut-47 | V | N | L | L | A | T | T | . | K | R | A | R | R | V | P | P | P | | | 1.03E+05 |
| TK2-17AA-mut-48 | F | R | S | V | V | Q | R | P | D | G | N | T | M | T | G | R | M | | | 2.04E+05 |
| TK2-17AA-mut-50 | V | C | P | L | W | H | Q | P | G | S | T | H | T | R | K | R | C | | | 3.43E+04 |

TABLE 1B-continued

Sequence of TK/2 17AA (H3) mutants

| Short name TK2 | 121 N | 131 T | 135 T | 138 A | 140 I | 142 R | 144 S | 145 S | 155 T | 156 H | 157 L | 158 N | 171 N | 189 K | 193 F | 212 A | 225 D | Note | FFU/50 ul |
|---|---|---|---|---|---|---|---|---|---|---|---|---|---|---|---|---|---|---|---|
| TK2-17AA-mut-51 | M | K | Y | Q | Y | I | N | H | S | P | F | R | F | I | D | F | C | | 1.05E+05 |
| TK2-17AA-mut-53 | T | N | C | R | W | N | K | C | I | . | P | L | K | H | N | V | Q | | 1.45E+05 |
| TK2-17AA-mut-54 | V | R | N | C | F | N | T | P | L | I | P | K | R | H | A | R | L | | 4.86E+04 |
| TK2-17AA-mut-55 | Y | R | P | . | N | K | T | R | N | . | P | A | T | H | N | E | L | C139Δ | 1.98E+05 |
| TK2-17AA-mut-56 | R | . | Q | S | C | Q | T | T | A | P | . | S | R | G | N | V | S | | 4.18E+04 |
| TK2-17AA-mut-57 | T | S | D | . | G | N | Y | A | P | F | S | G | L | I | D | V | C | | 3.35E+04 |
| TK2-17AA-mut-58 | F | H | M | R | L | N | N | T | R | R | C | G | H | T | K | G | A | | 2.87E+04 |
| TK2-17AA-mut-59 | H | R | R | R | M | G | N | D | Y | S | R | P | I | L | T | V | A | | 6.30E+04 |
| TK2-17AA-mut-60 | T | Q | S | Q | E | Q | I | R | . | S | K | G | I | T | R | L | W | | 7.46E+04 |
| TK2-17AA-mut-61 | V | S | K | D | H | K | A | G | R | D | R | K | T | V | K | W | S | G209D | 6.47E+04 |
| TK2-17AA-mut-64 | L | G | A | Q | R | Q | E | A | S | D | R | R | E | R | G | V | M | | 2.31E+05 |
| TK2-17AA-mut-65 | F | R | V | . | Q | . | E | P | M | T | T | H | T | Q | T | R | F | | 1.95E+05 |
| TK2-17AA-mut-66 | Y | E | P | L | L | Q | . | N | . | S | T | G | R | S | P | D | P | | 3.34E+05 |
| TK2-17AA-mut-67 | L | E | S | V | R | Y | N | D | R | G | P | P | T | A | R | E | I | | 1.33E+05 |
| TK2-17AA-mut-68 | I | S | G | L | R | P | G | V | S | W | D | P | . | N | R | E | T | | 2.79E+05 |
| TK2-17AA-mut-70 | W | E | S | W | K | H | R | P | L | T | T | K | V | I | R | L | P | | 6.00E+04 |
| TK2-17AA-mut-71 | E | Q | E | L | Q | D | M | A | V | P | Q | G | F | P | M | . | E | | 3.88E+05 |
| TK2-17AA-mut-72 | T | R | M | R | Q | N | Y | P | W | I | S | K | W | E | R | S | P | | 1.25E+04 |
| TK2-17AA-mut-73 | S | L | S | R | L | E | W | P | G | Q | R | T | L | T | S | R | A | | 2.10E+05 |
| TK2-17AA-mut-75 | F | R | N | E | R | N | P | T | I | P | V | S | L | S | A | S | C | | 2.02E+05 |
| TK2-17AA-mut-76 | E | R | K | L | L | N | N | G | . | Q | . | S | A | S | D | . | A | | 9.73E+04 |
| TK2-17AA-mut-77 | A | L | V | I | P | . | K | . | S | T | Q | Q | L | R | P | E | F | | 6.92E+05 |
| TK2-17AA-mut-79 | L | G | L | D | D | A | . | P | D | K | P | C | R | S | N | R | A | | 1.52E+05 |

'.' Same amino acid as wild-type; '—' Deletion.

TABLE 1C

Sequence of H3 mutants with deletions

| Virus | 185 | 186 | 187 | 188 | 189 | 190 | 191 | 192 | 193 | 194 | 195 | 196 | 197 | 198 | 199 | 200 | 201 | 202 |
|---|---|---|---|---|---|---|---|---|---|---|---|---|---|---|---|---|---|---|
| Tokyo 2 | P | G | T | D | K | D | Q | I | F | L | Y | A | Q | S | S | G | R | I |
| TK2-28 | . | . | . | . | S | A | N | L | — | A | V | . | . | . | . | . | . | . |
| TK2-7 | . | — | — | — | — | — | — | — | — | — | — | — | — | — | — | — | — | — |
| TK2-21 | . | . | T | D | — | — | — | — | — | — | — | — | — | — | — | — | . | K |

| Virus | 203 | 204 | 205 | 206 | 207 | 208 | 209 | 210 | 211 | 212 | 213 | 214 | 215 |
|---|---|---|---|---|---|---|---|---|---|---|---|---|---|
| Tokyo 2 | T | V | S | T | K | R | S | Q | Q | A | V | I | P |
| TK2-28 | . | . | . | . | . | . | . | . | . | P | . | . | . |
| TK2-7 | . | . | . | . | . | . | . | . | . | S | . | . | . |
| TK2-21 | N | H | . | I | Y | Q | K | K | — | — | — | — | . |

'.' Same amino acid as wild-type; '—' Deletion.

Selection of HA positions for mutagenesis. H3N2 HA variants with non-naturally occurring immunodominant antigenic head epitopes are generated so that vaccination with mixtures of these viruses dilutes the antibody responses to the immunodominant epitopes and focus the immune responses towards more conserved immune-subdominant epitopes in the head and stem regions of HA.

Figures 3A, 3B, 3C, 3D:
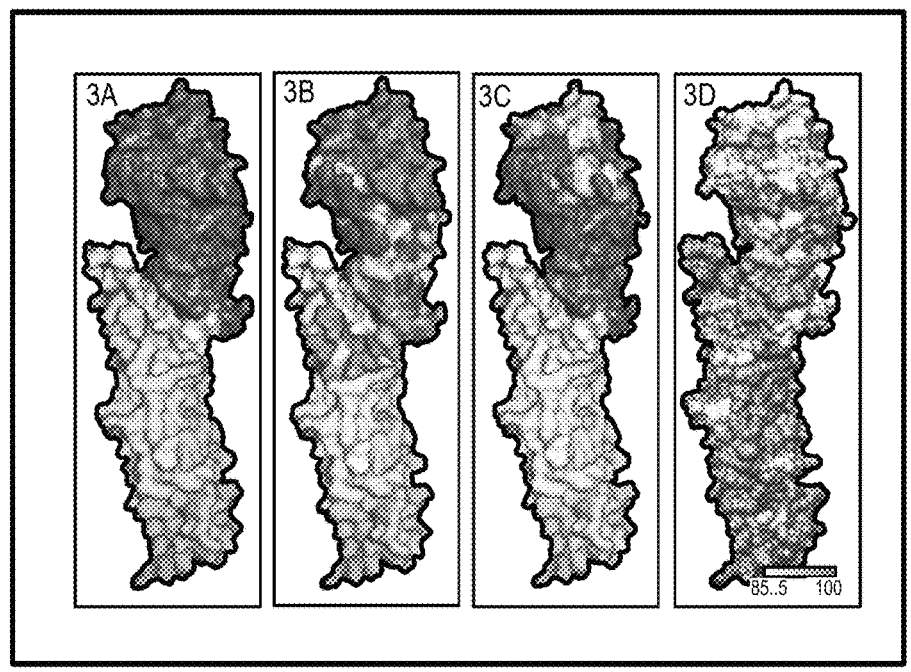
FIGS. 3A-D. Three-dimensional structure of H3 HA (4O5N). Shown are the head (dark gray) and stem (light gray) regions (A); the five major epitopes A (red), B (blue), C (orange), D (yellow), and E (green) (B); the amino acid positions selected for mutagenesis (wheat), see C.1.2.1 (C); and the sequence conservation of >13,000 unique human H3N2 HA sequences downloaded from the Influenza Research Database (D); the color scale indicates the amino acid sequence conservation at the respective position from 85.5% (gold) to 100% (purple). Shown in magenta is the highly conserved tyrosine residue at position 98 in the receptor-binding pocket.
Figures 4A, 4B:
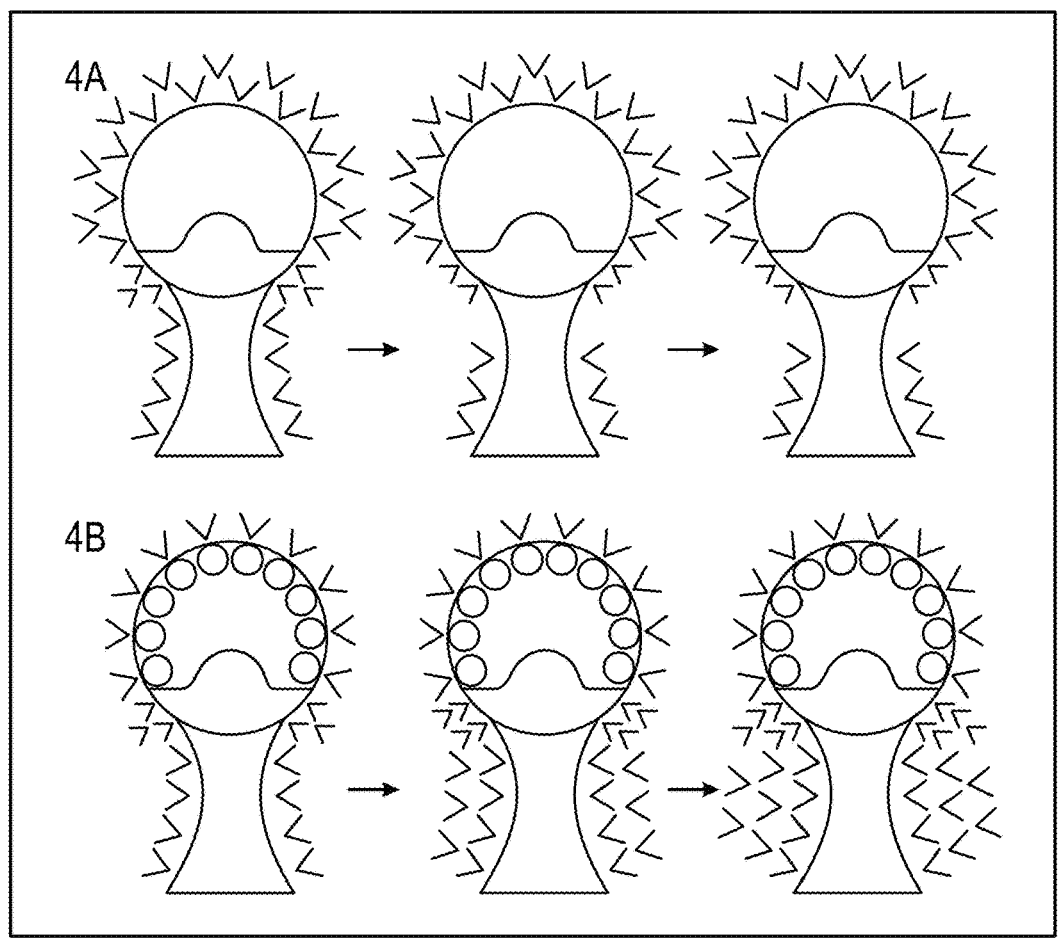
FIGS. 4A-4B. Schematic overview of the proposed strategy to elicit increased amounts of broadly-reactive Abs to immune-subdominant epitopes. (A) Subsequent infections or vaccinations with seasonal influenza viruses result in large amounts of Abs to the highly variable, immunodominant epitopes (shown in blue, dark green, and light green for three consecutive clusters), but consecutively lower amounts of Abs to the immune-subdominant epitopes in the stem (black) and head (dark gray). (B) New concept in which (repeat) immunizations with mixtures of HA proteins (shown here is only one mutant HA) with highly mutated, non-naturally occurring immunodominant antigenic epitopes are used to dilute the immune responses to the immunodominant epitopes, thereby boosting the levels of antibodies directed against immune-subdominant epitopes.
Figure 11A:
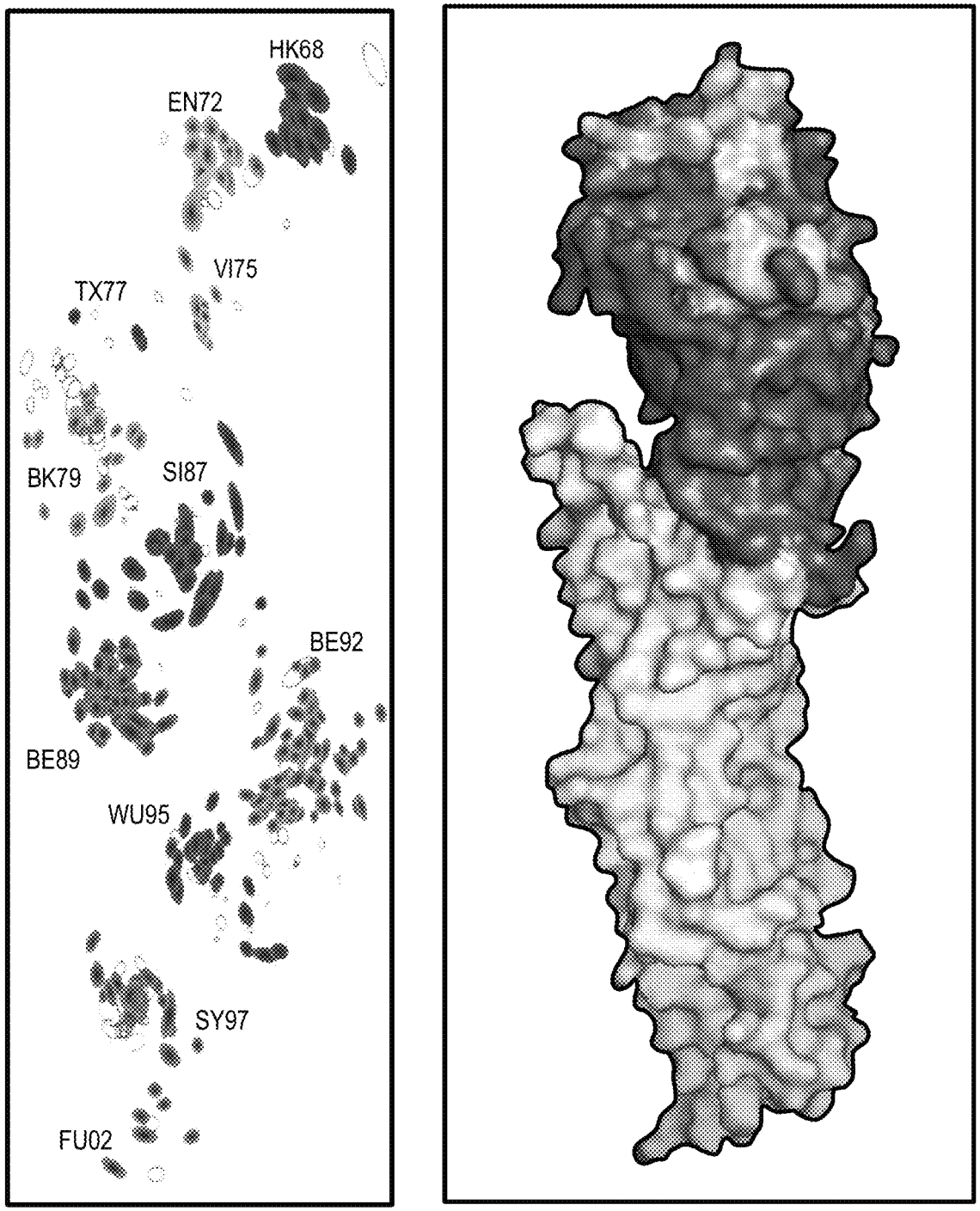
Figure 12A:
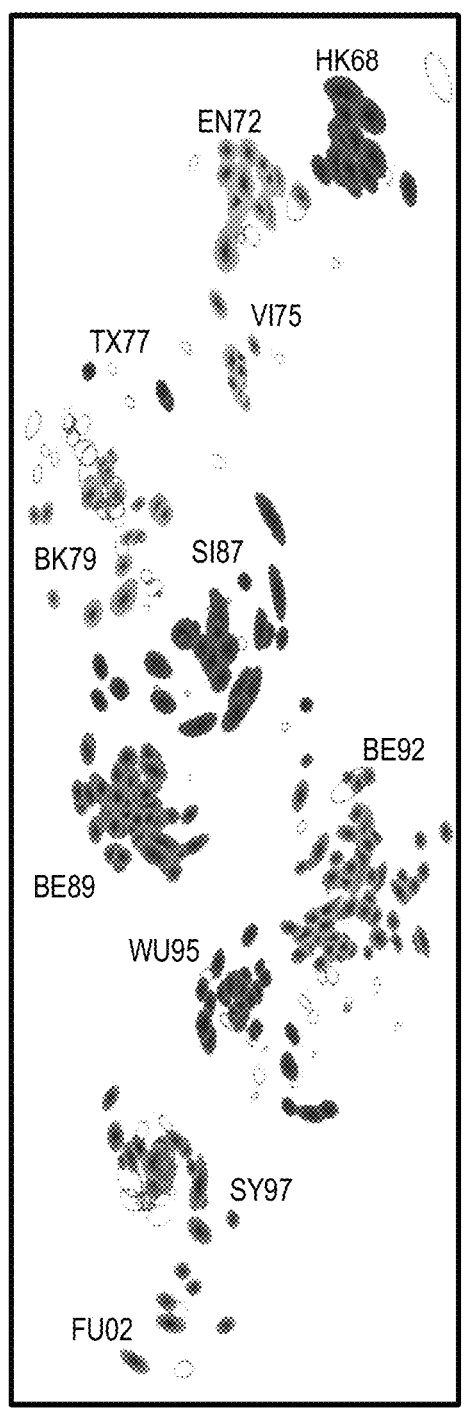
Figure 13B:
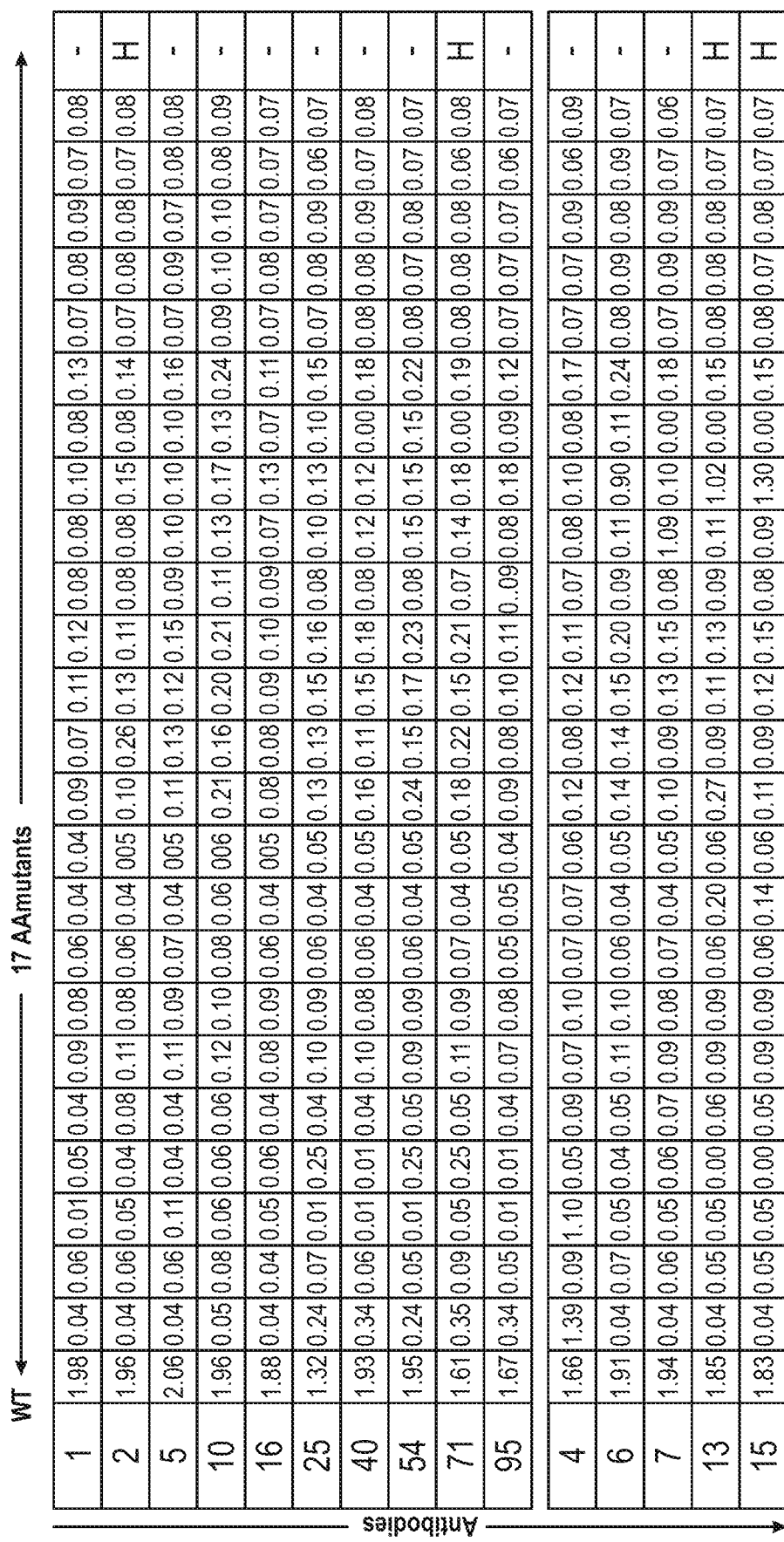
Figure 14B:
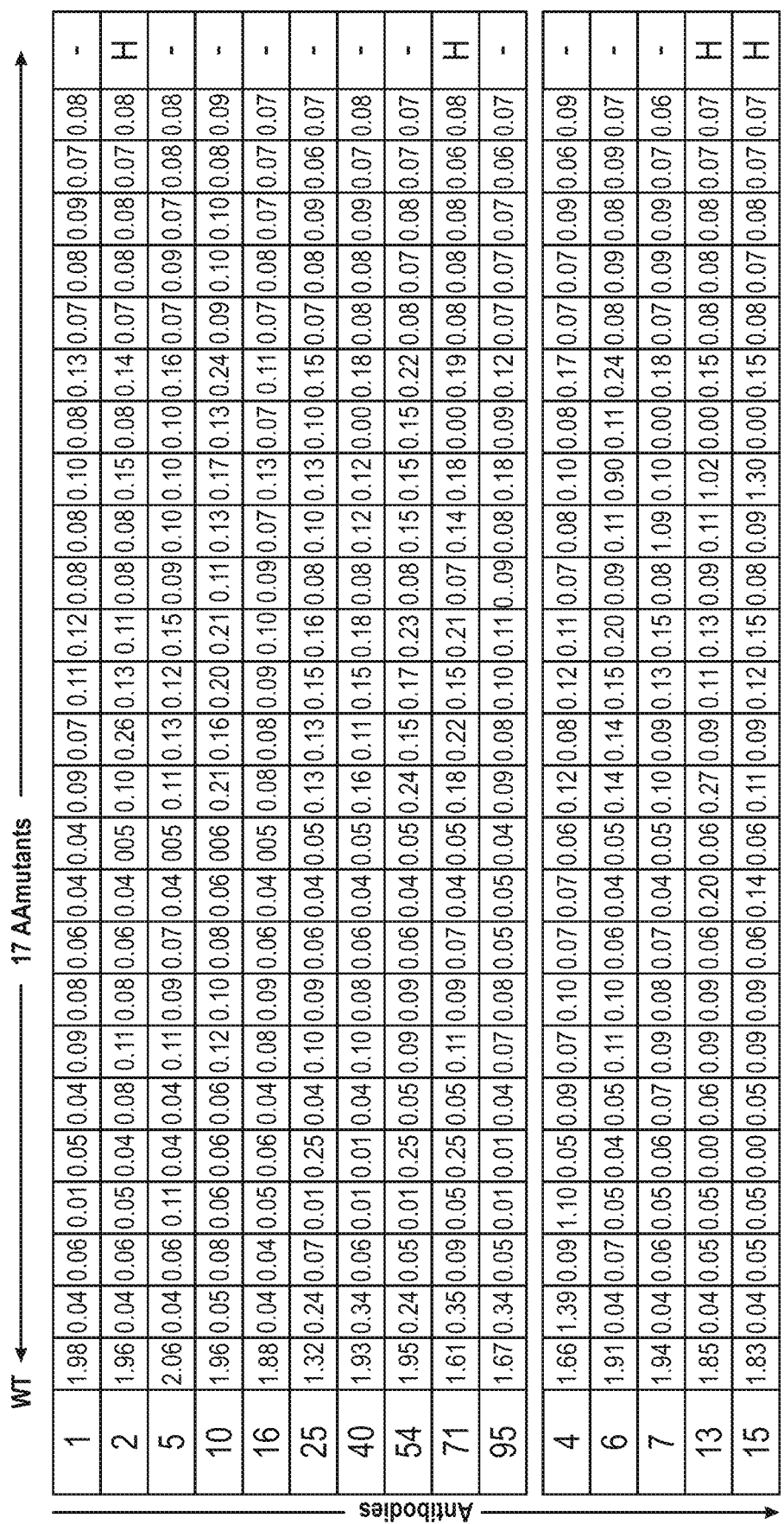
Figure 15A:
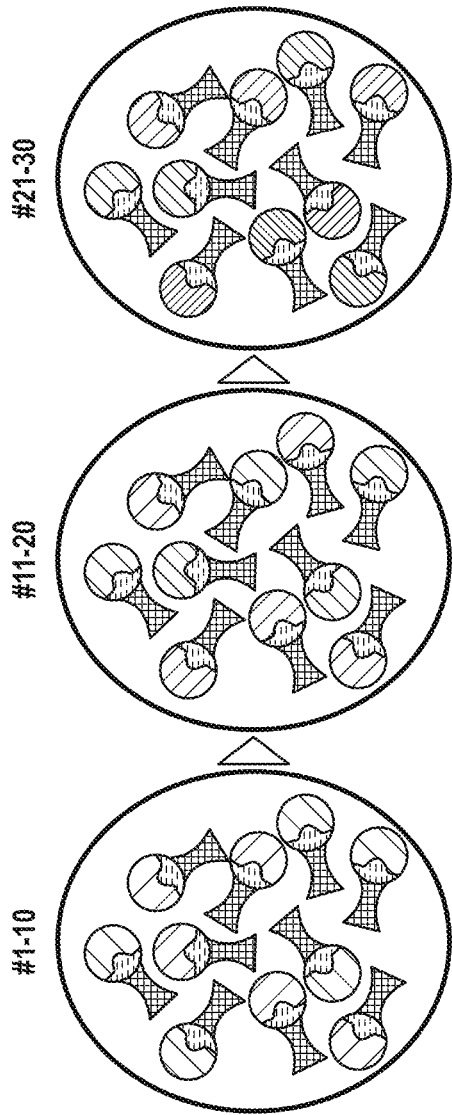
Figure 15B:
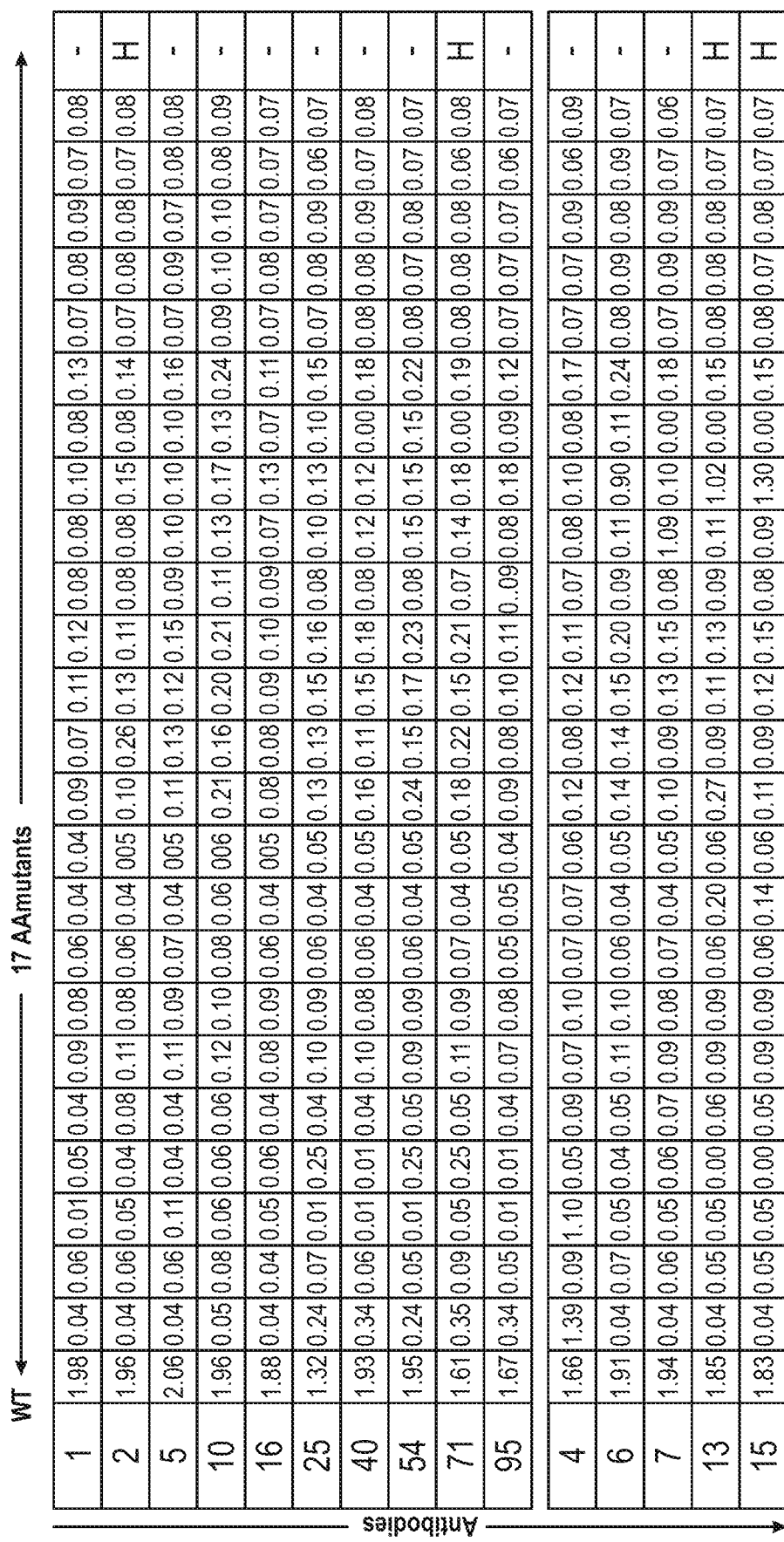

Random mutations at 15 amino acid positions. Based on published and unpublished data, random mutations are introduced at the following 15 amino acid positions of HA, which have been shown or are suspected to affect the antigenicity of H3 HA (all amino acid position numbers refer to the 'mature' H3 HA, after removal of the signal peptide): 121, 131, 135, 138, 140, 142, 144, 145, 155, 156, 158, 159, 189, 193, and 212 (FIG. 3). These sites are primarily located in the highly variable, immunodominant antigenic head epitopes A (positions 131, 135, 138, 140, 142, 144, 145), B (positions 155, 156, 158, 159, 189, 193), and C (positions 121, 193), and include the seven amino acid positions at which most seasonal H3N2 cluster changes have occurred (e.g., positions 145, 155, 156, 158, 159, 189, and 193 (84)). Random mutations at the selected positions are introduced into the HA protein of A/California/7/2004 (CA04) virus, the prototype of the California 2004 (CA04) antigenic cluster of humans H3N2 viruses. This older strain was selected so that the protective efficacy of the ID-EpiMut CA04-based vaccines could be tested against recent human H3N2 influenza viruses.

Briefly, a chemically synthesized cDNA library possessing random mutations at the selected positions of CA04 HA is prepared, the cDNA library is PCR amplified, and cloned into an RNA polymerase I vector, resulting in a plasmid library.

Generation of virus libraries. The plasmid library of mutant HAs is used to generate a virus library in the genetic background of a high-yield A/Puerto Rico/8/34 (PR8) virus, which confers high virus titers in cultured cells (Ping et al., 2015). Specifically, w $10^6$ 293T cells (in 6-well plates) are transfected with 1 µg of the mutant HA plasmid library, with 0.1 µg each of the RNA polymerase I plasmids for the transcription of the remaining viral RNAs (all derived from high-yield PR8 virus), and with 0.1 µg each of polymerase protein expression plasmids for the polymerase and NP proteins. Forty-eight hours later, aliquots of supernatants are collected from transfected cells and plaque assays performed in MDCK cells to assess the titers of the virus library. As stated earlier, typically about ~$10^4$-$10^7$ pfu of mutant viruses per ml of cell culture supernatant is obtained. Libraries are amplified in AX-4 cells (MDCK cells overexpressing α2,6-linked sialic acids on the cell surface, to which human influenza viruses bind efficiently).

Selection of ID-EpiMut HA Variants with Immunodominant Head Epitopes that are Antigenically Distinct from Those of (Most) Influenza Viruses To increase the levels of antibody responses to immune-subdominant epitopes in the stem and head of HA, HA variants with non-naturally occurring immunodominant antigenic head epitopes are generated. To select such mutants, the virus library is incubated with mixtures of ferret sera raised against viruses of different antigenic clades, and with mixtures of human sera from donors of different age groups who have been exposed to different viruses and vaccines during their lifetime.

Specifically, the virus library is incubated with different concentrations of serum mixtures, and then plaque assays in AX-4 cells are performed. Virus plaques are picked from the highest serum concentration at which plaques are detected. Individual viruses are amplified in AX-A cells and their HA genes sequenced. >100 individual HA genes are sequenced for each serum type (human or ferret) and serum concentration.

Viruses with amino acids that are not commonly found at the respective amino acid position (e.g., in <1% of sequences in the Influenza Research Database) are of particular interest. Highest priority is given to HAs with amino acids that have not been frequently detected at the respective position of any HA subtype (e.g., in <1% of sequences in the Influenza Research Database). For all mutants, the entire HA gene is sequenced to determine whether additional mutations emerged (outside of the targeted amino acid positions) that may have compensatory functions such as stabilizing effects on HA. The 100 ID-EpiMut HA variants with the least sequence homology to known influenza viruses at the targeted positions) are selected for further analysis (FIG. 5).

Reactivity of ID-EpiMut HA Variants with H3 HA- and Stem-Specific mAbs

After isolating ID-EpiMut HA variants with diverse sequences in the immunodominant antigenic head epitopes, reactivity of these HA proteins is tested with a panel of H3 HA-specific Abs. A panel may include >100 antibodies (Yamayoshi et al., 2017; Epstein et al., 2002). The ability of these mAbs to neutralize representative human H3N2 influenza viruses of all of the major antigenic clades was tested (Table 2) and it was found that most of them neutralized only subsets of the test viruses, indicating that they react with the highly variable, immunodominant antigenic head epitopes A-E Several of these mAbs, however, did neutralize viruses from most of the major antigenic clusters of human H3N2 viruses (Table 2). Based on competition studies with known stem-reacting mAbs, these mAbs were found to interact with the HA head.

plasmid and transfected into 293T cells. Wild-type CA04 HA protein serves as a control. At 24 h post-transfection, the cells are fixed with 4% paraformaldehyde. The HA-expressing cells are incubated with mAbs (1 μg/ml) followed by a peroxidase-conjugated goat anti-human IgG, Fcγ Fragment-specific antibody (Jackson Immuno-Research). TMB (3,3', 5,5'-Tetramethylbenzidine) solution is added for 5 min at

TABLE 2

$IC_{50}$ values (μg/ml) of selected mAbs measured by micro-neutralization assay[1]

| | Antigenic Cluster | | | | | | | |
|---|---|---|---|---|---|---|---|---|
| Name | HK68 | EN72 | VI75 | TX77 | BK79 | SI87 | BE89 | BE92 |
| #1 | 25.00** | 25.00** | 12.50*** | 25.00* | 12.50*** | 25.00* | 12.50*** | 12.50*** |
| #2 | >50 | >50 | >50 | 6.25*** | 0.78**** | 0.39**** | 1.56**** | 1.56**** |
| #3 | >50 | >50 | 0.20**** | 3.13*** | 0.20**** | 0.20**** | >50 | 1.56**** |
| #4 | >50 | >50 | 25.00* | 12.50*** | 1.56**** | 12.50*** | 0.78**** | 3.13**** |
| #5 | 25.00** | >50 | 0.78**** | 1.56**** | 0.78**** | 1.56**** | >50 | 3.13**** |

| | Antigenic Cluster | | | | | | |
|---|---|---|---|---|---|---|---|
| Name | WH95 | SY97 | FU02 | CA04 | WI05 | PE09 | TX12 | HK14 |
| #1 | 12.50&*** | 12.50*** | 25.00* | >50 | 6.25*** | 12.50** | >50 | >50 |
| #2 | 3.13**** | 3.13**** | 12.50** | 12.50** | 12.50** | 3.13**** | 6.25**** | 12.50*** |
| #3 | 0.78**** | 0.20**** | 1.56**** | 0.20**** | 0.20**** | 0.20**** | 1.56**** | 1.56**** |
| #4 | 3.13**** | 6.25*** | 0.78**** | 6.25*** | 0.39**** | 6.25*** | >50 | 12.50*** |
| #5 | 3.13**** | 12.50** | 3.13**** | 6.25*** | 12.50** | 6.25*** | 6.25*** | 25.00* |

[1]Shown are the IC50 values of the indicated mAbs with viruses representing different antigenic clusters of human H3N2 viruses (HK68, Hong Kong '68; EN72, England '72: VI75, Victoria '75; TX77, Texas '77; BK79, Bangkok '79, SI87, Sichuan '87; BE89, Beijing '89; BE92, Beijing '92; WH95, Wuhan '95; SY97, Sydney '97; FU02, Fujan '02; CA04, California '04; WI05, Wisconsin '05; PE09, Perth '09; TX12, Texas '12; HK14, Hong Kong '14. The *, , *, **** indicate the level of reactivity (that is, *, , *, **** indicate higher reactivity).

In addition, the reactivity of ID-EpiMut HAs to a panel of stem-reactive mAbs (see, Yamayoshi et al., 2017 and 2018) or synthesized based on the published sequence (Corti et al., 2011) (Table 3) were tested. These mAbs recognize HAs of group 2 (1417infC10), or of group 1 and 2 HAs.

TABLE 3

Reactivity of stem-reactive mAbs with HAs of the indicated subtypes

| | Group 1 | | Group 2 | | |
|---|---|---|---|---|---|
| mAbs | H1 | H5 | H3 | H7 | Reference |
| S9-1-10/5-1[1] | ✓ | ✓ | | ✓ | Yamayoshi et al., 2017 |
| 3352E69 | ✓ | | ✓ | ✓ | Yamayoshi et al., 2017 |
| 10-4-7/1 | ✓ | ✓ | ✓ | ✓ | Yamayoshi et al., 2017 |
| 4-8-6/4 | ✓ | ✓ | ✓ | ✓ | Yamayoshi et al., 2017 |
| 3381E12 | ✓ | ✓ | ✓ | ✓ | Yamayoshi et al., 2017 |
| 3381A11 | ✓ | ✓ | ✓ | ✓ | Yamayoshi et al., 2017 |
| 3352E71 | ✓ | ✓ | ✓ | ✓ | Yamayoshi et al., 2017 |
| 1417infE21[2] | ✓ | | ✓ | ✓ | Yamayoshi et al., 2018 |
| 1417infC10[3] | | | ✓ | ✓ | Yamayoshi et al., 2018 |
| FI6V3[1] | ✓ | ✓ | ✓ | ✓ | Corti et al., 2011 |

[1]Reacts with HAs of all 18 subtypes
[2]Reacts with H1, H5, H6, H8 (all group 1) & H3, H4, H7, H10, H14, H15 (all group 2) HAs
[3]Reacts with H3, H4, H7, H10, H14, H15 (all group 2) HAs Hemagglutination inhibition (HI) assays measure the ability of antibodies to inhibit HA binding to red blood cells. HI assays are frequently used to distinguish between antibodies that bind to the head (where the receptor-binding pocket is located that mediates binding to sialic acids on red blood cells) and antibodies that bind to the stem and do not interfere with hemagglutination. However, recent H3N2 viruses do not bind to commonly used red blood cells.

To test the reactivity of the selected 100 ID-EpiMut HA variants, their HA genes are cloned into a protein expression room temperature before the reaction is stopped by the addition of $H_2SO_4$. The optical density at 450 nm (OD450) is measured by using a VersaMax plate reader (Molecular Devices). The OD450 values of mock-transfected wells incubated with each mAb is subtracted as background.

The reactivity of the ID-EpiMut HA variants is compared with that of wild-type HA. Mutants that lose their reactivity with cluster-specific Abs (directed against highly variable, immunodominant antigenic head epitopes), but retain their reactivity with broadly-reactive H3-specific Abs and with stem-specific Abs (directed against conserved, immune-subdominant antigenic epitopes), are identified. Up to 50 ID-EpiMut HA proteins that fulfill these criteria (FIG. 5) are collected.

Example 3

Immunogenicity and protective efficacy of ID-EpiMut vaccines. Each of the variants produced by the method likely have a unique antigen to the immune system; by mixing them, the vaccine contains low amounts of each of the non-naturally occurring immunodominant antigenic head epitopes, but high amounts of the immune-subdominant epitopes (which are the same in all ID-EpiMut HAs). Such a vaccine elicits higher amounts of antibodies directed at the conserved immune-subdominant epitopes compared with a vaccine presenting only one wild-type HA (which is the current practice with influenza vaccines); the higher levels of antibodies to conserved immune-subdominant epitopes result in cross-protection.

Experimental Approach. Mouse antisera to individual and mixed ID-EpiMut HA variants is generated and tested for reactivity. Vaccination and challenge studies are conducted in mice and ferrets to assess whether mixtures of non-naturally occurring immunodominant epitopes dilute the responses to these epitopes and increase the levels of antibodies to immune-subdominant epitopes, resulting in more broadly protective immunity.

Generation of virus-like particles possessing individual ID-EpiMut HA variants. In addition to HA (the major influenza viral antigen), other influenza viral proteins including NA, NP, and the matrix (M1) and ion channel (M2) proteins contribute to viral antigenicity; in fact, immunity to NP and M1 are protective in the mouse model. To avoid any confounding effects from these proteins, ID-EpiMut HA variants are presented on VLPs of Ebola virus. Co-expression of Ebola virus VP40 and influenza virus HA results in the highly efficient generation of VLPs decorated with HA. Moreover, a 293T cell line that stably expresses VP40 may be employed for highly efficient VLP formation. VP40-expressing 293T cells are transfected with protein expression plasmids encoding each of the 50 ID-EpiMut HA variants. Two-to-three days later, cells are treated with bacterial neuraminidase to efficiently release the VLPs from the cells. The cell culture supernatant with the released VLPs is harvested, purified through a sucrose gradient, concentrated by ultracentrifugation, and the total protein yield measured by using the BCA assay (Thermo Scientific). The resulting 50 ID-EpiMut-HA/VP40 VLPs (each decorated with a single HA mutant) (FIG. 5) is used to immunize mice.

Generation of virus-like particles possessing multiple ID-EpiMut HA variants. In addition to VLPs decorated with a single ID-EpiMut HA variant, eight different ID-EpiMut-HA/VP40 VLPs that are decorated with different ID-EpiMut HAs (FIG. 5) are generated. Specifically, five ID-EpiMut-HA/VP40 VLPs are tested that are decorated with 10 ID-EpiMut HA variants each, two ID-EpiMut-HA/VP40 VLPs are tested that are decorated with all 25 ID-EpiMut HA variants each, and one TD-EpiMut-HA/VP40 VLP is tested that is decorated with all 50 ID-EpiMut HA variants (for the first two sets, ID-EpiMut HA mutants are randomly sorted into groups of 10 or 25, respectively). VP40-expressing 293T cells are cotransfected with the respective number of different protein expression plasmids expressing different ID-EpiMut HAs. The presentation of different HA mutants on the same VLP will likely reduce the B cell populations that are specific to one particular mutant.

Generation and characterization of mouse sera directed against ID-EpiMut-HA/VP40 VLPs. Mice (BALB/c female mice, Jackson Laboratories: three per group) are intramuscularly immunized with 10-20 μg of total protein of ID-EpiMut-HA/VP40 VLPs and two weeks later are intramuscularly boosted with the same amount of protein of ID-EpiMut-HA/VP40 VLPs. Three weeks after the second immunization, blood is collected.

The mouse sera is tested for reactivity against the following groups of HA proteins: (1) Human H3N2 virus HA proteins representing all of the major antigenic clades, derived from viruses that have not been amplified in embryonated chicken eggs (thus eliminating the risk of egg-adapting HA mutations that affect antigenicity); (2) ID-EpiMut HA variants; and (3) HA proteins representing several other HA subtypes, including H1, H5, and H7 (for each of these subtypes, a panel of HA proteins representing the major antigenic clades and sub-clades are used).

An ELISA is employed with purified HA protein using protocol to express secreted forms of HA that are stabilized by a trimerization motif ('foldon') (Stevens et al., 2004). The interaction of mouse sera with purified HA proteins is detected as described above. To assess the relative contributions of antibodies binding to highly variable, immunodominant antigenic head epitopes, conserved immune-subdominant antigenic stem epitopes, and conserved immune-subdominant antigenic head epitopes, competition assays are performed with human Abs known to bind to these epitopes. Controls include wild-type HA protein and antiserum raised against it, as well as antigenically distant influenza B virus HA protein and antiserum raised against it.

From the 50 ID-EpiMut-HA/VP40 VLPs decorated with one EpiMut HA, the top 30 candidates with the highest proportions of antibodies reactive against the conserved, immune-subdominant antigenic epitopes in the stem and head regions of HA are selected (FIG. 5).

For the eight ID-EpiMut-HA/VP40 VLPs decorated with multiple EpiMut HAs, candidates are eliminated if they do not elicit increased amounts of antibodies to immune-subdominant epitopes (compared to wild-type HA) (FIG. 5).

Immunization of Mice with Mixtures of ID-EpiMut-HA/VP40 VLPs

Immunization with mixtures of ID-EpiMut HAs with multiple mutations in the immunodominant antigenic head epitopes likely results in relatively low antibody responses to each of the unique, immunodominant antigens, while boosting responses to the shared epitopes (e.g., the conserved immune-subdominant epitopes in the HA stem and head). To assess this, w different vaccination strategies are tested in which mice (e.g., groups of five animals) are primed with mixtures of 10, 15, or 30 ID-EpiMut-HA/VP40 VLPs, each decorated with a single ID-EpiMut HA (Table 4a). Mice are unboosted, boosted with the same ID-EpiMut-HA/VP40 VLPs used for the prime immunization, or boosted with a different set of 10 or 15 ID-EpiMut-HA/VP40 VLPs.

Likewise, mice are primed with a single ID-EpiMut-HA/VP40 VLP decorated with multiple different mutants (Table 4b), and then mock-boost, boost with the same ID-EpiMut-HA/VP40 VLP, or boost with a different ID-EpiMut-HA/VP40 VLP (this does not apply for animals vaccinated with the ID-EpiMut-HA/VP40 VLP decorated with all 50 EpiMut HA mutants). In addition, controls are primed or primed and boosted with HA/VP40 VLPs decorated with the wild-type HA protein.

Sera is collected 28 days after the last immunization and tested for antibody levels to immune-subdominant antigenic epitopes as described above. Comparison of the different vaccination strategies reveals if two immunizations with the same mixture of ID-EpiMut-HA/VP40 VLPs increase the amount of antibodies to immune-subdominant epitopes compared with a single immunization. Comparison of the different vaccination strategies also reveals if a prime/boost regimen with different ID-EpiMut-HA/VP40 VLPs increases the amount of antibodies to immune-subdominant epitopes compared with a prime/boost regimen with the same ID-EpiMut-HA/VP40 VLPs. Moreover, comparisons of the different vaccination strategies reveal if one VLP decorated with multiple HA mutants (see Table 4b) elicits higher amounts of antibodies to immune-subdominant epitopes than multiple VLPs decorated with one HA mutant each (see Table 4a). The comparison of VLPs decorated with 10, 25, or 50 HA mutants also provides information on the number of different HAs needed to dilute immune response to the immune-dominant epitopes in the HA head.

If mixtures of ten ID-EpiMut HAs (provided from one or ten VLPs) dilute the immune response to the immunodominant epitopes, similar experiments are performed with mixtures of five or three ID-EpiMut HAs to determine the lowest number of different ID-EpiMut HAs needed for the dilution effect.

From the different vaccination regimen tested here, the top 10 are selected (e.g., those with the highest levels of antibodies to immune-subdominant epitopes) for protection studies in mice (FIG. 5).

TABLE 4a

Overview of vaccination strategies

| Vaccination Strategy | ID-EpiMut HA/VP40 VLPs (Prime) # | ID-EpiMut HA/VP40 VLPs (Boost) # |
|---|---|---|
| VLPs decorated with individual EpiMut HAs | 1-10 | None |
|  |  | 1-10 |
|  |  | 11-20 |
|  |  | 21-30 |
|  | 11-20 | None |
|  |  | 1-10 |
|  |  | 11-20 |
|  |  | 21-30 |

TABLE 4a-continued

Overview of vaccination strategies

| Vaccination Strategy | ID-EpiMut HA/VP40 VLPs (Prime) # | ID-EpiMut HA/VP40 VLPs (Boost) # |
|---|---|---|
|  | 21-30 | None |
|  |  | 1-10 |
|  |  | 11-20 |
|  |  | 21-30 |
|  | 1-15 | None |
|  |  | 1-15 |
|  |  | 16-30 |
|  | 16-30 | None |
|  |  | 1-15 |
|  |  | 16-30 |
|  | 1-30 | None |
|  |  | 1-30 |

TABLE 4b

Overview of vaccination strategies (cont.)

| Vaccination Strategy | ID-EpiMut HA/VP40 VLPs (Prime) # | ID-EpiMut HA/VP40 VLPs (Boost) # |
|---|---|---|
| VLPs decorated with multiple EpiMut HAs | 1 VLP with ID-EpiMut HAs 1-10 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 11-20 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 21-30 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 31-40 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 41-50 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 1-25 | None |
|  |  | 1 VLP with ID-EpiMut HAs 1-25 |
|  |  | 1 VLP with ID-EpiMut HAs 26-50 |
|  | 1 VLP with ID-EpiMut HAs 26-50 | None |
|  |  | 1 VLP with ID-EpiMut HAs 1-25 |
|  |  | 1 VLP with ID-EpiMut HAs 26-50 |
|  | 1 VLP with ID-EpiMut HAs 1-50 | None |
|  |  | 1 VLP with ID-EpiMut HAs 1-50 |

Challenge Studies in Mice Vaccinated with ID-EpiMut-HA/VP40 VLPs

After establishing that mixtures of highly mutated immunodominant antigenic head epitopes dilute the immune responses to these epitopes and boost the antibody levels to conserved, immune-subdominant epitopes, it is determined whether the increased levels of antibodies to the immune-subdominant epitopes provide broader protection against seasonal human H3N2 viruses than the protection elicited by a wild-type virus-based vaccine.

For the top 10 vaccination regimen that elicit increased levels of antibodies to conserved, immune-subdominant epitopes, the protective efficacy of the antibodies raised to ID-EpiMut-HAs is evaluated. First, 48 mice each are vaccinated with the selected vaccination regimen. Recent human H3N2 influenza viruses do not replicate efficiently in mice. Mouse-adapted variants of CA04 (for homologous challenge) and of viruses representing the Perth 2009 (PE09), Victoria 2011 (VI11), and Hong Kong 2014 (HK14) antigenic clusters are generated for heterologous challenges, using established strategies for the generation of mouse-adapted viruses. To rule out effects of mouse-adapting mutations on antigenicity, the reactivity of wild-type and mouse-adapted viruses is compared with sera directed against wild-type HAs. If the mouse-adapted variants are antigenically similar to wild-type viruses, the four mouse-adapted viruses are used at a dose of $10^6$ pfu to challenge 12 vaccinated mice each. Four mice per challenge group are observed for weight loss; the remaining eight animals are euthanized on days 3 and 6 post-challenge (four animals per timepoint) to assess virus titers in the lungs and nasal turbiantes. Vaccination with ID-EpiMut-HAs elicits Abs that are more broadly protective than Abs elicited after vaccination with wild-type HA.

Immunogenicity of ID-EpiMut HA Influenza Vaccines in Ferrets

The top 3 vaccination regimen are tested for their immunogenicity in ferrets (FIG. 5). In ferrets, like humans, the contribution of the 'internal' influenza viral proteins is less pronounced than in mice. Therefore, the vaccination and challenge experiments in ferrets are carried out with influenza virus-based vaccine (e.g., viruses that possess the respective ID-EpiMut HAs are generated in the genetic background of PR8 virus). The recombinant viruses possessing ID-EpiMut HAs are inactivated with beta-propiolactone (an established procedure for the inactivation of influenza viruses) and the equivalent of 15 µg of HA protein is used for vaccination.

Protective Efficacy of ID-EpiMut HA Influenza Vaccines in Ferrets

Next, it is tested whether vaccination of ferrets with ID-EpiMut-HA influenza vaccine confers broader protection than that elicited by a vaccine based on wild-type HA. Ferrets (groups of 5) are immunized with the top 3 vaccination regimens (determined as stated above) (FIG. 5). Twenty-eight days after the last immunization, ferrets are intranasally infected with $10^6$ pfu of the homologous CA04 virus, or viruses representing the more recent Perth 2009 (PE09), Victoria 2011 (VI11), and Hong Kong 2014 (HK14) antigenic clusters (heterologous challenges). Starting one day after challenge, the infected animals are weighed every day and nasal wash samples collected every other day to determine virus titers. Vaccination with inactivated influenza vaccine possessing wild-type HA is expected to protect against challenge with the homologous CA04 virus, but provide incomplete protection against the heterologous viruses (which belong to different antigenic clusters). The finding that vaccination with ID-EpiMut HA influenza vaccine protects against infection with antigenic drift variants establishes the feasibility of the concept for universal influenza vaccines.

TABLE 5

Vaccination/challenge groups to test the broadly protective efficacy of EpiMut HA influenza vaccines

| Group | Influenza virus infections | Vaccination with ID-EpiMut HA influenza vaccine | Challenge |
|---|---|---|---|
| 1 | Sequential | ID-EpiMut HA | CA 04 (homol.) |
| 2 | infection with | vaccine 1* | PE09 (heterol.) |
| 3 | WU95, SY97, | | VI11 (heterol.) |
| 4 | and FU02 | | HK14 (heterol.) |
| 5 | viruses | ID-EpiMut HA | CA 04 (homol.) |
| 6 | | vaccine 2* | PE09 (heterol.) |
| 7 | | | VI11 (heterol.) |
| 8 | | | HK14 (heterol) |
| 9 | | ID-EpiMut HA | CA 04 (homol.) |
| 10 | | vaccine 3* | PE09 (heterol.) |
| 11 | | | VI11 (heterol.) |
| 12 | | | HK14 (heterol.) |
| 13 | | Wt-HA vaccine | CA 04 (homol.) |
| 14 | | (single | PE09 (heterol.) |
| 15 | | vaccination) | VI11 (heterol.) |
| 16 | | | HK14 (heterol.) |
| 17 | | Wt-HA vaccine | CA 04 (homol.) |
| 18 | | (two | PE09 (heterol.) |
| 19 | | vaccinations) | VI11 (heterol.) |
| 20 | | | HK14 (heterol.) |

*Vaccines 1, 2, and 3 indicate the top 3 vaccination regimen based on the data obtained in C.2.3.

Five ferrets (4-6-month-old females) per group are immunized intramuscularly. Twenty-eight days after the last immunization, sera is collected and the reactivity of the sera tested as described above. Control animals are immunized with inactivated influenza vaccine possessing wild-type HA protein. Immunization with ID-EpiMut HA influenza vaccine elicits higher amounts of antibodies directed against conserved, immune-subdominant epitopes than vaccination with a vaccine possessing wild-type HA.

Protective Efficacy of ID-EpiMut HA Influenza Vaccines in Ferrets

Next, it is tested whether vaccination of ferrets with ID-EpiMut-HA influenza vaccine confers broader protection than that elicited by a vaccine based on wild-type HA. Ferrets (groups of 5) are immunized with the top 3 vaccination regimen (determined as stated above) (FIG. 5). Twenty-eight days after the last immunization, ferrets are intranasally infected with $10^6$ pfu of the homologous CA04 virus, or viruses representing the more recent Perth 2009 (PE09), Victoria 2011 (VI11), and Hong Kong 2014 (HK14) antigenic clusters (heterologous challenges). Starting one day after challenge, the infected animals are weighed every day and nasal wash samples collected every other day to determine virus titers. Vaccination with inactivated influenza vaccine possessing wild-type HA protects against challenge with the homologous CA04 virus, but provides incomplete protection against the heterologous viruses (which belong to different antigenic clusters). The finding that vaccination with ID-EpiMut HA influenza vaccine protects against infection with antigenic drift variants establishes that vaccine as a universal influenza vaccine.

Protective Efficacy of ID-EpiMut HA Influenza Vaccine in Ferrets Pre-Exposed to Human Influenza Viruses Humans are repeatedly exposed to influenza viruses through natural infection and/or vaccination. To mimic this exposure to multiple influenza viruses, ferrets are sequentially infected with seasonal human H3N2 viruses representing three past antigenic clusters: the Wuhan 1995 (WU95), Sydney 1997 (SY97), and Fujian 2002 (FU02) clusters (Table 5). Next, animals are vaccinated with each of the top three vaccination approaches. Twenty-eight days after the last immunization, serum samples are collected from vaccinated animals and the reactivity of the sera tested. Sera from ferrets vaccinated with ID-EpiMut HA influenza vaccine are more cross-reactive than those obtained from ferrets immunized with influenza vaccine possessing wild-type HA.

Next, the pre-exposed and vaccinated animals are intranasally infected with $10^6$ pfu of the homologous CA04 virus, or with the heterologous PE09, VI11, or HK14 viruses (5 animals per group, Table 5). As described previously, body weight measurements are carried out every day and nasal washes are collected every other day, starting on day 1 after challenge. ID-EpiMut HA influenza vaccine provides broader protection against viruses of different antigenic clusters than influenza vaccine based on wild-type HA.

In summary, the reactivity and neutralizing properties of mouse sera raised against ID-EpiMut HA variants show that these sera are more broadly reactive and neutralizing than sera raised to wild-type HA. Vaccination/challenge studies establish that the disclosed vaccine approach provides more broadly protective immunity than that afforded by current vaccines based on wild-type HAs.

Thus, mixtures of non-naturally occurring immunodominant head epitopes dilute the immune responses to these epitopes and refocus immune responses towards conserved, immune-subdominant epitopes in HA, thereby increasing the amounts of cross-protective antibodies, thereby providing universal influenza vaccines.

TABLE 6

TK/2 (H3) Mutants

| Name Tokyo 2 | 121 N | 131 T | 135 T | 138 A | 140 I | 142 R | 144 S | 145 S | 155 T | 156 H | 157 L | 158 N | 171 N | 189 K | 193 F | 212 A | 225 D | Genotype |
|---|---|---|---|---|---|---|---|---|---|---|---|---|---|---|---|---|---|---|
| TK/2-177 Hck-41_14 | . | . | M | S | F | H | . | P | . | M | S | G | D | R | S | R | . | 1 |
| TK/2-177 Hck-41_69 | . | . | M | S | F | H | . | P | . | M | S | G | D | R | S | R | . | |
| TK/2-177 Hck-41_9 | . | . | M | S | F | H | . | P | . | M | S | G | D | R | S | R | . | |
| TK/2-177 Hck-37_87 | A | R | G | S | R | L | D | P | . | N | D | A | Y | N | R | N | E | 2 |
| TK/2-177 Hck-37_73 | E | K | . | T | P | D | R | M | Y | K | S | A | T | L | E | S | G | 3 |
| TK/2-177 Hck-37_84 | E | K | . | T | P | D | R | M | Y | K | S | A | T | L | E | S | G | |
| TK/2-177 Hck-37_68 | E | L | N | S | K | K | A | P | F | S | T | S | Q | A | R | L | T | 4 |
| TK/2-177 Hck-37_101 | E | S | S | . | T | F | G | A | F | A | R | G | R | M | H | Q | . | 5 |
| TK/2-177 Hck-41_3 | F | M | G | S | . | E | M | P | F | S | Q | M | R | T | D | L | G | 6 |
| TK/2-177 Hck-41_34 | F | M | G | S | . | E | M | P | F | S | Q | M | R | T | D | L | G | |
| TK/2-177 Hck-37_70-3 | F | M | G | S | . | E | M | P | F | S | Q | M | R | T | D | L | G | |
| TK/2-177 Hck-37_11 | F | R | N | . | T | N | I | N | Y | I | R | E | K | D | G | S | E | 7 |
| TK/2-177 Hck-37_19 | F | R | S | S | P | M | G | N | . | L | P | D | K | D | A | . | A | 8 |
| TK/2-177 Hck-37_10 | F | S | G | S | L | H | R | A | W | S | R | T | F | F | S | S | L | 9 |
| TK/2-177 Hck-37_1 | F | S | H | S | S | T | N | P | F | A | S | R | M | A | Q | S | C | 10 |
| TK/2-177 Hck-37_98 | F | V | G | S | K | T | G | Q | I | R | S | T | L | N | S | I | R | 11 |
| TK/2-177 Hck-37_71 | F | Y | H | S | W | N | K | L | . | A | . | P | S | E | R | T | R | 12 |
| TK/2-177 Hck-37_90 | H | A | V | . | R | I | Q | P | Y | Q | S | R | V | S | R | S | . | 13 |
| TK/2-177 Hck-41_H50 | H | E | V | . | V | N | V | P | H | R | H | E | M | N | W | T | S | 14 |
| TK/2-177 Hck-37_70-2 | H | K | S | S | K | . | G | P | S | Q | G | R | M | A | . | L | G | 15 |
| TK/2-177 Hck-41_H96 | H | K | V | S | P | L | R | T | S | A | W | D | R | S | A | H | A | 16 |
| TK/2-177 Hck-37_12 | H | R | V | . | R | S | M | T | V | S | S | S | R | N | N | S | G | 17 |
| TK/2-177 Hck-37_16 | I | E | H | S | D | . | K | P | V | T | R | K | S | R | S | W | G | 18 |
| TK/2-177 Hck-37_74 | I | E | K | S | Y | T | G | N | V | R | R | G | F | R | D | F | S | 19 2and3 |

TABLE 6-continued

TK/2 (H3) Mutants

| Name<br>Tokyo 2 | 121<br>N | 131<br>T | 135<br>T | 138<br>A | 140<br>I | 142<br>R | 144<br>S | 145<br>S | 155<br>S | 156<br>T | 157<br>H | 158<br>L | 171<br>N | 189<br>N | 193<br>K | 212<br>F | 225<br>A | D | Genotype |
|---|---|---|---|---|---|---|---|---|---|---|---|---|---|---|---|---|---|---|---|
| TK/2-177 Hck-41_58 | I | L | S | S | D | Y | K | K | R | A | R | . | P | N | A | T | R | | 20 |
| TK/2-177 Hck-37_81 | I | R | M | S | L | A | N | . | . | N | R | V | V | S | R | G | . | | 21 |
| TK/2-177 Hck-37_102 | I | R | Q | S | N | A | M | P | . | K | H | L | L | H | S | T | K | | 22 |
| TK/2-177 Hck-37_49 | K | N | . | . | H | N | M | P | F | R | S | . | T | T | L | S | H | | 23 |
| TK/2-177 Hck-37_22-1 | L | . | G | . | M | D | K | . | I | R | R | Q | M | E | G | T | R | | 24 |
| TK/2-177 Hck-37_31 | L | . | G | . | M | D | K | . | I | R | R | Q | M | E | G | T | R | | |
| TK/2-177 Hck-37_56 | L | . | G | . | M | D | K | . | I | R | R | Q | M | E | G | T | R | | |
| TK/2-177 Hck-41_75 | L | . | G | . | M | D | K | . | I | R | R | Q | M | E | G | T | R | | |
| TK/2-177 Hck-37_95 | L | . | G | . | M | D | K | . | I | R | R | Q | M | E | G | T | R | | |
| TK/2-177 Hck-41_H48 | L | A | . | S | P | D | F | P | H | S | R | L | A | S | T | Q | Q | | 25 |
| TK/2-177 Hck-41_H51 | L | A | . | S | P | D | F | P | H | S | R | L | A | S | T | Q | Q | | |
| TK/2-177 Hck-41_H58 | L | A | . | S | P | D | F | P | H | S | R | L | A | S | T | Q | Q | | |
| TK/2-177 Hck-37_64 | L | A | A | S | L | K | N | Y | . | S | M | D | C | F | A | T | S | | 26 |
| TK/2-177 Hck-37_74-1 | L | A | A | S | L | K | N | Y | . | S | M | D | C | F | A | T | S | | |
| TK/2-177 Hck-41_79 | L | A | F | . | S | H | R | . | Y | A | V | G | T | M | M | T | S | | 27 |
| TK/2-177 Hck-37_59 | L | I | . | S | L | I | G | N | . | . | S | G | V | H | Q | T | L | | 28 |
| TK/2-177 Hck-41_89 | L | L | D | S | S | . | G | P | H | A | Q | A | A | R | S | N | H | | 29 |
| TK/2-177 Hck-37_33 | L | L | R | S | L | . | R | E | H | S | P | M | . | M | A | N | H | | 30 |
| TK/2-177 Hck-37_35 | L | S | Q | . | N | F | A | P | F | S | E | S | . | N | G | . | S | | 31 |
| TK/2-177 Hck-37_39 | M | . | N | S | P | T | N | Q | F | S | R | R | H | V | N | S | T | | 32 |
| TK/2-177 Hck-37_45 | M | . | V | S | M | G | V | P | H | V | M | S | L | Y | K | S | S | | 33 |
| TK/2-177 Hck-41_76 | M | N | . | S | G | E | E | E | Y | A | R | E | R | M | T | H | G | | 34 |
| TK/2-177 Hck-41_21 | M | Q | A | S | T | N | . | R | F | V | S | R | . | D | S | L | T | | 35 |
| TK/2-177 Hck-37_17-1 | R | G | S | S | L | S | I | P | K | A | A | A | S | I | H | F | R | | 36 |
| TK/2-177 Hck-41_93 | R | L | V | S | A | G | R | A | S | S | Q | S | Y | D | . | S | R | | 37 |
| TK/2-177 Hck-41_53 | R | L | V | S | A | K | M | P | . | A | S | L | E | T | L | S | M | | 38 |
| TK/2-177 Hck-37_36 | R | N | H | S | R | G | M | M | . | A | S | L | F | S | T | V | C | | 39 |
| TK/2-177 Hck-37_60 | R | N | H | S | R | G | M | M | . | A | S | L | F | S | T | V | C | | |
| TK/2-177 Hck-37_H5 | R | N | S | . | M | Q | Q | V | . | K | F | R | M | E | S | W | ? | | 40 |
| TK/2-177 Hck-37_96 | S | A | V | S | N | K | H | A | F | S | D | S | Q | E | A | Q | . | | 41 |
| TK/2-177 Hck-41_48 | S | G | R | S | R | N | . | N | W | S | G | K | L | T | S | I | G | | 42 |
| TK/2-177 Hck-37_67 | S | H | V | S | . | Q | Q | W | . | L | H | D | T | G | A | S | . | | 43 |
| TK/2-177 Hck-41_7 | S | K | S | S | Y | L | E | . | H | A | D | Q | G | . | A | R | S | | 44 |
| TK/2-177 Hck-37_37 | T | E | G | C | M | H | T | M | F | K | P | R | E | R | S | V | G | | 45 |
| TK/2-177 Hck-37_28 | T | G | V | S | . | T | R | . | V | A | N | V | K | S | D | H | T | | 46 |

TABLE 6-continued

TK/2 (H3) Mutants

| Name | \_\_\_ | \_\_\_ | \_\_\_ | \_\_\_ | \_\_\_ | \_\_\_ | Amino acid position | \_\_\_ | \_\_\_ | \_\_\_ | \_\_\_ | \_\_\_ | \_\_\_ | \_\_\_ | \_\_\_ | \_\_\_ | \_\_\_ | \_\_\_ |
|---|---|---|---|---|---|---|---|---|---|---|---|---|---|---|---|---|---|---|
| | 121 | 131 | 135 | 138 | 140 | 142 | 144 | 145 | 155 | 156 | 157 | 158 | 171 | 189 | 193 | 212 | 225 | |
| Tokyo 2 | N | T | T | A | I | R | S | S | S | T | H | L | N | N | K | F | A | D | Genotype |
| TK/2-177 Hck-41_54 | T | K | Q | S | N | G | K | Q | S | S | D | E | L | T | W | I | S | 47 |
| TK/2-177 Hck-37_40 | T | N | W | S | S | N | A | G | . | S | A | L | L | N | H | S | S | 48 |
| TK/2-177 Hck-37_86 | T | R | G | T | V | . | E | R | V | Q | R | G | S | A | G | M | S | 49 |
| TK/2-177 Hck-37_85 | T | V | A | S | K | I | G | V | . | R | S | L | L | V | K | V | G | 50 |
| TK/2-177 Hck-37_97 | T | V | A | S | K | I | G | V | . | R | S | L | L | V | K | V | G | |
| TK/2-177 Hck-37_94 | V | ? | V | S | S | S | G | M | . | A | S | E | I | T | S | L | L | 51 |
| TK/2-177 Hck-37_17-2and3 | V | A | . | . | L | C | E | A | V | S | T | R | S | G | S | S | G | 52 |
| TK/2-177 Hck-41_4 | V | K | . | S | P | G | . | D | F | T | P | I | Y | N | Y | V | E | 53 |
| TK/2-177 Hck-37_5 | V | K | . | S | P | G | . | D | F | T | P | I | Y | N | Y | V | E | |
| TK/2-177 Hck-37_42 | V | K | V | . | P | G | D | Y | . | S | W | K | R | Q | . | G | Q | 54 |
| TK/2-177 Hck-41_55 | V | K | V | S | Q | . | R | H | . | S | T | S | R | L | N | . | L | 55 |
| TK/2-177 Hck-37_57 | V | L | V | S | L | S | . | H | V | V | S | K | E | S | H | T | R | 56 |
| TK/2-177 Hck-41_78 | V | L | V | S | L | S | . | H | V | V | S | K | E | S | H | T | R | |
| TK/2-177 Hck-37_2 | V | N | C | S | A | A | M | N | . | Q | S | Q | T | R | N | V | R | 57 |
| TK/2-177 Hck-37_65 | V | N | C | S | A | A | M | N | . | Q | S | Q | T | R | N | V | R | |
| TK/2-177 Hck-41_51 | V | Q | . | S | K | T | K | R | W | K | G | H | R | E | Q | S | T | 58 |
| TK/2-177 Hck-37_100 | V | R | . | . | S | G | I | R | . | W | V | G | M | V | A | W | A | 59 |
| TK/2-177 Hck-37_20 | V | R | G | S | C | V | K | F | . | A | K | S | L | E | I | L | E | 60 |
| TK/2-177 Hck-41_41 | V | R | K | S | P | E | . | K | V | M | E | Q | H | R | S | Q | H | 61 |
| TK/2-177 Hck-41_26 | W | K | . | S | H | Y | T | P | S | A | Q | E | A | R | A | ? | Q | 62 |
| TK/2-177 Hck-41_38 | W | K | . | S | H | Y | T | P | S | A | Q | E | A | R | A | T | Q | |
| TK/2-177 Hck-41_66 | W | K | . | S | H | Y | T | P | S | A | Q | E | A | R | A | T | Q | |
| TK/2-177 Hck-37_22-3 | Y | K | S | S | K | M | N | P | . | M | ? | L | W | T | L | L | R | 63 |
| TK/2-177 Hck-37_32 | Y | L | R | S | L | H | E | R | S | R | . | R | M | A | E | H | . | 64 |
| TK/2-177 Hck-41_50 | Y | L | R | S | L | H | E | R | S | R | . | R | M | A | E | H | . | |
| TK/2-177 Hck-41_8 | Y | L | R | S | L | H | E | R | S | R | . | R | M | A | E | H | . | |
| TK/2-177 Hck-41_52 | Y | L | R | S | M | A | H | Q | Y | A | W | R | E | Q | R | V | W | 65 |
| TK/2-177 Hck-37_62 | Y | M | S | . | . | E | R | M | V | K | . | G | S | S | D | F | A | 66 |

REFERENCES

Andrews et al., *Sci. Transl. Med.*, 7:316ra192 (2015).
Belser et al., *J. Virol.*, 90:4647 (2016).
Bommakanti et al., *J. Virol.*, 86:13434 (2012).
Bommakanti et al., *Proc. Natl. Acad. Sci. USA*, 107:13701 (2010).
Chen et al., *J. Virol.*, 90:3789 (2016).
Clementi et al., *PLoS One*, 6:e28001 (2011).
Corti et al., *Science*, 333:850 (2011).
DiLillo et al., *J. Clin. Invest.*, 126:605 (2016).
Dreyfus et al., *Science*, 2:1343 (2012).
Ekiert et al., *Curr. Opin. Virol.*, 2:134 (2012).
Ekiert et al., *Nature*, 489:526 (2011).
Ekiert et al., *Science*, 3.24:246 (2009).
Ekiert et al., *Science*, 333:843 (2011).
Ellebedy et al., *Proc. Natl. Acad. Sci. USA*, 111:13133 (2014).
Epstein et al., *Emerg. Infect. Dis.*, 8:796 (2002).
Erbelding et al., *J. Infect, Dis*., _____:_____doi:10.1093/infdis/jiy103 (2018).
Fleury et al., *Nat. Struct. Biol.*, 1:119 (1998).
Friesen et al., *Proc. Natl. Acad. Sci. USA*, 111:445 (2014).
Fu et al., *Nat. Commun.*, 7:12780 (2016).

Goff et al., *PLoS One*, 8:e79194 (2013).
Graves et al., *Virology*, 126:106 (1983).
Halliley et al., *J. Infect. Dis.*, 212:1270 (2015).
Henry et al., *Cell Host Microbe*, 92:800 (2016).
Henry et al., *J. Clin. Invest.*, 125-1255 (2015).
Herfst et al., *Science*, 336:1534 (2012).
Hong et al., *J. Virol.*, 87:12471 (2013).
Iba et al., *J. Virol.*, 88:7130 (2014).
Imai et al., *Nature*. 486:420 (2012).
Impagliazzo et al., *Science*, 349:1301 (2015).
Joyce et al., *Cell*, 166:609 (2016).
Kallewaard et al., *Cell*, 166:596 (2016).
Koel et al., *Science*, 342:976 (2013).
Krammer et al., *Clin. Vaccine Immunol.*, 21:1153 (2014).
Krammer et al., *J. Virol.*, 86:10302 (2012).
Krammer et al., *J. Virol.*, 87:6542 (2013).
Krammer et al., *J. Virol.*, 88:2340 (2014).
Krammer et al., *J. Virol.*, 88:3432 (2014).
Krause et al., *J. Virol.*, 85:10905 (2011).
Krause et al., *J. Virol.*, 86:6334 (2012).
Lee et al., *Nat. Commun.*, 5:3614 (2014).
Lee et al., *Proc. Natl. Acad. Sci. USA*, 109:17040 (2012).
Li et al., *Nat. Microbiol.*, 1:16058 (2016).
Li et al., *Proc. Natl. Acad. Sci. USA*, 109:9047 (2012).
Liu et al., *J, Infect. Dis.*, 215:518 (2017).
Luo et al., *J. Virol. Methods*, 154:121 (2008).
Mallajosyula et al., *Front. Immunol.*, 6:329 (2015).
Mallajosyula et al., *Proc. Natl. Acad. Sci. USA*, 111:E2514 (2014).
Margine et al., *J. Virol.*, 87:10435 (2013).
Margine et al., *J. Virol.*, 87:4728 (2013).
Miller et al., *J. Infect. Dis.*, 207:98 (2009).
Nachbagauer et al., *J. Virol*, 88:13260 (2014).
Nachbagauer et al., *J. Virol.*, 90:3268 (2015).
Nachbagauer et al., *MBio*, 7:e01996 (2016).
Nachbagauer et al., *NPJ Vaccines*, 1:e00018 (2016).
Nachbagauer et al., *NPJ Vaccines*, 2:26 (2017).
Nakamura et al., *Cell Host Microbe*, 14:93 (2013).
Neumann et al., *Proc. Natl. Acad. Sci. USA*, 96:9345 (1999).
Ohshima et al., *J. Virol.*, 85:11048 (2011).
Okuno et al., *J. Virol.*, 67:2552 (1993).
Pica et al., *Proc. Natl. Acad. Sci. USA*, 109:2573 (2012).
Ping et al., *Nat. Commun.*, 6:8148 (2015).
Ping et al., *Proc. Natl. Acad. Sci. USA*, 113:E8296 (2016)
Raymond et al., *Proc. Natl. Acad. Sci. USA*, 115:168 (2018).
Sakabe et al., *Virus Res.*, 158:124 (2009).
Sangster et al., *Clin. Vaccine Immunol.* 20:867 (2009).
Schmidt et al., *Proc. Natl. Acad. Sci. USA*, 110:264 (2013).
Steel et al., *MBio*, 1:e00018 (2010).
Steinbruck et al., *J. Virol.*, 88:12123 (2014).
Stevens et al., *Science*, 303:1866 (2004).
Sui et al., *Nat. Struct. Mol. Biol.*, 16:265 (2009).
Sun et al., *MBio*, :e00230 (2013).
Sutton et al., *NPJ Vaccines*, 2:35 (2017).
Taft et al., *Nat. Commun.*, 6:7491 (2015).
Tan et al., *J. Virol.*, 86:6179 (2012).
Thomson et al., *Front. Immunol.*, 3:87 (2012).
Throsby et al., *PLoS One*, 3:e3942 (2008).
Tsibane et al., *PLoS Pathog.*, 8:e1003067 (2012).
Valkenburg et al., *Sci. Rep.*, 6:22666. (2016)
Watanabe et al., *Nature*, 501:551 (2013).
Whittle et al., *Proc. Natl. Acad. Sci. USA*, 108:14216 (2011).
Wiley et al., *Annu. Rev. Biochem.*, 56:365 (1987).
Wiley et al., *Nature*. 289:373 (1981).
Wohlbold et al., *Vaccine* 33:3314 (2015).
Wrammert et al., *J. Exp. Med.*, 208:181 (2009).
Wu et al., *Nat. Commun.*, 6:7708 (2015).
Xu et al., *Nat. Struct. Mol. Biol.*, _____:_____ doi: 10.1038/nsmb.2500 (2013).
Yamayoshi et al., *EBioMedicine*, 17:182 (2017).
Yamayoshi et al., *J. Infect.*, 76:177 (2018).
Yang et al., *PLoS One*, 9:e106660 (2014).
Yao et al., *Sci. Rep.*, 7:1545 (2017).
Yassine et al., *Nat. Med.*, 21:1065 (2015).
Yoshida et al., *PLoS Pathog.*, 5:e1000350 (2009)
Zhang et al., *Science*, 341:410 (2013).
Zhu et al., *Science*, doi:10.1126/science.1239844 (2013).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to prepare a plurality of influenza virus nucleic acid molecules encoding a H3 or H5 hemagglutinin (HA) having a reduced number of immune dominant epitopes, comprising: introducing random mutations at a plurality of codons in one or more immune dominant epitopes in an isolated parental influenza virus nucleic acid molecule encoding an influenza virus H3 or H5 hemagglutinin having at least two immune dominant epitopes, thereby providing a library of influenza virus nucleic acid molecules encoding a mutant H3 or H5 influenza virus hemagglutinin; introducing the library into cells so as to provide a library of cells that express the mutant hemagglutinins; and identifying a mutant hemagglutinin encoded by the library with a reduced number of the immune dominant epitopes relative to the parental hemagglutinin as a result of one or more substitutions and/or deletions at residues that form the one or more immune dominant epitopes, wherein if the mutant H3 hemagglutinin has substitutions, the mutant H3 hemagglutinin has more than five substitutions relative to the parental H3 hemagglutinin.

2. The method of claim 1 wherein at least 5, 10, 15 or 20 codons, or any integer between 5 and 20, are mutated.

3. The method of claim 1 wherein the immune dominant epitope that is mutated corresponds to residues 121 to 146 in H3 HA (site A), residues 156 to 196 in H3 HA (site B), residues 50 to 57 or 275 to 279 in H3 HA (site C), residue 164, residue 182 or residues 208 to 217 in H3 HA (site D) or residues 62 to 83 in H3 HA (site E).

4. The method of claim 1 wherein the cells are mammalian cells.

5. The method of claim 1 wherein the mutant HA has a substitution at two or more of positions 121, 131, 135, 138, 140, 142, 144, 145, 155, 156, 157, 158, 171, 189, 193, 212, or 225, or a deletion at one or more of positions 121, 131, 135, 138, 140, 142, 144, 145, 155, 156, 157, 158, 171, 189, 193, 212, or 225, in H3, or a combination thereof.

6. The method of claim 1 wherein the residue in H3 at position 121 is Q, R, I, L, V, T, S, F, Y or A, position 131 is R, K, <M, V, S, Q, C, V, Y, D, E, or L, position 135 is Y, G, R, M, K, N, V, W, S, V, or P, position 138 is S, W, K, I, R, or L, position 140 is L, M, T, S, R K, M, or P, position 142 is N, D, G, Y, Q, E, H, N, L, or P, position 144 is T, K, V, G, D, H, L or Q, position 145 is P, R, W or K, position 155 is C, I, F, H, R, A, V, S or N, position 156 is P, M, R, G, S, T, A, or C, position 157 is D, P, S, G, I, R or T, position 158 is R, V, S, A, K, C, Q, position 171 is T, F, L, E, H, C or R, position 189 is A, P, T, L, A, S, Y, or R, position 193 is Q, R, N, T, E, V, or P, position 212 is V, R, G, S, M, D or E, or position 225 is L, P, C, S, Q, G, Y, or F.

7. The method of claim 1 wherein the residue in H5 at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H.

8. A method to prepare an influenza virus encoding a mutant hemagglutinin that has fewer immune dominant epitopes relative to a parental influenza virus, comprising: introducing a mutation in a parental H3 HA nucleic acid molecule at two or more codons for residue 121, 131, 135, 138, 140, 142, 144, 145, 155, 156, 157, 158, 171, 189, 193, 212, or 225, wherein the mutation encodes a residue that is not an immune dominant epitope residue in the parent H3 HA or introducing a mutation in a parental H5 HA nucleic acid molecule at two or more codons for residue 119, 123, 125, 126, 127, 129, 138, 140, 141, 151, 152, 153, 154, 155, 156, 185, or 189, wherein the mutation encodes a residue that is not an immune dominant epitope residue in the parent H5 HA; and isolating or preparing one or more influenza viruses with the mutated H3 or H5 HA, wherein the mutated H3 nucleic acid has more than five of the codons mutated, and wherein numbering for H3 is H3 numbering.

9. The method of claim 8 wherein the residue in the mutated H3 HA at position 121 is Q, R, I, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F.

10. The method of claim 8 wherein the residue in H5 at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K: position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H.

11. A composition comprising a plurality of distinct isolated recombinant influenza viruses each encoding a H3 or H5 hemagglutinin comprising a plurality of antigenically distinct residues relative to residues that form an immune dominant epitope in a parent virus, wherein each of the plurality of influenza viruses comprises substitutions at two or more of positions 121, 131, 135, 138, 140, 142, 144, 145, 155, 156, 157, 158, 171, 189, 193, 212, or 225, or one or more deletions of positions 121, 131, 135, 138, 140, 142, 144, 145, 155, 156, 157, 158, 171, 189, 193, 212, or 225, in H3, or any combination thereof, relative to the parent virus H3 hemagglutinin; or wherein each of the plurality of influenza viruses comprises a substitution at two or more of positions 119, 123, 125, 126, 127, 129, 138, 140, 141, 151, 152, 153, 154, 155, 156, 185, or 189, or a deletion in one or more of positions 119, 123, 125, 126, 127, 129, 138, 140, 141, 151, 152, 153, 154, 155, 156, 185, or 189, in H5, or any combination thereof, relative to the parent virus H5 hemagglutinin virus, wherein at least one of the plurality of distinct recombinant H3 viruses has a H3 hemagglutinin with more than five substitutions relative to the parental virus H3 hemagglutinin.

12. The composition of claim 11 which has at least three, four or five distinct viruses with the substitutions.

13. The composition of claim 11 which has five to ten distinct viruses with the substitutions.

14. The composition of claim 11 which has ten to twenty distinct viruses with the substitutions.

15. The composition of claim 11 wherein each distinct virus has at least one to five substitutions in antigenic site A or site B.

16. The composition of claim 11 wherein each distinct virus has at least one to ten substitutions in antigenic sites A and B.

17. The composition of claim 11 wherein each distinct virus has altered binding to antibodies that bind the corresponding parental hemagglutinin.

18. The composition of claim 11 wherein one of the influenza viruses comprises a) a H5 HA where the residue at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H, or any combination of those residues at those positions; or b) a H3 HA wherein the residue at position 121 is Q, R, I, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F, or any combination of those residues at those positions.

19. A method to immunize an animal, comprising: administering an effective amount of a composition comprising a plurality of distinct isolated recombinant influenza viruses each encoding a H3 or H5 hemagglutinin comprising a plurality of antigenically distinct residues relative to residues that form an immune dominant epitope in a parent virus, wherein each of the plurality of influenza viruses comprises substitutions at two or more of positions 121, 131, 135, 138, 140, 142, 144, 145, 155, 156, 157, 158, 171, 189, 193, 212, or 225, or one or more deletions of positions 121, 131, 135, 138, 140, 142, 144, 145, 155, 156, 157, 158, 171, 189, 193, 212, or 225, in H3, or any combination thereof relative to the parent virus H3 hemagglutinin; or wherein each of the plurality of influenza viruses comprises a substitution at two or more of positions 119, 123, 125, 126, 127, 129, 138, 140, 141, 151, 152, 153, 154, 155, 156, 185, or 189, or a deletion in one or more of positions 119, 123, 125, 126, 127, 129, 138, 140, 141, 151, 152, 153, 154, 155, 156, 185, or 189, in H5, or any combination thereof, relative to the parent virus H5 hemagglutinin to an animal.

* * * * *

SEQUENCE LISTING

```
<160> NUMBER OF SEQ ID NOS: 51

<210> SEQ ID NO 1
<211> LENGTH: 329
<212> TYPE: PRT
<213> ORGANISM: Influenza A

<400> SEQUENCE: 1

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Gly Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80
```

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Cys Lys Arg Arg Ser Asn
    130                 135                 140

Asn Ser Phe Phe Ser Arg Leu Asn Trp Leu Thr His Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asn Asn Asp Gln Ile
            180                 185                 190

Ser Leu Tyr Thr Gln Ala Ser Gly Arg Ile Thr Val Ser Thr Lys Arg
        195                 200                 205

Ser Gln Gln Thr Val Ile Pro Asn Ile Gly Ser Arg Pro Arg Val Arg
    210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg
                325

<210> SEQ ID NO 2
<211> LENGTH: 567
<212> TYPE: PRT
<213> ORGANISM: Influenza A

<400> SEQUENCE: 2

Met Glu Lys Ile Val Leu Leu Leu Ala Val Ile Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Thr Leu Asn
            100                 105                 110

Asp Tyr Glu Glu Leu Lys His Leu Leu Ser Arg Ile Asn His Phe Glu

```
                115                 120                 125
Lys Thr Leu Ile Ile Pro Arg Ser Ser Trp Pro Asn His Glu Thr Ser
130                 135                 140

Leu Gly Val Ser Ala Ala Cys Pro Tyr Gln Gly Ala Ser Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
            180                 185                 190

Gly Ile His His Ser Asn Asn Ala Ala Glu Gln Thr Asn Leu Tyr Lys
        195                 200                 205

Asn Pro Asp Thr Tyr Val Ser Val Gly Thr Ser Thr Leu Asn Gln Arg
    210                 215                 220

Leu Val Pro Lys Ile Ala Thr Arg Ser Gln Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Met Glu Tyr Gly
        275                 280                 285

His Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Lys Tyr Ser Glu Glu Ala Ile
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
    530                 535                 540
```

```
Ala Ile Ile Val Ala Gly Leu Ser Leu Trp Met Cys Ser Asn Gly Ser
545                 550                 555                 560

Leu Gln Cys Arg Ile Cys Ile
                565
```

<210> SEQ ID NO 3
<211> LENGTH: 564
<212> TYPE: PRT
<213> ORGANISM: Influenza A

<400> SEQUENCE: 3

```
Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
```

```
                      340                 345                 350
Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys

<210> SEQ ID NO 4
<211> LENGTH: 562
<212> TYPE: PRT
<213> ORGANISM: Influenza A

<400> SEQUENCE: 4

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
```

```
            145                 150                 155                 160
        Met Val Trp Leu Thr Glu Lys Gly Ser Asn Tyr Pro Val Ala Lys Gly
                        165                 170                 175

Ser Tyr Asn Asn Thr Ser Gly Glu Gln Met Leu Ile Ile Trp Gly Val
                        180                 185                 190

His His Pro Asn Asp Glu Thr Glu Gln Arg Thr Leu Tyr Gln Asn Val
                        195                 200                 205

Gly Thr Tyr Val Ser Val Gly Thr Ser Thr Leu Asn Lys Arg Ser Thr
                        210                 215                 220

Pro Glu Ile Ala Thr Arg Pro Lys Val Asn Gly Gln Gly Gly Arg Met
        225                 230                 235                 240

Glu Phe Ser Trp Thr Leu Leu Asp Met Trp Asp Thr Ile Asn Phe Glu
                        245                 250                 255

Ser Thr Gly Asn Leu Ile Ala Pro Glu Tyr Gly Phe Lys Ile Ser Lys
                        260                 265                 270

Arg Gly Ser Ser Gly Ile Met Lys Thr Glu Gly Thr Leu Glu Asn Cys
                        275                 280                 285

Glu Thr Lys Cys Gln Thr Pro Leu Gly Ala Ile Asn Thr Thr Leu Pro
                        290                 295                 300

Phe His Asn Val His Pro Leu Thr Ile Gly Glu Cys Pro Lys Tyr Val
        305                 310                 315                 320

Lys Ser Glu Lys Leu Val Leu Ala Thr Gly Leu Arg Asn Val Pro Gln
                        325                 330                 335

Ile Glu Ser Arg Gly Leu Phe Gly Ala Ile Ala Gly Phe Ile Glu Gly
                        340                 345                 350

Gly Trp Gln Gly Met Val Asp Gly Trp Tyr Gly Tyr His His Ser Asn
                        355                 360                 365

Asp Gln Gly Ser Gly Tyr Ala Ala Asp Lys Glu Ser Thr Gln Lys Ala
                        370                 375                 380

Phe Asp Gly Ile Thr Asn Lys Val Asn Ser Val Ile Glu Lys Met Asn
        385                 390                 395                 400

Thr Gln Phe Glu Ala Val Gly Lys Glu Phe Ser Asn Leu Glu Arg Arg
                        405                 410                 415

Leu Glu Asn Leu Asn Lys Lys Met Glu Asp Gly Phe Leu Asp Val Trp
                        420                 425                 430

Thr Tyr Asn Ala Glu Leu Leu Val Leu Met Glu Asn Glu Arg Thr Leu
                        435                 440                 445

Asp Phe His Asp Ser Asn Val Lys Asn Leu Tyr Asp Lys Val Arg Met
        450                 455                 460

Gln Leu Arg Asp Asn Val Lys Glu Leu Gly Asn Gly Cys Phe Glu Phe
        465                 470                 475                 480

Tyr His Lys Cys Asp Asp Glu Cys Met Asn Ser Val Lys Asn Gly Thr
                        485                 490                 495

Tyr Asp Tyr Pro Lys Tyr Glu Glu Ser Lys Leu Asn Arg Asn Glu
                        500                 505                 510

Ile Lys Gly Val Lys Leu Ser Ser Met Gly Val Tyr Gln Ile Leu Ala
                        515                 520                 525

Ile Tyr Ala Thr Val Ala Gly Ser Leu Ser Leu Ala Ile Met Met Ala
                        530                 535                 540

Gly Ile Ser Phe Trp Met Cys Ser Asn Gly Ser Leu Gln Cys Arg Ile
        545                 550                 555                 560

Cys Ile
```

```
<210> SEQ ID NO 5
<211> LENGTH: 562
<212> TYPE: PRT
<213> ORGANISM: Influenza A

<400> SEQUENCE: 5

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Glu Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380
```

-continued

```
Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
            405                 410                 415

Leu Glu Asn Leu Asn Lys Lys Met Glu Asp Gly Phe Leu Asp Val Trp
        420                 425                 430

Thr Tyr Asn Ala Glu Leu Leu Val Leu Met Glu Asn Glu Arg Thr Leu
    435                 440                 445

Asp Phe His Asp Ser Asn Val Lys Asn Leu Tyr Asp Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile

<210> SEQ ID NO 6
<211> LENGTH: 512
<212> TYPE: PRT
<213> ORGANISM: Influenza A

<400> SEQUENCE: 6

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Gly Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Lys Arg Arg Ser Asn
    130                 135                 140

Asn Ser Phe Phe Ser Arg Leu Asn Trp Leu Thr His Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asn Asn Asp Gln Ile
            180                 185                 190
```

```
Ser Leu Tyr Ala Gln Ala Ser Gly Arg Ile Thr Val Ser Thr Lys Arg
        195                 200                 205

Ser Gln Gln Thr Val Ile Pro Asn Ile Gly Ser Arg Pro Arg Val Arg
    210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
            275                 280                 285

Pro Asn Asp Lys Pro Phe Gln Asn Val Asn Arg Ile Thr Tyr Gly Ala
        290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Ile Gly Gln Ala Ala Asp Leu Lys
        355                 360                 365

Ser Thr Gln Ala Ala Ile Asn Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Arg Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

<210> SEQ ID NO 7
<211> LENGTH: 512
<212> TYPE: PRT
<213> ORGANISM: Influenza A

<400> SEQUENCE: 7

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Gly Ile Cys Asp Ser Pro His Gln Ile Leu Asp Gly Glu Asn Cys
```

-continued

```
                50                  55                  60
Thr Leu Ile Asp Ala Leu Leu Gly Asp Pro Gln Cys Asp Gly Phe Gln
 65                  70                  75                  80

Asn Lys Lys Trp Asp Leu Phe Val Glu Arg Ser Lys Ala Tyr Ser Asn
                 85                  90                  95

Cys Tyr Pro Tyr Asp Val Pro Asp Tyr Ala Ser Leu Arg Ser Leu Val
                100                 105                 110

Ala Ser Ser Gly Thr Leu Glu Phe Asn Asn Glu Ser Phe Asn Trp Thr
                115                 120                 125

Gly Val Thr Gln Asn Gly Thr Ser Ser Cys Lys Arg Arg Ser Asn
                130                 135                 140

Asn Ser Phe Phe Ser Arg Leu Asn Trp Leu Thr His Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asn Asn Asp Gln Ile
                180                 185                 190

Ser Leu Tyr Thr Gln Ala Ser Gly Arg Ile Thr Val Ser Thr Lys Arg
                195                 200                 205

Ser Gln Gln Thr Val Ile Pro Asn Ile Gly Ser Arg Pro Arg Val Arg
210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
                260                 265                 270

Pro Ile Gly Lys Cys Asn Ser Glu Cys Ile Thr Pro Asn Gly Ser Ile
                275                 280                 285

Pro Asn Asp Lys Pro Phe Gln Asn Val Asn Arg Ile Thr Tyr Gly Ala
                290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
                340                 345                 350

Phe Arg His Gln Asn Ser Glu Gly Ile Gly Gln Ala Ala Asp Leu Lys
                355                 360                 365

Ser Thr Gln Ala Ala Ile Asn Gln Ile Asn Gly Lys Leu Asn Arg Leu
                370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
                420                 425                 430

Asn Gln His Thr Ile Asp Leu Thr Asp Ser Glu Met Asn Lys Leu Phe
                435                 440                 445

Glu Arg Thr Lys Lys Gln Leu Arg Glu Asn Ala Glu Asp Met Gly Asn
                450                 455                 460

Gly Cys Phe Lys Ile Tyr His Lys Cys Asp Asn Ala Cys Ile Gly Ser
465                 470                 475                 480
```

```
Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510
```

<210> SEQ ID NO 8
<211> LENGTH: 566
<212> TYPE: PRT
<213> ORGANISM: Influenza A

<400> SEQUENCE: 8

```
Met Lys Thr Ile Ile Ala Leu Ser Cys Ile Leu Cys Leu Val Phe Thr
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Asn Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Ala
130                 135                 140

Gly Val Thr Gln Asn Gly Thr Ser Ser Ser Cys Ile Arg Gly Ser Lys
145                 150                 155                 160

Ser Ser Phe Phe Ser Arg Leu Asn Trp Leu Thr His Leu Asn Ser Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Ser Leu Tyr Ala Gln Ser Ser Gly Arg Ile Thr Val Ser Thr Lys Arg
210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Arg Gln Thr Arg Gly Ile Phe Gly Ala Ile Ala
```

```
                   340                 345                 350
Gly Phe Ile Glu Asn Gly Trp Glu Gly Met Val Asp Gly Trp Tyr Gly
                355                 360                 365
Phe Arg His Gln Asn Ser Glu Gly Arg Gly Gln Ala Ala Asp Leu Lys
            370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
    450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asn Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
    530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 9
<211> LENGTH: 567
<212> TYPE: PRT
<213> ORGANISM: Influenza A

<400> SEQUENCE: 9

Met Glu Lys Ile Val Leu Leu Leu Ala Val Ile Ser Leu Val Lys Ser
1               5                   10                  15
Asp Gln Ile Cys Ile Gly Tyr His Ala Asn Asn Ser Thr Lys Gln Val
            20                  25                  30
Asp Thr Ile Met Glu Lys Asn Val Thr Val Thr His Ala Gln Asp Ile
        35                  40                  45
Leu Glu Lys Thr His Asn Gly Lys Leu Cys Asp Leu Asn Gly Val Lys
    50                  55                  60
Pro Leu Ile Leu Lys Asp Cys Ser Val Ala Gly Trp Leu Leu Gly Asn
65                  70                  75                  80
Pro Met Cys Asp Glu Phe Ile Arg Val Pro Glu Trp Ser Tyr Ile Val
                85                  90                  95
Glu Arg Ala Asn Pro Ala Asn Asp Leu Cys Tyr Pro Gly Thr Leu Asn
            100                 105                 110
Asp Tyr Glu Glu Leu Lys His Leu Leu Ser Arg Ile Asn His Phe Glu
        115                 120                 125
Lys Thr Leu Ile Ile Pro Arg Ser Ser Trp Pro Asn His Glu Thr Ser
    130                 135                 140
```

```
Leu Gly Val Ser Ala Ala Cys Pro Tyr Gln Gly Ala Ser Ser Phe Phe
145                 150                 155                 160

Arg Asn Val Val Trp Leu Ile Lys Lys Asn Asp Ala Tyr Pro Thr Ile
                165                 170                 175

Lys Ile Ser Tyr Asn Asn Thr Asn Arg Glu Asp Leu Leu Ile Leu Trp
                180                 185                 190

Gly Ile His His Ser Asn Asn Ala Ala Glu Gln Thr Asn Leu Tyr Lys
                195                 200                 205

Asn Pro Asp Thr Tyr Val Ser Val Gly Thr Ser Thr Leu Asn Gln Arg
210                 215                 220

Leu Val Pro Lys Ile Ala Thr Arg Ser Gln Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Met Glu Tyr Gly
                275                 280                 285

His Cys Asn Thr Lys Cys Gln Thr Pro Ile Gly Ala Ile Asn Ser Ser
                290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Lys Arg Gly Leu Phe Gly Ala Ile Ala
                340                 345                 350

Gly Phe Ile Glu Gly Gly Trp Gln Gly Met Val Asp Gly Trp Tyr Gly
                355                 360                 365

Tyr His His Ser Asn Glu Gln Gly Ser Gly Tyr Ala Ala Asp Lys Glu
                370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
                420                 425                 430

Phe Leu Asp Val Trp Thr Tyr Asn Ala Glu Leu Leu Val Leu Met Glu
                435                 440                 445

Asn Glu Arg Thr Leu Asp Phe His Asp Ser Asn Val Lys Asn Leu Tyr
                450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Lys Tyr Ser Glu Glu Ala Ile
                500                 505                 510

Leu Lys Arg Glu Glu Ile Ser Gly Val Lys Leu Glu Ser Ile Gly Thr
                515                 520                 525

Tyr Gln Ile Leu Ser Ile Tyr Ser Thr Val Ala Ser Ser Leu Ala Leu
                530                 535                 540

Ala Ile Ile Val Ala Gly Leu Ser Leu Trp Met Cys Ser Asn Gly Ser
545                 550                 555                 560

Leu Gln Cys Arg Ile Cys Ile
```

```
<210> SEQ ID NO 10
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 10

Asn Thr Thr Ala Ile Arg Ser Ser Thr His Leu Asn Asn Lys Phe Ala
1               5                   10                  15

Asp

<210> SEQ ID NO 11
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 11

Tyr Val Val Lys Trp Ser Gly Pro Val Gly Val Arg Asp Asn Glx Gln
1               5                   10                  15

Lys

<210> SEQ ID NO 12
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 12

Met Val Gly Asp Phe Thr Asp Arg Cys Ala Asn Gly Arg Glu Gly Asn
1               5                   10                  15

Lys

<210> SEQ ID NO 13
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 13

Lys Arg Gly Ala Pro Asp Ala Gly Met Thr Ser Pro Lys Asp Gly Leu
1               5                   10                  15

Glu

<210> SEQ ID NO 14
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 14

Gln Arg Thr Lys Leu Asn Thr Pro Cys Pro Asp Arg Thr Ala Gln Val
1               5                   10                  15

Leu

<210> SEQ ID NO 15
```

```
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 15

Val Arg Arg Phe Met Asn Thr Trp Val Ala Leu His Thr Ile Ser Arg
1               5                   10                  15
Pro

<210> SEQ ID NO 16
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 16

Val Lys Val Thr His Glu Arg Arg Ala Ser Pro Val Arg Arg Thr Ile
1               5                   10                  15
Ser

<210> SEQ ID NO 17
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 17

Arg Val Lys Trp Met Gly Val Pro Ile Gly Pro Val Phe Thr Arg Arg
1               5                   10                  15
Pro

<210> SEQ ID NO 18
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 18

Thr Gly Leu Arg Cys Ser Gly Arg Tyr Pro Leu Gln Thr Phe Ala Arg
1               5                   10                  15
Thr

<210> SEQ ID NO 19
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 19

Ile Thr Asn Lys Thr Tyr Asp Ser Arg Ser Ser Ser Phe Ala Gln Gly
1               5                   10                  15
Cys

<210> SEQ ID NO 20
<211> LENGTH: 17
<212> TYPE: PRT
<213> ORGANISM: Artificial Sequence
<220> FEATURE:
```

<223> OTHER INFORMATION: A mutant amino acid sequence

<400> SEQUENCE: 20

Val Met Leu Lys Thr Gly Ala Trp Gln Ser Arg Leu Gln Leu Arg Arg
1               5                   10                  15

Glu

<210> SEQ ID NO 21
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 21

Ala Lys Ser Arg Asn Asp Gly Val Arg Ser Arg Phe Thr Glu Ala Tyr
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 22

Val Cys Asn Ile Lys Arg Pro Asp Ala Ala Gly Ala Leu Ala Pro Ser
1               5                   10                  15

Ser

<210> SEQ ID NO 23
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 23

Val Cys Leu Leu Arg Phe Lys Thr Ile Pro Ser Pro Gln Asn Ser Thr
1               5                   10                  15

Ser

<210> SEQ ID NO 24
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 24

Ser Ser Thr Lys Ser Gln Gly Ser Arg Pro Ile Lys Glu Pro Asn Val
1               5                   10                  15

Gln

<210> SEQ ID NO 25
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 25

Val Gln Val Arg Arg Glu His Ser Val Thr Leu Arg His Leu Thr Met
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 26

Leu Arg Asn Thr Lys Thr Asn Ser Gln Lys Arg Phe Ser Phe Thr Val
1               5                   10                  15

Ser

<210> SEQ ID NO 27
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 27

Arg Arg Ile Val Asn Gly Thr Arg Trp Pro Ser Pro Arg Ser Ser Val
1               5                   10                  15

Arg

<210> SEQ ID NO 28
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 28

Val Arg Tyr Lys Thr Ala Glu Gln Thr Leu Trp Gly Arg Tyr Gln Met
1               5                   10                  15

Asn

<210> SEQ ID NO 29
<211> LENGTH: 16
<212> TYPE: PRT
<213> ORGANISM: Artificial Sequence
<220> FEATURE:
<223> OTHER INFORMATION: A mutant amino acid sequence

<400> SEQUENCE: 29

Phe Asp Ser Lys Gly Asn Val Lys Pro Thr Arg Arg Leu Ser Pro Ser
1               5                   10                  15

<210> SEQ ID NO 30
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 30

Ser Arg Lys Thr Asn Arg Ala Pro Gln His Met Lys Phe Thr Asn Phe
1               5                   10                  15

Cys

```
<210> SEQ ID NO 31
<211> LENGTH: 17
<212> TYPE: PRT
<213> ORGANISM: Artificial Sequence
<220> FEATURE:
<223> OTHER INFORMATION: A mutant amino acid sequence

<400> SEQUENCE: 31

Phe Val Trp Ser Met His Gln Pro Gln Gly Arg Cys Thr Ser Glu Ala
1               5                   10                  15

Tyr

<210> SEQ ID NO 32
<211> LENGTH: 326
<212> TYPE: PRT
<213> ORGANISM: Influenza A

<400> SEQUENCE: 32

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Ser His Asn Gly Lys Leu Cys Leu Leu Lys Gly Ile Ala
            35                  40                  45

Pro Leu Gln Leu Gly Asn Cys Ser Val Ala Gly Trp Ile Leu Gly Asn
50                  55                  60

Pro Glu Cys Glu Leu Leu Ile Ser Lys Glu Ser Trp Ser Tyr Ile Val
65                  70                  75                  80

Glu Thr Pro Asn Pro Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Lys Ser Ser Phe Tyr
130                 135                 140

Arg Asn Leu Leu Trp Ile Thr Gly Lys Asn Gly Leu Tyr Pro Asn Leu
145                 150                 155                 160

Ser Lys Ser Tyr Val Asn Asn Lys Glu Lys Glu Val Leu Val Leu Trp
                165                 170                 175

Gly Val His His Pro Pro Asn Ile Gly Asn Gln Arg Ala Leu Tyr His
            180                 185                 190

Thr Glu Asn Ala Tyr Val Ser Val Ser Ser His Tyr Ser Arg Arg
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Trp Tyr Ala Phe Ala Leu
                245                 250                 255

Ser Arg Gly Phe Gly Ser Gly Ile Ile Thr Ser Asn Ala Pro Met Asp
            260                 265                 270

Glu Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300
```

```
Tyr Val Arg Ser Ala Lys Leu Arg Met Val Thr Gly Leu Arg Asn Ile
305                 310                 315                 320

Pro Ser Ile Gln Ser Arg
            325
```

<210> SEQ ID NO 33
<211> LENGTH: 327
<212> TYPE: PRT
<213> ORGANISM: Influenza A

<400> SEQUENCE: 33

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Lys His Asn Gly Lys Leu Cys Lys Leu Arg Gly Val Ala
            35                  40                  45

Pro Leu His Leu Gly Lys Cys Asn Ile Ala Gly Trp Ile Leu Gly Asn
50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Thr Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
290                 295                 300

Lys Tyr Val Lys Ser Thr Lys Leu Arg Leu Ala Thr Gly Leu Arg Asn
305                 310                 315                 320

Ile Pro Ser Ile Gln Ser Arg
            325
```

<210> SEQ ID NO 34

```
<211> LENGTH: 325
<212> TYPE: PRT
<213> ORGANISM: Influenza A

<400> SEQUENCE: 34

Asp Gln Ile Cys Ile Gly Tyr His Ala Asn Asn Ser Thr Glu Lys Val
1               5                   10                  15

Asp Thr Ile Leu Glu Arg Asn Val Thr Val Thr His Ala Lys Asp Ile
            20                  25                  30

Leu Glu Lys Thr His Asn Gly Lys Leu Cys Lys Leu Asn Gly Ile Pro
        35                  40                  45

Pro Leu Glu Leu Gly Asp Cys Ser Ile Ala Gly Trp Leu Leu Gly Asn
    50                  55                  60

Pro Glu Cys Asp Arg Leu Leu Ser Val Pro Glu Trp Ser Tyr Ile Met
65                  70                  75                  80

Glu Lys Glu Asn Pro Arg Asp Gly Leu Cys Tyr Pro Gly Ser Phe Asn
                85                  90                  95

Asp Tyr Glu Glu Leu Lys His Leu Leu Ser Ser Val Lys His Phe Glu
            100                 105                 110

Lys Val Lys Ile Leu Pro Lys Asp Arg Trp Thr Gln His Thr Thr Thr
        115                 120                 125

Gly Gly Ser Arg Ala Cys Ala Val Ser Gly Asn Pro Ser Phe Phe Arg
    130                 135                 140

Asn Met Val Trp Leu Thr Lys Lys Glu Ser Asn Tyr Pro Val Ala Lys
145                 150                 155                 160

Gly Ser Tyr Asn Asn Thr Ser Gly Glu Gln Met Leu Ile Ile Trp Gly
                165                 170                 175

Val His His Pro Asn Asp Glu Thr Glu Gln Arg Thr Leu Tyr Gln Asn
            180                 185                 190

Val Gly Thr Tyr Val Ser Val Gly Thr Ser Thr Leu Asn Lys Arg Ser
        195                 200                 205

Thr Pro Asp Ile Ala Thr Arg Pro Lys Val Asn Gly Leu Gly Ser Arg
    210                 215                 220

Met Glu Phe Ser Trp Thr Leu Leu Asp Met Trp Asp Thr Ile Asn Phe
225                 230                 235                 240

Glu Ser Thr Gly Asn Leu Ile Ala Pro Glu Tyr Gly Phe Lys Ile Ser
                245                 250                 255

Lys Arg Gly Ser Ser Gly Ile Met Lys Thr Glu Gly Thr Leu Glu Asn
            260                 265                 270

Cys Glu Thr Lys Cys Gln Thr Pro Leu Gly Ala Ile Asn Thr Thr Leu
        275                 280                 285

Pro Phe His Asn Val His Pro Leu Thr Ile Gly Glu Cys Pro Lys Tyr
    290                 295                 300

Val Lys Ser Glu Lys Leu Val Leu Ala Thr Gly Leu Arg Asn Val Pro
305                 310                 315                 320

Gln Ile Glu Ser Arg
                325

<210> SEQ ID NO 35
<211> LENGTH: 326
<212> TYPE: PRT
<213> ORGANISM: Influenza A

<400> SEQUENCE: 35

Asp Gln Ile Cys Ile Gly Tyr His Ala Asn Asn Ser Thr Glu Gln Val
1               5                   10                  15
```

-continued

Asp Thr Ile Met Glu Lys Asn Val Thr Val Thr His Ala Gln Asp Ile
                20                  25                  30

Leu Glu Lys Ala His Asn Gly Lys Leu Cys Ser Leu Asn Gly Val Lys
            35                  40                  45

Pro Leu Ile Leu Arg Asp Cys Ser Val Ala Gly Trp Leu Leu Gly Asn
 50                  55                  60

Pro Met Cys Asp Glu Phe Leu Asn Val Pro Glu Trp Ser Tyr Ile Val
 65                  70                  75                  80

Glu Lys Asp Asn Pro Ile Asn Gly Leu Cys Tyr Pro Gly Asp Phe Asn
                85                  90                  95

Asp Tyr Glu Glu Leu Lys His Leu Leu Ser Ser Thr Asn His Phe Glu
            100                 105                 110

Lys Ile Gln Ile Ile Pro Arg Ser Ser Trp Ser Asn His Glu Ala Ser
        115                 120                 125

Ser Gly Val Ser Ser Ala Cys Pro Tyr Asn Gly Arg Ser Ser Phe Phe
130                 135                 140

Arg Asn Val Val Trp Ile Ile Lys Lys Asn Asn Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Val Ser Val Gly Thr Ser Thr Leu Asn Gln Arg
        195                 200                 205

Ser Val Pro Glu Ile Ala Thr Arg Pro Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Gly Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asp Arg Leu Val Leu Ala Thr Gly Leu Arg Asn Val
305                 310                 315                 320

Pro Gln Arg Glu Thr Arg
                325

<210> SEQ ID NO 36
<211> LENGTH: 329
<212> TYPE: PRT
<213> ORGANISM: Influenza A

<400> SEQUENCE: 36

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
                20                  25                  30

Leu Glu Lys Thr His Asn Gly Lys Leu Cys Asn Leu Asp Gly Val Lys
            35                  40                  45

Pro Leu Ile Leu Arg Asp Cys Ser Val Ala Gly Trp Leu Leu Gly Asn

```
Pro Met Cys Asp Glu Phe Leu Asn Val Pro Glu Trp Ser Tyr Ile Val
65                  70                  75                  80

Glu Lys Ile Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Asn Ser Trp Ser Asp His Glu Ala Ser
        115                 120                 125

Gly Val Ser Ser Ala Cys Pro Tyr Gln Gly Arg Ser Ser Phe Phe Arg
    130                 135                 140

Asn Val Val Trp Leu Thr Lys Lys Asp Asn Ala Tyr Pro Thr Ile Lys
145                 150                 155                 160

Arg Ser Tyr Asn Asn Thr Asn Gln Glu Asp Leu Leu Val Leu Trp Gly
                165                 170                 175

Ile His His Pro Asn Asp Ala Ala Glu Gln Thr Arg Leu Tyr Gln Asn
            180                 185                 190

Pro Thr Thr Tyr Ile Ser Val Gly Thr Ser Thr Leu Asn Gln Arg Leu
        195                 200                 205

Val Pro Lys Ile Ala Thr Arg Ser Lys Val Asn Gly Gln Ser Gly Arg
    210                 215                 220

Met Glu Phe Phe Trp Thr Ile Leu Lys Ser Asn Asp Ala Ile Asn Phe
225                 230                 235                 240

Glu Ser Asn Gly Asn Phe Ile Ala Pro Glu Asn Ala Tyr Lys Ile Val
                245                 250                 255

Lys Lys Gly Asp Ser Thr Ile Met Lys Ser Glu Leu Glu Tyr Gly Asn
            260                 265                 270

Cys Asn Thr Lys Cys Gln Thr Pro Ile Gly Ala Ile Asn Ser Ser Met
        275                 280                 285

Pro Phe His Asn Ile His Pro Leu Thr Ile Gly Glu Cys Pro Lys Tyr
    290                 295                 300

Val Lys Ser Asn Arg Leu Val Leu Ala Thr Gly Leu Arg Asn Ser Pro
305                 310                 315                 320

Gln Arg Glu Arg Arg Arg Lys Lys Arg
                325

<210> SEQ ID NO 37
<211> LENGTH: 329
<212> TYPE: PRT
<213> ORGANISM: Influenza A

<400> SEQUENCE: 37

Asp Lys Ile Cys Ile Gly Tyr His Ala Asn Asn Ser Thr Thr Gln Val
1               5                   10                  15

Asp Thr Ile Leu Glu Lys Asn Val Thr Val Thr His Ser Val Glu Leu
            20                  25                  30

Leu Glu Asn Gln Lys Glu Glu Arg Phe Cys Lys Ile Met Asn Lys Ser
        35                  40                  45

Pro Leu Asp Leu Arg Glu Cys Thr Ile Glu Gly Trp Ile Leu Gly Asn
    50                  55                  60

Pro Lys Cys Asp Leu Leu Leu Gly Asp Gln Ser Trp Ser Tyr Ile Val
65                  70                  75                  80

Glu Arg Pro Thr Ala Gln Asn Gly Ile Cys Tyr Pro Gly Ala Leu Asn
                85                  90                  95
```

Glu Val Glu Glu Leu Lys Ala Leu Ile Gly Ser Gly Glu Arg Val Glu
            100                 105                 110

Arg Phe Glu Met Phe Pro Lys Ser Thr Trp Ala Gly Val Asp Thr Ser
        115                 120                 125

Ser Gly Val Thr Asn Ala Cys Pro Ser Tyr Thr Ile Gly Ser Ser Phe
    130                 135                 140

Tyr Arg Asn Leu Val Trp Ile Ile Lys Thr Asn Ser Ala Ala Tyr Pro
145                 150                 155                 160

Val Ile Lys Gly Thr Tyr Asn Asn Thr Gly Asn Gln Pro Ile Leu Tyr
                165                 170                 175

Phe Trp Gly Val His His Pro Pro Asn Thr Gly Val Gln Asp Thr Leu
            180                 185                 190

Tyr Gly Ser Gly Glu Arg Tyr Val Arg Met Gly Thr Asp Ser Met Asn
        195                 200                 205

Phe Ala Lys Ser Pro Glu Ile Ala Glu Arg Pro Val Val Asn Gly Gln
    210                 215                 220

Arg Gly Arg Ile Asp Tyr Tyr Trp Ser Val Leu Lys Pro Gly Glu Thr
225                 230                 235                 240

Leu Asn Val Glu Ser Asn Gly Asn Leu Ile Ala Pro Trp Tyr Ala Tyr
                245                 250                 255

Lys Phe Val Ser Thr Asn Lys Lys Gly Ala Val Phe Lys Ser Asn Leu
            260                 265                 270

Pro Ile Glu Asn Cys Asp Ala Thr Cys Gln Thr Ile Ala Gly Val Leu
        275                 280                 285

Arg Thr Asn Lys Thr Phe Gln Asn Val Ser Pro Leu Trp Ile Gly Glu
    290                 295                 300

Cys Pro Lys Tyr Val Lys Ser Glu Ser Leu Arg Leu Ala Thr Gly Leu
305                 310                 315                 320

Arg Asn Ile Pro Gln Ile Lys Thr Arg
                325

<210> SEQ ID NO 38
<211> LENGTH: 328
<212> TYPE: PRT
<213> ORGANISM: Influenza A

<400> SEQUENCE: 38

Tyr Asp Arg Ile Cys Ile Gly Tyr Gln Ser Asn Asn Ser Thr Asp Thr
1               5                   10                  15

Val Asn Thr Leu Ile Glu Gln Asn Val Pro Val Thr Gln Thr Met Glu
            20                  25                  30

Leu Val Glu Thr Glu Lys His Pro Ala Tyr Cys Asn Thr Asp Leu Gly
        35                  40                  45

Ala Pro Leu Glu Leu Arg Asp Cys Lys Ile Glu Ala Val Ile Tyr Gly
    50                  55                  60

Asn Pro Lys Cys Asp Ile His Leu Lys Asp Gln Gly Trp Ser Tyr Ile
65                  70                  75                  80

Val Glu Arg Pro Ser Ala Pro Glu Gly Met Cys Tyr Pro Gly Ser Val
                85                  90                  95

Glu Asn Leu Glu Glu Leu Arg Phe Val Phe Ser Ser Ala Ala Ser Tyr
            100                 105                 110

Lys Arg Ile Arg Leu Phe Asp Tyr Ser Arg Trp Asn Val Thr Arg Ser
        115                 120                 125

Gly Thr Ser Lys Ala Cys Asn Ala Ser Thr Gly Gly Gln Ser Phe Tyr
    130                 135                 140

Arg Ser Ile Asn Trp Leu Thr Lys Lys Pro Asp Thr Tyr Asp Phe
145                 150                 155                 160

Asn Glu Gly Ala Tyr Val Asn Asn Glu Asp Gly Asp Ile Ile Phe Leu
            165                 170                 175

Trp Gly Ile His His Pro Pro Asp Thr Lys Glu Gln Thr Thr Leu Tyr
        180                 185                 190

Lys Asn Ala Asn Thr Leu Ser Ser Val Thr Thr Asn Thr Ile Asn Arg
        195                 200                 205

Ser Phe Gln Pro Asn Ile Gly Pro Arg Pro Leu Val Arg Gly Gln Gln
210                 215                 220

Gly Arg Met Asp Tyr Tyr Trp Gly Ile Leu Lys Arg Gly Glu Thr Leu
225                 230                 235                 240

Lys Ile Arg Thr Asn Gly Asn Leu Ile Ala Pro Glu Phe Gly Tyr Leu
            245                 250                 255

Leu Lys Gly Glu Ser Tyr Gly Arg Ile Ile Gln Asn Glu Asp Ile Pro
            260                 265                 270

Ile Gly Asn Cys Asn Thr Lys Cys Gln Thr Tyr Ala Gly Ala Ile Asn
        275                 280                 285

Ser Ser Lys Pro Phe Gln Asn Ala Ser Arg His Tyr Met Gly Glu Cys
290                 295                 300

Pro Lys Tyr Val Lys Lys Ala Ser Leu Arg Leu Ala Val Gly Leu Arg
305                 310                 315                 320

Asn Thr Pro Ser Val Glu Pro Arg
            325

<210> SEQ ID NO 39
<211> LENGTH: 320
<212> TYPE: PRT
<213> ORGANISM: Influenza A

<400> SEQUENCE: 39

Asp Lys Ile Cys Ile Gly Tyr Gln Ser Thr Asn Ser Thr Glu Thr Val
1               5                   10                  15

Asp Thr Leu Thr Glu Thr Asn Val Pro Val Thr His Ala Lys Glu Leu
            20                  25                  30

Leu His Thr Glu His Asn Gly Met Leu Cys Ala Thr Asn Leu Gly His
        35                  40                  45

Pro Leu Ile Leu Asp Thr Cys Thr Ile Glu Gly Leu Ile Tyr Gly Asn
    50                  55                  60

Pro Ser Cys Asp Leu Leu Leu Gly Gly Arg Glu Trp Ser Tyr Ile Val
65                  70                  75                  80

Glu Arg Pro Ser Ala Val Asn Gly Met Cys Tyr Pro Gly Asn Val Glu
            85                  90                  95

Asn Leu Glu Glu Leu Arg Ser Leu Phe Ser Ser Ala Ser Ser Tyr Gln
            100                 105                 110

Arg Ile Gln Ile Phe Pro Asp Thr Ile Trp Asn Val Ser Tyr Ser Gly
        115                 120                 125

Thr Ser Lys Ala Cys Ser Asp Ser Phe Tyr Arg Ser Met Arg Trp Leu
130                 135                 140

Thr Gln Lys Asn Asn Ala Tyr Pro Ile Gln Asp Ala Gln Tyr Thr Asn
145                 150                 155                 160

Asn Arg Gly Lys Ser Ile Leu Phe Met Trp Gly Ile Asn His Pro Pro
            165                 170                 175

Thr Asp Thr Val Gln Thr Asn Leu Tyr Thr Arg Thr Asp Thr Thr Thr

```
            180                 185                 190
Ser Val Thr Thr Glu Asp Ile Asn Arg Thr Phe Lys Pro Val Ile Gly
                195                 200                 205

Pro Arg Pro Leu Val Asn Gly Leu His Gly Arg Ile Asp Tyr Tyr Trp
            210                 215                 220

Ser Val Leu Lys Pro Gly Gln Thr Leu Arg Val Arg Ser Asn Gly Asn
225                 230                 235                 240

Leu Ile Ala Pro Trp Tyr Gly His Ile Leu Ser Gly Glu Ser His Gly
                245                 250                 255

Arg Ile Leu Lys Thr Asp Leu Asn Ser Gly Asn Cys Val Val Gln Cys
            260                 265                 270

Gln Thr Glu Arg Gly Gly Leu Asn Thr Thr Leu Pro Phe His Asn Val
            275                 280                 285

Ser Lys Tyr Ala Phe Gly Asn Cys Pro Lys Tyr Val Gly Val Lys Ser
            290                 295                 300

Leu Lys Leu Ala Val Gly Leu Arg Asn Val Pro Ala Arg Ser Ser Arg
305                 310                 315                 320
```

<210> SEQ ID NO 40
<211> LENGTH: 326
<212> TYPE: PRT
<213> ORGANISM: Influenza A

<400> SEQUENCE: 40

```
Asp Glu Ile Cys Ile Gly Tyr Leu Ser Asn Asn Ser Thr Asp Lys Val
1               5                   10                  15

Asp Thr Ile Ile Glu Asn Asn Val Thr Val Thr Ser Ser Val Glu Leu
            20                  25                  30

Val Glu Thr Glu His Thr Gly Ser Phe Cys Ser Ile Asn Gly Lys Gln
            35                  40                  45

Pro Ile Ser Leu Gly Asp Cys Ser Phe Ala Gly Trp Ile Leu Gly Asn
        50                  55                  60

Pro Met Cys Asp Glu Leu Ile Gly Lys Thr Ser Trp Ser Tyr Ile Val
65                  70                  75                  80

Glu Lys Pro Asn Pro Thr Asn Gly Ile Cys Tyr Pro Gly Thr Leu Glu
            85                  90                  95

Ser Glu Glu Glu Leu Arg Leu Lys Phe Ser Gly Val Leu Glu Phe Asn
            100                 105                 110

Lys Phe Glu Val Phe Thr Ser Asn Gly Trp Gly Ala Val Asn Ser Gly
            115                 120                 125

Val Gly Val Thr Ala Ala Cys Lys Phe Gly Gly Ser Asn Ser Phe Phe
        130                 135                 140

Arg Asn Met Val Trp Leu Ile His Gln Ser Gly Thr Tyr Pro Val Ile
145                 150                 155                 160

Lys Arg Thr Phe Asn Asn Thr Lys Gly Arg Asp Val Leu Ile Val Trp
                165                 170                 175

Gly Ile His His Pro Ala Thr Leu Thr Glu His Gln Asp Leu Tyr Lys
            180                 185                 190

Lys Asp Ser Ser Tyr Val Ala Val Gly Ser Glu Thr Tyr Asn Arg Arg
            195                 200                 205

Phe Thr Pro Glu Ile Asn Thr Arg Pro Arg Val Asn Gly Gln Ala Gly
        210                 215                 220

Arg Met Thr Phe Tyr Trp Lys Ile Val Lys Pro Gly Glu Ser Ile Thr
225                 230                 235                 240
```

```
Phe Glu Ser Asn Gly Ala Phe Leu Ala Pro Arg Tyr Ala Phe Glu Ile
                245                 250                 255

Val Ser Val Gly Asn Gly Lys Leu Phe Arg Ser Glu Leu Asn Ile Glu
            260                 265                 270

Ser Cys Ser Thr Lys Cys Gln Thr Glu Ile Gly Gly Ile Asn Thr Asn
            275                 280                 285

Lys Ser Phe His Asn Val His Arg Asn Thr Ile Gly Asp Cys Pro Lys
        290                 295                 300

Tyr Val Asn Val Lys Ser Leu Lys Leu Ala Thr Gly Pro Arg Asn Val
305                 310                 315                 320

Pro Ala Ile Ala Ser Arg
                325

<210> SEQ ID NO 41
<211> LENGTH: 326
<212> TYPE: PRT
<213> ORGANISM: Influenza A

<400> SEQUENCE: 41

Tyr Asp Lys Ile Cys Ile Gly Tyr Gln Thr Asn Asn Ser Thr Glu Thr
1               5                   10                  15

Val Asn Thr Leu Ser Glu Gln Asn Val Pro Val Thr Gln Val Glu Glu
            20                  25                  30

Leu Val His Gly Gly Ile Asp Pro Ile Leu Cys Gly Thr Glu Leu Gly
        35                  40                  45

Ser Pro Leu Val Leu Asp Asp Cys Ser Leu Glu Gly Leu Ile Leu Gly
    50                  55                  60

Asn Pro Lys Cys Asp Leu Tyr Leu Asn Gly Arg Glu Trp Ser Tyr Ile
65                  70                  75                  80

Val Glu Arg Pro Lys Glu Met Glu Gly Val Cys Tyr Pro Gly Ser Ile
                85                  90                  95

Glu Asn Gln Glu Glu Leu Arg Ser Leu Phe Ser Ser Ile Lys Lys Tyr
            100                 105                 110

Glu Arg Val Lys Met Phe Asp Phe Thr Lys Trp Asn Val Thr Tyr Thr
        115                 120                 125

Gly Thr Ser Lys Ala Cys Asn Asn Thr Ser Asn Gln Gly Ser Phe Tyr
    130                 135                 140

Arg Ser Met Arg Trp Leu Thr Leu Lys Ser Gly Gln Phe Pro Val Gln
145                 150                 155                 160

Thr Asp Glu Tyr Lys Asn Thr Arg Asp Ser Asp Ile Val Phe Thr Trp
                165                 170                 175

Ala Ile His His Pro Pro Thr Ser Asp Glu Gln Val Lys Leu Tyr Lys
            180                 185                 190

Asn Pro Asp Thr Leu Ser Ser Val Thr Thr Asp Glu Ile Asn Arg Ser
        195                 200                 205

Phe Lys Pro Asn Ile Gly Pro Arg Pro Leu Val Arg Gly Gln Gln Gly
    210                 215                 220

Arg Met Asp Tyr Tyr Trp Ala Val Leu Lys Pro Gly Gln Thr Val Lys
225                 230                 235                 240

Ile Gln Thr Asn Gly Asn Leu Ile Ala Pro Glu Tyr Gly His Leu Ile
                245                 250                 255

Thr Gly Lys Ser His Gly Arg Ile Leu Lys Asn Asn Leu Pro Met Gly
            260                 265                 270

Gln Cys Val Thr Glu Cys Gln Leu Asn Glu Gly Val Met Asn Thr Ser
        275                 280                 285
```

Lys Pro Phe Gln Asn Thr Ser Lys His Tyr Ile Gly Lys Cys Pro Lys
290                 295                 300

Tyr Ile Pro Ser Gly Ser Leu Lys Leu Ala Ile Gly Leu Arg Asn Val
305                 310                 315                 320

Pro Gln Val Gln Asp Arg
                325

<210> SEQ ID NO 42
<211> LENGTH: 325
<212> TYPE: PRT
<213> ORGANISM: Influenza A

<400> SEQUENCE: 42

Asp Arg Ile Cys Val Gly Tyr Leu Ser Thr Asn Ser Ser Glu Arg Val
1               5                   10                  15

Asp Thr Leu Leu Glu Asn Gly Val Pro Val Thr Ser Ser Ile Asp Leu
            20                  25                  30

Ile Glu Thr Asn His Thr Gly Thr Tyr Cys Ser Leu Asn Gly Val Ser
        35                  40                  45

Pro Val His Leu Gly Asp Cys Ser Phe Glu Gly Trp Ile Val Gly Asn
50                  55                  60

Pro Ala Cys Thr Ser Asn Phe Gly Ile Arg Glu Trp Ser Tyr Leu Ile
65                  70                  75                  80

Glu Asp Pro Ala Ala Pro His Gly Leu Cys Tyr Pro Gly Glu Leu Asn
                85                  90                  95

Asn Asn Gly Glu Leu Arg His Leu Phe Ser Gly Ile Arg Ser Phe Ser
            100                 105                 110

Arg Thr Glu Leu Ile Pro Pro Thr Ser Trp Gly Glu Val Leu Asp Gly
        115                 120                 125

Thr Thr Ser Ala Cys Arg Asp Asn Thr Gly Thr Asn Ser Phe Tyr Arg
130                 135                 140

Asn Leu Val Trp Phe Ile Lys Lys Asn Asn Arg Tyr Pro Val Ile Ser
145                 150                 155                 160

Lys Thr Tyr Asn Asn Thr Thr Gly Arg Asp Val Leu Val Leu Trp Gly
                165                 170                 175

Ile His His Pro Val Ser Val Asp Glu Thr Lys Thr Leu Tyr Val Asn
            180                 185                 190

Ser Asp Pro Tyr Thr Leu Val Ser Thr Lys Ser Trp Ser Glu Lys Tyr
        195                 200                 205

Lys Leu Glu Thr Gly Val Arg Pro Gly Tyr Asn Gly Gln Arg Ser Trp
210                 215                 220

Met Lys Ile Tyr Trp Ser Leu Ile His Pro Gly Glu Met Ile Thr Phe
225                 230                 235                 240

Glu Ser Asn Gly Gly Phe Leu Ala Pro Arg Tyr Gly Tyr Ile Ile Glu
                245                 250                 255

Glu Tyr Gly Lys Gly Arg Ile Phe Gln Ser Arg Ile Arg Met Ser Arg
            260                 265                 270

Cys Asn Thr Lys Cys Gln Thr Ser Val Gly Gly Ile Asn Thr Asn Arg
        275                 280                 285

Thr Phe Gln Asn Ile Asp Lys Asn Ala Leu Gly Asp Cys Pro Lys Tyr
290                 295                 300

Ile Lys Ser Gly Gln Leu Lys Leu Ala Thr Gly Leu Arg Asn Val Pro
305                 310                 315                 320

Ala Ile Ser Asn Arg

```
<210> SEQ ID NO 43
<211> LENGTH: 325
<212> TYPE: PRT
<213> ORGANISM: Influenza A

<400> SEQUENCE: 43

Asp Lys Ile Cys Ile Gly Tyr Leu Ser Asn Asn Ser Ser Asp Thr Val
1               5                   10                  15

Asp Thr Leu Thr Glu Asn Gly Val Pro Val Thr Ser Ser Val Asp Leu
            20                  25                  30

Val Glu Thr Asn His Thr Gly Thr Tyr Cys Ser Leu Asn Gly Ile Ser
        35                  40                  45

Pro Ile His Leu Gly Asp Cys Ser Phe Glu Gly Trp Ile Val Gly Asn
    50                  55                  60

Pro Ser Cys Ala Thr Asn Ile Asn Ile Arg Glu Trp Ser Tyr Leu Ile
65                  70                  75                  80

Glu Asp Pro Asn Ala Pro Asn Lys Leu Cys Tyr Pro Gly Glu Leu Asp
                85                  90                  95

Asn Asn Gly Glu Leu Arg His Leu Phe Ser Gly Val Asn Ser Phe Ser
            100                 105                 110

Arg Thr Glu Leu Ile Asn Pro Ser Lys Trp Gly Asn Val Leu Asp Gly
        115                 120                 125

Val Thr Ala Ser Cys Leu Asp Arg Gly Ala Ser Ser Phe Tyr Arg Asn
    130                 135                 140

Leu Val Trp Leu Val Lys Gln Lys Ile Gly Glu Tyr Pro Val Val Lys
145                 150                 155                 160

Gly Glu Tyr Asn Asn Thr Thr Gly Arg Asp Val Leu Val Leu Trp Gly
                165                 170                 175

Ile His His Pro Asp Thr Glu Thr Thr Ala Thr Asn Leu Tyr Val Asn
            180                 185                 190

Lys Asn Pro Tyr Thr Leu Val Ser Thr Lys Glu Trp Ser Lys Arg Tyr
        195                 200                 205

Glu Leu Glu Ile Gly Thr Arg Ile Gly Asp Gly Gln Arg Ser Trp Met
    210                 215                 220

Lys Leu Tyr Trp His Leu Met His Pro Gly Glu Arg Ile Met Phe Glu
225                 230                 235                 240

Ser Asn Gly Gly Leu Ile Ala Pro Arg Tyr Gly Tyr Ile Ile Glu Lys
                245                 250                 255

Tyr Gly Thr Gly Thr Ile Phe Gln Ser Gly Val Arg Met Ala Lys Cys
            260                 265                 270

Asn Thr Lys Cys Gln Thr Ser Leu Gly Gly Ile Asn Thr Asn Lys Thr
        275                 280                 285

Phe Gln Asn Ile Glu Arg Asn Ala Leu Gly Asp Cys Pro Lys Tyr Ile
    290                 295                 300

Lys Ser Gly Gln Leu Lys Leu Ala Thr Gly Leu Arg Asn Val Pro Ile
305                 310                 315                 320

Pro Ile Gly Glu Arg
                325

<210> SEQ ID NO 44
<211> LENGTH: 324
<212> TYPE: PRT
<213> ORGANISM: Influenza A
```

<400> SEQUENCE: 44

Asp Arg Ile Cys Ile Gly Tyr Gln Ala Asn Gln Asn Gln Thr Val
1               5                   10                  15

Asn Thr Leu Leu Glu Gln Asn Val Pro Val Thr Gly Ala Gln Glu Ile
            20                  25                  30

Leu Glu Thr Asn His Asn Gly Lys Leu Cys Ser Leu Asn Gly Val Pro
        35                  40                  45

Pro Leu Asp Leu Gln Ser Cys Thr Leu Ala Gly Trp Leu Leu Gly Asn
50                  55                  60

Pro Asn Cys Asp Asn Leu Leu Glu Ala Glu Glu Trp Ser Tyr Ile Lys
65                  70                  75                  80

Ile Asn Glu Asn Ala Pro Asp Asp Leu Cys Phe Pro Gly Asn Phe Glu
                85                  90                  95

Asn Leu Gln Asp Leu Leu Leu Glu Met Ser Gly Val Asn Phe Thr
            100                 105                 110

Lys Val Lys Leu Phe Asn Pro Gln Ser Met Thr Gly Val Thr Thr Asn
        115                 120                 125

Asn Val Asp Gln Thr Cys Pro Phe Glu Gly Lys Pro Ser Phe Tyr Arg
130                 135                 140

Asn Leu Asn Trp Ile Gln Gly Asn Ser Gly Leu Pro Phe Asn Ile Glu
145                 150                 155                 160

Ile Lys Asn Pro Thr Ser Asn Pro Leu Leu Leu Trp Gly Ile His
                165                 170                 175

Asn Thr Lys Asp Ala Ala Gln Gln Arg Asn Leu Tyr Gly Asn Asp Tyr
            180                 185                 190

Ser Tyr Thr Ile Phe Asn Phe Gly Glu Lys Ser Glu Glu Phe Arg Pro
        195                 200                 205

Asp Ile Gly Gln Arg Asp Glu Ile Lys Ala His Gln Asp Arg Ile Asp
210                 215                 220

Tyr Tyr Trp Gly Ser Leu Pro Ala Gln Ser Thr Leu Arg Ile Glu Ser
225                 230                 235                 240

Thr Gly Asn Leu Ile Ala Pro Glu Tyr Gly Phe Tyr Lys Arg Lys
                245                 250                 255

Glu Gly Lys Gly Gly Leu Met Lys Ser Lys Leu Pro Ile Ser Asp Cys
            260                 265                 270

Ser Thr Lys Cys Gln Thr Pro Leu Gly Ala Leu Asn Ser Thr Leu Pro
        275                 280                 285

Phe Gln Asn Val His Gln Thr Ile Gly Asn Cys Pro Lys Tyr Val
290                 295                 300

Lys Ala Thr Ser Leu Met Leu Ala Thr Gly Leu Arg Asn Asn Pro Gln
305                 310                 315                 320

Met Glu Gly Arg

<210> SEQ ID NO 45
<211> LENGTH: 325
<212> TYPE: PRT
<213> ORGANISM: Influenza A

<400> SEQUENCE: 45

Asp Gln Ile Cys Ile Gly Tyr His Ser Asn Asn Ser Thr Gln Thr Val
1               5                   10                  15

Asn Thr Leu Leu Glu Ser Asn Val Pro Val Thr Ser Ser His Ser Ile
            20                  25                  30

Leu Glu Lys Glu His Asn Gly Leu Leu Cys Lys Leu Lys Gly Lys Ala

```
                35                  40                  45
Pro Leu Asp Leu Ile Asp Cys Ser Leu Pro Ala Trp Leu Met Gly Asn
 50                  55                  60

Pro Lys Cys Asp Glu Leu Leu Thr Ala Ser Glu Trp Ala Tyr Ile Lys
 65                  70                  75                  80

Glu Asp Pro Glu Pro Glu Asn Gly Ile Cys Phe Pro Gly Asp Phe Asp
                 85                  90                  95

Ser Leu Glu Asp Leu Ile Leu Leu Val Ser Asn Thr Asp His Phe Arg
            100                 105                 110

Lys Glu Lys Ile Ile Asp Met Thr Arg Phe Ser Asp Val Thr Thr Asn
            115                 120                 125

Asn Val Asp Ser Ala Cys Pro Tyr Asp Thr Asn Gly Ala Ser Phe Tyr
130                 135                 140

Arg Asn Leu Asn Trp Val Gln Gln Asn Lys Gly Lys Gln Leu Ile Phe
145                 150                 155                 160

His Tyr Gln Asn Ser Glu Asn Asn Pro Leu Leu Ile Ile Trp Gly Val
                165                 170                 175

His Gln Thr Ser Asn Ala Ala Glu Gln Asn Thr Tyr Tyr Gly Ser Gln
            180                 185                 190

Thr Gly Ser Thr Thr Ile Thr Ile Gly Glu Glu Thr Asn Thr Tyr Pro
        195                 200                 205

Leu Val Ile Ser Glu Ser Ser Ile Leu Asn Gly His Ser Asp Arg Ile
    210                 215                 220

Asn Tyr Phe Trp Gly Val Val Asn Pro Asn Gln Asn Phe Ser Ile Val
225                 230                 235                 240

Ser Thr Gly Asn Phe Ile Trp Pro Glu Tyr Gly Tyr Phe Phe Gln Lys
                245                 250                 255

Thr Thr Asn Ile Ser Gly Ile Ile Lys Ser Ser Glu Lys Ile Ser Asp
            260                 265                 270

Cys Asp Thr Ile Cys Gln Thr Lys Ile Gly Ala Ile Asn Ser Thr Leu
        275                 280                 285

Pro Phe Gln Asn Ile His Gln Asn Ala Ile Gly Asp Cys Pro Lys Tyr
    290                 295                 300

Val Lys Ala Gln Glu Leu Val Leu Ala Thr Gly Leu Arg Asn Asn Pro
305                 310                 315                 320

Ile Lys Glu Thr Arg
            325

<210> SEQ ID NO 46
<211> LENGTH: 329
<212> TYPE: PRT
<213> ORGANISM: Influenza A

<400> SEQUENCE: 46

Gln Asp Leu Pro Gly Asn Asp Asn Ser Thr Ala Thr Leu Cys Leu Gly
 1               5                  10                  15

His His Ala Val Pro Asn Gly Thr Leu Val Lys Thr Ile Thr Asp Asp
                 20                  25                  30

Gln Ile Glu Val Thr Asn Ala Thr Glu Leu Val Gln Ser Ser Ser Thr
            35                  40                  45

Gly Lys Ile Cys Asn Asn Pro His Arg Ile Leu Asp Gly Ile Asp Cys
        50                  55                  60

Thr Leu Ile Asp Ala Leu Leu Gly Asp Pro His Cys Asp Val Phe Gln
 65                  70                  75                  80
```

```
Asn Glu Thr Trp Asp Leu Phe Val Glu Arg Ser Lys Ala Phe Ser Asn
            85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
            115                 120                 125

Gly Val Thr Gln Asn Gly Gly Ser Asn Ala Cys Lys Arg Gly Pro Gly
130             135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Ile His His Pro Ser Thr Asn Gln Glu Gln Thr
            180                 185                 190

Ser Leu Tyr Val Gln Ala Ser Gly Arg Val Thr Val Ser Thr Arg Arg
            195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
            275                 280                 285

Pro Asn Asp Lys Pro Phe Gln Asn Val Asn Lys Ile Thr Tyr Gly Ala
            290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg
                325

<210> SEQ ID NO 47
<211> LENGTH: 327
<212> TYPE: PRT
<213> ORGANISM: Influenza A

<400> SEQUENCE: 47

Gln Asn Tyr Thr Gly Asn Pro Val Ile Cys Leu Gly His His Ala Val
1               5                   10                  15

Ser Asn Gly Thr Met Val Lys Thr Leu Thr Asp Asp Gln Ile Glu Val
            20                  25                  30

Val Thr Ala Gln Glu Leu Val Glu Ser Gln His Leu Pro Glu Leu Cys
        35                  40                  45

Pro Ser Pro Leu Arg Leu Val Asp Gly Gln Thr Cys Asp Ile Val Asn
    50                  55                  60

Gly Ala Leu Gly Ser Pro Gly Cys Asp His Leu Asn Gly Ala Glu Trp
65                  70                  75                  80

Asp Val Phe Ile Glu Arg Pro Thr Ala Val Asp Thr Cys Tyr Pro Phe
                85                  90                  95

Asp Val Pro Asp Tyr Gln Ser Leu Arg Ser Ile Leu Ala Asn Asn Gly
            100                 105                 110

Lys Phe Glu Phe Ile Ala Glu Glu Phe Gln Trp Asn Thr Val Lys Gln
        115                 120                 125
```

```
Asn Gly Lys Ser Gly Ala Cys Lys Arg Ala Asn Val Asn Asp Phe Phe
            130                 135                 140

Asn Arg Leu Asn Trp Leu Thr Lys Ser Asp Gly Asn Ala Tyr Pro Leu
145                 150                 155                 160

Gln Asn Leu Thr Lys Val Asn Asn Gly Asp Tyr Ala Arg Leu Tyr Ile
                165                 170                 175

Trp Gly Val His His Pro Ser Thr Asp Thr Glu Gln Thr Asn Leu Tyr
            180                 185                 190

Lys Asn Asn Pro Gly Arg Val Thr Val Ser Thr Gln Thr Ser Gln Thr
        195                 200                 205

Ser Val Val Pro Asn Ile Gly Ser Arg Pro Trp Val Arg Gly Leu Ser
210                 215                 220

Ser Arg Ile Ser Phe Tyr Trp Thr Ile Val Glu Pro Gly Asp Leu Ile
225                 230                 235                 240

Val Phe Asn Thr Ile Gly Asn Leu Ile Ala Pro Arg Gly His Tyr Lys
                245                 250                 255

Leu Asn Ser Gln Lys Lys Ser Thr Ile Leu Asn Thr Ala Val Pro Ile
            260                 265                 270

Gly Ser Cys Val Ser Lys Cys His Thr Asp Lys Gly Ser Ile Ser Thr
            275                 280                 285

Thr Lys Pro Phe Gln Asn Ile Ser Arg Ile Ser Ile Gly Asp Cys Pro
290                 295                 300

Lys Tyr Val Lys Gln Gly Ser Leu Lys Leu Ala Thr Gly Met Arg Asn
305                 310                 315                 320

Ile Pro Glu Lys Ala Thr Arg
                325

<210> SEQ ID NO 48
<211> LENGTH: 321
<212> TYPE: PRT
<213> ORGANISM: Influenza A

<400> SEQUENCE: 48

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
                20                  25                  30

Val Glu Arg Thr Asn Val Pro Arg Ile Cys Ser Lys Gly Lys Arg Thr
            35                  40                  45

Val Asp Leu Gly Gln Cys Gly Leu Leu Gly Thr Ile Thr Gly Pro Pro
50                  55                  60

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Thr
            100                 105                 110

Met Gly Phe Thr Tyr Ser Gly Ile Arg Thr Asn Gly Ala Thr Ser Ala
        115                 120                 125

Cys Arg Arg Ser Gly Ser Ser Phe Tyr Ala Glu Met Lys Trp Leu Leu
130                 135                 140

Ser Asn Thr Asp Asn Ala Ala Phe Pro Gln Met Thr Lys Ser Tyr Lys
145                 150                 155                 160

Asn Thr Arg Lys Asp Pro Ala Leu Ile Ile Trp Gly Ile His His Ser
```

```
                    165                 170                 175
Gly Ser Thr Thr Glu Gln Thr Lys Leu Tyr Gly Ser Gly Asn Lys Leu
                180                 185                 190

Ile Thr Val Gly Ser Ser Asn Tyr Gln Gln Ser Phe Val Pro Ser Pro
                195                 200                 205

Gly Ala Arg Pro Gln Val Asn Gly Gln Ser Gly Arg Ile Asp Phe His
            210                 215                 220

Trp Leu Met Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Ser Val Gln Val Asp Ala Asn Cys Glu Gly Asp Cys
                260                 265                 270

Tyr His Ser Gly Gly Thr Ile Ile Ser Asn Leu Pro Phe Gln Asn Ile
            275                 280                 285

Asn Ser Arg Ala Val Gly Lys Cys Pro Arg Tyr Val Lys Gln Glu Ser
            290                 295                 300

Leu Met Leu Ala Thr Gly Met Lys Asn Val Pro Glu Ile Pro Lys Gly
305                 310                 315                 320

Arg

<210> SEQ ID NO 49
<211> LENGTH: 324
<212> TYPE: PRT
<213> ORGANISM: Influenza A

<400> SEQUENCE: 49

Leu Asp Lys Ile Cys Leu Gly His His Ala Val Ala Asn Gly Thr Ile
1               5                   10                  15

Val Lys Thr Leu Thr Asn Glu Gln Glu Glu Val Thr Asn Ala Thr Glu
                20                  25                  30

Thr Val Glu Ser Thr Ser Leu Asn Arg Leu Cys Met Lys Gly Arg Asn
            35                  40                  45

His Lys Asp Leu Gly Asn Cys His Pro Ile Gly Met Leu Ile Gly Thr
        50                  55                  60

Pro Ala Cys Asp Leu His Leu Thr Gly Thr Trp Asp Thr Leu Ile Glu
65                  70                  75                  80

Arg Glu Asn Ala Ile Ala Tyr Cys Tyr Pro Gly Ala Thr Val Asn Glu
                85                  90                  95

Glu Ala Leu Arg Gln Lys Ile Met Glu Ser Gly Gly Ile Ser Lys Ile
            100                 105                 110

Ser Thr Gly Phe Thr Tyr Gly Ser Ser Ile Asn Ser Ala Gly Thr Thr
        115                 120                 125

Lys Ala Cys Met Arg Asn Gly Gly Asn Ser Phe Tyr Ala Glu Leu Lys
    130                 135                 140

Trp Leu Val Ser Lys Ser Lys Gly Gln Asn Phe Pro Gln Thr Thr Asn
145                 150                 155                 160

Thr Tyr Arg Asn Thr Asp Thr Ala Glu His Ile Ile Met Trp Gly Ile
                165                 170                 175

His His Pro Ser Ser Thr Gln Glu Lys Asn Asp Leu Tyr Gly Thr Gln
            180                 185                 190

Ser Leu Ser Ile Ser Val Gly Ser Ser Thr Tyr Gln Asn Asn Phe Val
        195                 200                 205

Pro Val Val Gly Ala Arg Pro Gln Val Asn Gly Gln Ser Gly Arg Ile
```

```
            210                 215                 220
Asp Phe His Trp Thr Leu Val Gln Pro Gly Asp Asn Ile Thr Phe Ser
225                 230                 235                 240

His Asn Gly Gly Leu Ile Ala Pro Ser Arg Val Ser Lys Leu Ile Gly
                245                 250                 255

Arg Gly Leu Gly Ile Gln Ser Asp Ala Pro Ile Asp Asn Asn Cys Glu
                260                 265                 270

Ser Lys Cys Phe Trp Arg Gly Gly Ser Ile Asn Thr Arg Leu Pro Phe
                275                 280                 285

Gln Asn Leu Ser Pro Arg Thr Val Gly Gln Cys Pro Lys Tyr Val Asn
                290                 295                 300

Lys Lys Ser Leu Met Leu Ala Thr Gly Met Arg Asn Val Pro Glu Ile
305                 310                 315                 320

Met Gln Gly Arg

<210> SEQ ID NO 50
<211> LENGTH: 330
<212> TYPE: PRT
<213> ORGANISM: Influenza A

<400> SEQUENCE: 50

Gln Ile Thr Asn Gly Thr Thr Gly Asn Pro Ile Ile Cys Leu Gly His
1               5                   10                  15

His Ala Val Glu Asn Gly Thr Ser Val Lys Thr Leu Thr Asp Asn His
                20                  25                  30

Val Glu Val Val Ser Ala Lys Glu Leu Val Glu Thr Asn His Thr Asp
            35                  40                  45

Glu Leu Cys Pro Ser Pro Leu Lys Leu Val Asp Gly Gln Asp Cys Asp
        50                  55                  60

Leu Ile Asn Gly Ala Leu Gly Ser Pro Gly Cys Asp Arg Leu Gln Asp
65                  70                  75                  80

Thr Thr Trp Asp Val Phe Ile Glu Arg Pro Thr Ala Val Asp Thr Cys
                85                  90                  95

Tyr Pro Phe Asp Val Pro Asp Tyr Gln Ser Leu Arg Ser Ile Leu Ala
                100                 105                 110

Ser Ser Gly Ser Leu Glu Phe Ile Ala Glu Gln Phe Thr Trp Asn Gly
            115                 120                 125

Val Lys Val Asp Gly Ser Ser Ala Cys Leu Arg Gly Gly Arg Asn
            130                 135                 140

Ser Phe Phe Ser Arg Leu Asn Trp Leu Thr Lys Ala Thr Asn Gly Asn
145                 150                 155                 160

Tyr Gly Pro Ile Asn Val Thr Lys Glu Asn Thr Gly Ser Tyr Val Arg
                165                 170                 175

Leu Tyr Leu Trp Gly Val His His Pro Ser Ser Asp Asn Glu Gln Thr
                180                 185                 190

Asp Leu Tyr Lys Val Ala Thr Gly Arg Val Thr Val Ser Thr Arg Ser
            195                 200                 205

Asp Gln Ile Ser Ile Val Pro Asn Ile Gly Ser Arg Pro Arg Val Arg
        210                 215                 220

Asn Gln Ser Gly Arg Ile Ser Ile Tyr Trp Thr Leu Val Asn Pro Gly
225                 230                 235                 240

Asp Ser Ile Ile Phe Asn Ser Ile Gly Asn Leu Ile Ala Pro Arg Gly
                245                 250                 255

His Tyr Lys Ile Ser Lys Ser Thr Lys Ser Thr Val Leu Lys Ser Asp
```

```
            260                 265                 270
Lys Arg Ile Gly Ser Cys Thr Ser Pro Cys Leu Thr Asp Lys Gly Ser
            275                 280                 285

Ile Gln Ser Asp Lys Pro Phe Gln Asn Val Ser Arg Ile Ala Ile Gly
    290                 295                 300

Asn Cys Pro Lys Tyr Val Lys Gln Gly Ser Leu Met Leu Ala Thr Gly
305                 310                 315                 320

Met Arg Asn Ile Pro Gly Lys Gln Ala Arg
                325                 330

<210> SEQ ID NO 51
<211> LENGTH: 331
<212> TYPE: PRT
<213> ORGANISM: Influenza A

<400> SEQUENCE: 51

Asp Lys Ile Cys Leu Gly His His Ala Val Ala Asn Gly Thr Lys Val
1               5                   10                  15

Asn Thr Leu Thr Glu Lys Gly Val Glu Val Asn Ala Thr Glu Thr
            20                  25                  30

Val Glu Ile Thr Gly Ile Asn Lys Val Cys Thr Lys Gly Lys Lys Ala
            35                  40                  45

Val Asp Leu Gly Ser Cys Gly Ile Leu Gly Thr Ile Ile Gly Pro Pro
    50                  55                  60

Gln Cys Asp Ser His Leu Lys Phe Lys Ala Asp Leu Ile Ile Glu Arg
65                  70                  75                  80

Arg Asn Ser Ser Asp Ile Cys Tyr Pro Gly Lys Phe Thr Asn Glu Glu
                85                  90                  95

Ala Leu Arg Gln Ile Ile Arg Glu Ser Gly Gly Ile Asp Lys Glu Pro
            100                 105                 110

Met Gly Phe Arg Tyr Ser Gly Ile Lys Thr Asp Gly Ala Thr Ser Ala
        115                 120                 125

Cys Lys Arg Thr Val Ser Ser Phe Tyr Ser Glu Met Lys Trp Leu Leu
    130                 135                 140

Ser Ser Lys Ala Asn Gln Val Phe Pro Gln Leu Asn Gln Thr Tyr Arg
145                 150                 155                 160

Asn Asn Arg Lys Glu Pro Ala Leu Ile Val Trp Gly Val His His Ser
                165                 170                 175

Ser Ser Leu Asp Glu Gln Asn Lys Leu Tyr Gly Ala Gly Asn Lys Leu
            180                 185                 190

Ile Thr Val Gly Ser Ser Lys Tyr Gln Gln Ser Phe Ser Pro Ser Pro
        195                 200                 205

Gly Asp Arg Pro Lys Val Asn Gly Gln Ala Gly Arg Ile Asp Phe His
    210                 215                 220

Trp Met Leu Leu Asp Pro Gly Asp Thr Val Thr Phe Thr Phe Asn Gly
225                 230                 235                 240

Ala Phe Ile Ala Pro Asp Arg Ala Thr Phe Leu Arg Ser Asn Ala Pro
                245                 250                 255

Ser Gly Val Glu Tyr Asn Gly Lys Ser Leu Gly Ile Gln Ser Asp Ala
            260                 265                 270

Gln Ile Asp Glu Ser Cys Glu Gly Glu Cys Phe Tyr Ser Gly Gly Thr
        275                 280                 285

Ile Asn Ser Pro Leu Pro Phe Gln Asn Ile Asp Ser Trp Ala Val Gly
    290                 295                 300
```

```
Arg Cys Pro Arg Tyr Val Lys Gln Ser Ser Leu Pro Leu Ala Leu Gly
305                 310                 315                 320

Met Lys Asn Val Pro Glu Lys Ile His Thr Arg
                325             330
```